(12) United States Patent  
Balakin

(10) Patent No.: US 8,198,607 B2  
(45) Date of Patent: Jun. 12, 2012

(54) TANDEM ACCELERATOR METHOD AND APPARATUS USED IN CONJUNCTION WITH A CHARGED PARTICLE CANCER THERAPY SYSTEM

(76) Inventor: Vladimir Balakin, Protvino (RU)

( * ) Notice: Subject to any disclaimer, the term of this patent is extended or adjusted under 35 U.S.C. 154(b) by 420 days.

(21) Appl. No.: 12/614,733

(22) Filed: Nov. 9, 2009

(65) Prior Publication Data

US 2010/0059686 A1    Mar. 11, 2010

Related U.S. Application Data

(63) Continuation-in-part of application No. 12/425,683, filed on Apr. 17, 2009, now Pat. No. 7,939,809.

(60) Provisional application No. 61/055,395, filed on May 22, 2008, provisional application No. 61/137,574, filed on Aug. 1, 2008, provisional application No. 61/192,245, filed on Sep. 17, 2008, provisional (Continued)

(51) Int. Cl.
  *A61N 5/00*  (2006.01)
(52) U.S. Cl. .............. 250/492.1; 250/492.3; 250/396 R; 313/62; 315/503; 315/504
(58) Field of Classification Search ............. 250/396 R, 250/492.1, 492.3; 313/62; 315/503, 504
See application file for complete search history.

(56) References Cited

U.S. PATENT DOCUMENTS 2,306,875 A    12/1942    Fremlin (Continued)

FOREIGN PATENT DOCUMENTS

EP    1683545 A2    7/2006

(Continued)

OTHER PUBLICATIONS

Yi, et al ("A Thin Beryllium Injection Window for CESR-C" Proceedings of the 2003 Particle Accelerator conference, p. 2264-2266, 2003).*

(Continued)

*Primary Examiner* — Michael Maskell
(74) *Attorney, Agent, or Firm* — Kevin Hazen

(57) ABSTRACT

The invention comprises a tandem accelerator method and apparatus, which is part of an ion beam injection system used in conjunction with multi-axis charged particle radiation therapy of cancerous tumors. The negative ion beam source includes an injection system vacuum system and a synchrotron vacuum system separated by a foil, where negative ions are converted to positive ions. The foil is sealed to the edges of the vacuum tube providing for a higher partial pressure in the injection system vacuum chamber and a lower pressure in the synchrotron vacuum system. Having the foil physically separating the vacuum chamber into two pressure regions allows for fewer and/or smaller pumps to maintain the lower pressure system in the synchrotron as the inlet hydrogen gas is extracted in a separate contained and isolated space by the injection partial vacuum system.

30 Claims, 24 Drawing Sheets

Related U.S. Application Data application No. 61/055,409, filed on May 22, 2008, provisional application No. 61/203,308, filed on Dec. 22, 2008, provisional application No. 61/188,407, filed on Aug. 11, 2008, provisional application No. 61/188,406, filed on Aug. 11, 2008, provisional application No. 61/189,815, filed on Aug. 25, 2008, provisional application No. 61/201,731, filed on Dec. 15, 2008, provisional application No. 61/205,362, filed on Jan. 21, 2009, provisional application No. 61/134,717, filed on Jul. 14, 2008, provisional application No. 61/134,707, filed on Jul. 14, 2008, provisional application No. 61/201,732, filed on Dec. 15, 2008, provisional application No. 61/198,509, filed on Nov. 7, 2008, provisional application No. 61/134,718, filed on Jul. 14, 2008, provisional application No. 61/190,613, filed on Sep. 2, 2008, provisional application No. 61/191,043, filed on Sep. 8, 2008, provisional application No. 61/192,237, filed on Sep. 17, 2008, provisional application No. 61/201,728, filed on Dec. 15, 2008, provisional application No. 61/190,546, filed on Sep. 2, 2008, provisional application No. 61/189,017, filed on Aug. 15, 2008, provisional application No. 61/198,248, filed on Nov. 5, 2008, provisional application No. 61/198,508, filed on Nov. 7, 2008, provisional application No. 61/197,971, filed on Nov. 3, 2008, provisional application No. 61/199,405, filed on Nov. 17, 2008, provisional application No. 61/199,403, filed on Nov. 17, 2008, provisional application No. 61/199,404, filed on Nov. 17, 2008, provisional application No. 61/209,529, filed on Mar. 9, 2009, provisional application No. 61/208,182, filed on Feb. 23, 2009, provisional application No. 61/208,971, filed on Mar. 3, 2009, provisional application No. 61/270,298, filed on Jul. 7, 2009.

(56) References Cited

U.S. PATENT DOCUMENTS

| | | | |
|---|---|---|---|
| 2,790,902 A | 4/1957 | Wright | |
| 3,128,405 A | 4/1964 | Lambertson | |
| 3,412,337 A | 11/1968 | Lothrop | |
| 3,655,968 A | 4/1972 | Moore | |
| 3,867,705 A | 2/1975 | Hudson | |
| 3,882,339 A | 5/1975 | Rate | |
| 3,906,280 A | 9/1975 | Andelfinger | |
| 4,002,912 A | 1/1977 | Johnson | |
| 4,344,011 A | 8/1982 | Hayashi | |
| 4,607,380 A | 8/1986 | Oliver | |
| 4,622,687 A | 11/1986 | Whitaker | |
| 4,726,046 A | 2/1988 | Nunan | |
| 4,730,353 A | 3/1988 | Ono | |
| 4,868,844 A | 9/1989 | Nunan | |
| 4,870,287 A | 9/1989 | Cole | |
| 4,998,258 A | 3/1991 | Ikeda | |
| 5,017,789 A | 5/1991 | Young | |
| 5,039,867 A | 8/1991 | Nishihara | |
| 5,073,913 A * | 12/1991 | Martin | 378/34 |
| 5,168,241 A | 12/1992 | Hirota | |
| 5,177,448 A | 1/1993 | Ikeguchi | |
| 5,260,581 A | 11/1993 | Lesyna | |
| 5,285,166 A | 2/1994 | Hiramoto | |
| 5,349,198 A | 9/1994 | Takanaka | |
| 5,363,008 A | 11/1994 | Hiramoto | |
| 5,388,580 A | 2/1995 | Sullivan | |
| 5,440,133 A | 8/1995 | Moyers | |
| 5,483,129 A | 1/1996 | Yamamoto | |
| 5,511,549 A | 4/1996 | Legg | |
| 5,538,494 A | 7/1996 | Matsuda | |
| 5,568,109 A | 10/1996 | Takayama | |
| 5,576,549 A | 11/1996 | Hell | |
| 5,585,642 A | 12/1996 | Britton | |
| 5,600,213 A | 2/1997 | Hiramoto | |
| 5,626,682 A | 5/1997 | Kobari | |
| 5,633,907 A | 5/1997 | Gravelle | |
| 5,659,223 A * | 8/1997 | Goodman | 315/39 |
| 5,661,366 A | 8/1997 | Hirota | |
| 5,668,371 A | 9/1997 | Deasy | |
| 5,698,954 A | 12/1997 | Hirota | |
| 5,760,395 A | 6/1998 | Johnstone | |
| 5,789,875 A | 8/1998 | Hiramoto | |
| 5,818,058 A | 10/1998 | Nakanishi | |
| 5,820,320 A | 10/1998 | Kobari | |
| 5,825,845 A | 10/1998 | Blair | |
| 5,866,912 A | 2/1999 | Slater | |
| 5,895,926 A | 4/1999 | Britton | |
| 5,907,595 A | 5/1999 | Sommerer | |
| 5,917,293 A | 6/1999 | Saito | |
| 5,969,367 A | 10/1999 | Hiramoto | |
| 5,986,274 A | 11/1999 | Akiyama | |
| 5,993,373 A | 11/1999 | Nonaka | |
| 6,008,499 A | 12/1999 | Hiramoto | |
| 6,034,377 A | 3/2000 | Pu | |
| 6,057,655 A | 5/2000 | Jongen | |
| 6,087,670 A | 7/2000 | Hiramoto | |
| 6,087,672 A | 7/2000 | Matsuda | |
| 6,148,058 A | 11/2000 | Dobbs | |
| 6,207,952 B1 | 3/2001 | Kan | |
| 6,218,675 B1 | 4/2001 | Akiyama | |
| 6,236,043 B1 | 5/2001 | Tadokoro | |
| 6,265,837 B1 | 7/2001 | Akiyama | |
| 6,282,263 B1 | 8/2001 | Arndt | |
| 6,316,776 B1 | 11/2001 | Hiramoto | |
| 6,322,249 B1 | 11/2001 | Wofford | |
| 6,335,535 B1 | 1/2002 | Miyake | |
| 6,339,635 B1 | 1/2002 | Schardt | |
| 6,356,617 B1 | 3/2002 | Besch | |
| 6,365,894 B2 | 4/2002 | Tadokoro | |
| 6,421,416 B1 | 7/2002 | Sliski | |
| 6,433,336 B1 | 8/2002 | Jongen | |
| 6,433,349 B2 | 8/2002 | Akiyama | |
| 6,433,494 B1 | 8/2002 | Kulish | |
| 6,437,513 B1 | 8/2002 | Stelzer | |
| 6,444,990 B1 | 9/2002 | Morgan | |
| 6,462,490 B1 | 10/2002 | Matsuda | |
| 6,470,068 B2 | 10/2002 | Cheng | |
| 6,472,834 B2 | 10/2002 | Hiramoto | |
| 6,476,403 B1 | 11/2002 | Dolinskii | |
| 6,545,436 B1 | 4/2003 | Gary | |
| 6,560,354 B1 | 5/2003 | Maurer, Jr. | |
| 6,580,084 B1 | 6/2003 | Hiramoto | |
| 6,597,005 B1 | 7/2003 | Badura | |
| 6,600,164 B1 | 7/2003 | Badura | |
| 6,614,038 B1 | 9/2003 | Brand | |
| 6,617,598 B1 | 9/2003 | Matsuda | |
| 6,626,842 B2 | 9/2003 | Oka | |
| 6,635,882 B1 | 10/2003 | Pavlovic | |
| 6,639,234 B1 | 10/2003 | Badura | |
| 6,670,618 B1 | 12/2003 | Hartmann | |
| 6,683,318 B1 | 1/2004 | Haberer | |
| 6,683,426 B1 | 1/2004 | Kleeven | |
| 6,710,362 B2 | 3/2004 | Kraft | |
| 6,717,162 B1 | 4/2004 | Jongen | |
| 6,730,921 B2 | 5/2004 | Kraft | |
| 6,736,831 B1 | 5/2004 | Hartmann | |
| 6,745,072 B1 | 6/2004 | Badura | |
| 6,774,383 B2 | 8/2004 | Norimine | |
| 6,777,700 B2 | 8/2004 | Yanagisawa | |
| 6,785,359 B2 | 8/2004 | Lemaitre | |
| 6,787,771 B2 | 9/2004 | Bashkirov | |
| 6,792,078 B2 | 9/2004 | Kato | |
| 6,799,068 B1 | 9/2004 | Hartmann | |
| 6,800,866 B2 | 10/2004 | Amemiya | |
| 6,803,591 B2 | 10/2004 | Muramatsu | |
| 6,809,325 B2 | 10/2004 | Dahl | |
| 6,819,743 B2 | 11/2004 | Kato | |
| 6,822,244 B2 | 11/2004 | Beloussov | |
| 6,823,045 B2 | 11/2004 | Kato | |

| | | |
|---|---|---|
| 6,838,676 B1 | 1/2005 | Jackson |
| 6,859,741 B2 | 2/2005 | Haberer |
| 6,873,123 B2 | 3/2005 | Marchand |
| 6,881,970 B2 | 4/2005 | Akiyama |
| 6,891,177 B1 | 5/2005 | Kraft |
| 6,897,451 B2 | 5/2005 | Kaercher |
| 6,900,446 B2 | 5/2005 | Akiyama |
| 6,903,351 B1 | 6/2005 | Akiyama |
| 6,903,356 B2 | 6/2005 | Muramatsu |
| 6,931,100 B2 | 8/2005 | Kato |
| 6,936,832 B2 | 8/2005 | Norimine |
| 6,937,696 B1 | 8/2005 | Mostafavi |
| 6,953,943 B2 | 10/2005 | Yanagisawa |
| 6,979,832 B2 | 12/2005 | Yanagisawa |
| 6,984,835 B2 | 1/2006 | Harada |
| 6,992,312 B2 | 1/2006 | Yanagisawa |
| 6,998,258 B1 | 2/2006 | Kesseler |
| 7,012,267 B2 | 3/2006 | Moriyama |
| 7,026,636 B2 | 4/2006 | Yanagisawa |
| 7,030,396 B2 | 4/2006 | Muramatsu |
| 7,045,781 B2 | 5/2006 | Adamec |
| 7,049,613 B2 | 5/2006 | Yanagisawa |
| 7,053,389 B2 | 5/2006 | Yanagisawa |
| 7,054,801 B2 | 5/2006 | Sakamoto |
| 7,058,158 B2 | 6/2006 | Sako |
| 7,060,997 B2 | 6/2006 | Norimine et al. |
| 7,071,479 B2 | 7/2006 | Yanagisawa |
| 7,081,619 B2 | 7/2006 | Bashkirov |
| 7,084,410 B2 | 8/2006 | Beloussov |
| 7,091,478 B2 | 8/2006 | Haberer |
| 7,102,144 B2 | 9/2006 | Matsuda |
| 7,109,505 B1 | 9/2006 | Sliski |
| 7,122,811 B2 | 10/2006 | Matsuda |
| 7,141,810 B2 | 11/2006 | Kakiuchi |
| 7,154,107 B2 | 12/2006 | Yanagisawa |
| 7,154,108 B2 | 12/2006 | Tadokoro |
| 7,173,264 B2 | 2/2007 | Moriyama |
| 7,173,265 B2 | 2/2007 | Miller |
| 7,193,227 B2 | 3/2007 | Hiramoto |
| 7,199,382 B2 | 4/2007 | Rigney |
| 7,208,748 B2 | 4/2007 | Sliski |
| 7,212,608 B2 | 5/2007 | Nagamine |
| 7,212,609 B2 | 5/2007 | Nagamine |
| 7,227,161 B2 | 6/2007 | Matsuda |
| 7,247,869 B2 | 7/2007 | Tadokoro |
| 7,252,745 B2 | 8/2007 | Gorokhovsky |
| 7,259,529 B2 | 8/2007 | Tanaka |
| 7,262,424 B2 | 8/2007 | Moriyama |
| 7,274,018 B2 | 9/2007 | Adamec |
| 7,274,025 B2 | 9/2007 | Berdermann |
| 7,280,633 B2 | 10/2007 | Cheng |
| 7,297,967 B2 | 11/2007 | Yanagisawa |
| 7,301,162 B2 | 11/2007 | Matsuda |
| 7,307,264 B2 | 12/2007 | Brusasco |
| 7,310,404 B2 | 12/2007 | Tashiro |
| 7,315,606 B2 | 1/2008 | Tsujii |
| 7,319,231 B2 | 1/2008 | Moriyama |
| 7,345,291 B2 | 3/2008 | Kats |
| 7,345,292 B2 | 3/2008 | Moriyama |
| 7,351,988 B2 | 4/2008 | Naumann |
| 7,355,189 B2 | 4/2008 | Yanagisawa |
| 7,356,112 B2 | 4/2008 | Brown |
| 7,368,740 B2 | 5/2008 | Beloussov |
| 7,372,053 B2 | 5/2008 | Yamashita |
| 7,381,979 B2 | 6/2008 | Yamashita |
| 7,385,203 B2 | 6/2008 | Nakayama |
| 7,394,082 B2 | 7/2008 | Fujimaki |
| 7,397,054 B2 | 7/2008 | Natori |
| 7,397,901 B1 | 7/2008 | Johnsen |
| 7,402,822 B2 | 7/2008 | Guertin |
| 7,402,823 B2 | 7/2008 | Guertin |
| 7,402,824 B2 | 7/2008 | Guertin |
| 7,402,963 B2 | 7/2008 | Sliski |
| 7,425,717 B2 | 9/2008 | Matsuda |
| 7,432,516 B2 | 10/2008 | Peggs |
| 7,439,528 B2 | 10/2008 | Nishiuchi |
| 7,446,490 B2 | 11/2008 | Jongen |
| 7,449,701 B2 | 11/2008 | Fujimaki |
| 7,456,415 B2 | 11/2008 | Yanagisawa |
| 7,456,591 B2 | 11/2008 | Jongen |
| 7,465,944 B2 | 12/2008 | Ueno |
| 7,531,818 B2 | 5/2009 | Brahme |
| 7,555,103 B2 | 6/2009 | Johnsen |
| 7,560,717 B2 | 7/2009 | Matsuda |
| 7,576,342 B2 | 8/2009 | Hiramoto |
| 7,586,112 B2 | 9/2009 | Chiba |
| 7,589,334 B2 | 9/2009 | Hiramoto |
| 7,626,347 B2 | 12/2009 | Sliski |
| 7,634,057 B2 | 12/2009 | Ein-Gal |
| 7,659,521 B2 | 2/2010 | Pedroni |
| 7,668,585 B2 | 2/2010 | Green |
| 7,692,168 B2 | 4/2010 | Moriyama |
| 7,701,677 B2 | 4/2010 | Schultz |
| 7,709,818 B2 | 5/2010 | Matsuda |
| 7,718,982 B2 | 5/2010 | Sliski |
| 7,728,311 B2 | 6/2010 | Gall |
| 7,729,469 B2 | 6/2010 | Kobayashi |
| 7,741,623 B2 | 6/2010 | Sommer |
| 7,755,305 B2 | 7/2010 | Umezawa |
| 7,772,577 B2 | 8/2010 | Saito |
| 7,796,730 B2 | 9/2010 | Marash |
| 7,801,277 B2 | 9/2010 | Zou |
| 7,807,982 B2 | 10/2010 | Nishiuchi |
| 7,817,778 B2 | 10/2010 | Nord |
| 7,825,388 B2 | 11/2010 | Nihongi |
| 7,826,593 B2 | 11/2010 | Svensson |
| 7,834,336 B2 | 11/2010 | Boeh |
| 7,838,855 B2 | 11/2010 | Fujii |
| 7,848,488 B2 | 12/2010 | Mansfield |
| 7,860,216 B2 | 12/2010 | Jongen |
| 7,875,868 B2 | 1/2011 | Moriyama |
| 7,894,574 B1 | 2/2011 | Nord |
| 7,906,769 B2 | 3/2011 | Blasche |
| 7,919,765 B2 | 4/2011 | Timmer |
| 7,940,891 B2 | 5/2011 | Star-Lack |
| 7,961,844 B2 | 6/2011 | Takeda |
| 7,977,656 B2 | 7/2011 | Fujimaki |
| 7,982,198 B2 | 7/2011 | Nishiuchi |
| 7,987,053 B2 | 7/2011 | Schaffner |
| 7,995,813 B2 | 8/2011 | Foshee |
| 8,003,964 B2 | 8/2011 | Stark |
| 8,009,804 B2 | 8/2011 | Siljamaki |
| 2003/0163015 A1 | 8/2003 | Yanagisawa |
| 2003/0164459 A1 | 9/2003 | Schardt |
| 2004/0022361 A1 | 2/2004 | Lemaitre |
| 2004/0155206 A1 | 8/2004 | Marchand et al. |
| 2005/0161618 A1 | 7/2005 | Pedroni |
| 2005/0211905 A1 | 9/2005 | Stark |
| 2005/0238134 A1 | 10/2005 | Brusasco |
| 2005/0269497 A1 | 12/2005 | Jongen |
| 2006/0106301 A1 | 5/2006 | Kats |
| 2006/0255285 A1 | 11/2006 | Jongen et al. |
| 2007/0018121 A1 | 1/2007 | Leyman |
| 2007/0093723 A1 | 4/2007 | Keall |
| 2007/0170994 A1 | 7/2007 | Peggs |
| 2008/0023644 A1 | 1/2008 | Pedroni |
| 2008/0093567 A1 | 4/2008 | Gall |
| 2008/0191142 A1 | 8/2008 | Pedroni |
| 2009/0096179 A1 | 4/2009 | Stark |
| 2009/0140672 A1 | 6/2009 | Gall |
| 2009/0168960 A1 | 7/2009 | Jongen |
| 2009/0200483 A1 | 8/2009 | Gall |
| 2009/0236545 A1 | 9/2009 | Timmer |
| 2009/0283704 A1 | 11/2009 | Nishiuchi |
| 2009/0289194 A1 | 11/2009 | Saito |
| 2009/0304153 A1 | 12/2009 | Amelia |
| 2010/0001212 A1 | 1/2010 | Nishiuchi |
| 2010/0008468 A1 | 1/2010 | Balakin |
| 2010/0008469 A1 | 1/2010 | Balakin |
| 2010/0033115 A1 | 2/2010 | Cleland |
| 2010/0045213 A1 | 2/2010 | Sliski |
| 2010/0059688 A1 | 3/2010 | Claereboudt |
| 2010/0060209 A1 | 3/2010 | Balakin |
| 2010/0128846 A1 | 5/2010 | Balakin |
| 2010/0230617 A1 | 9/2010 | Gall |
| 2010/0272241 A1 | 10/2010 | Amelia |
| 2010/0308235 A1 | 12/2010 | Sliski |
| 2011/0073778 A1 | 3/2011 | Natori |

| | | | |
|---|---|---|---|
| 2011/0089329 A1 | 4/2011 | Jongen |
| 2011/0127443 A1 | 6/2011 | Comer |
| 2011/0137159 A1 | 6/2011 | Jongen |
| 2011/0186720 A1 | 8/2011 | Jongen |

FOREIGN PATENT DOCUMENTS

| | | |
|---|---|---|
| WO | WO 2008/044194 A2 | 4/2008 |

OTHER PUBLICATIONS

Adams, "Electrostatic cylinder lenses II: Three Element Einzel Lenses", Journal, Feb. 1, 1972, pp. 150-155, XP002554355, vol. 5 No. 2, Journal of Physics E.

Amaldi, "A Hospital-Based Hadrontherapy Complex", Journal, Jun. 27, 1994, pp. 49-51, XP002552288, Proceedings of Epac 94, London, England.

Arimoto, "A Study of the PRISM-FFAG Magnet", Journal, Oct. 18, 2004,Oct. 22, 2004, pp. 243-245, XP002551810, Proceedings of Cyclotron 2004 Conference, Tokyo, Japan.

Biophysics Group, "Design Construction and First Experiments of a Magnetic Scanning System for Therapy. Radiobiological Experiment on the Radiobiological Action of Carbon, Oxygen and Neon", Book, Jun. 1, 1991, pp. 1-31, XP009121701, vol. GSI-91-18, GSI Report, Darmstadt ,DE.

Blackmore, "Operation of the TRIUMF Proton Therapy Facility", Book, May 12, 1997, pp. 3831-3833, XP010322373, vol. 3, Proceedings of the 1997 Particle Accelerator Conference, NJ, USA.

Bryant, "Proton-Ion Medical Machine Study (PIMMS) Part II", Book, Jul. 27, 2000, p. 23,p. 228,pp. 289-290, XP002551811, European Organisation for Nuclear Research Cern-Ps Division, Geneva, Switzerland.

Craddock, "New Concepts in FFAG Design for Secondary Beam Facilities and other Applications", Journal, May 16, 2005,May 20, 2005, pp. 261-265, XP002551806, Proceedings of 2005 Particle Accelerator Conference, Knoxville, Tennessee, USA.

Dzhelepov, "Use of USSR Proton Accelerators for Medical Purposes", Journal,Jun. 1973, pp. 268-270, vol. ns-2—No. 3, XP002553045, IEEE Transactions on Nuclear Science USA, USA.

Endo, "Medical Synchrotron for Proton Therapy" Journal, Jun. 7, 1988,Jun. 11, 1988, pp. 1459-1461, XP002551808, Proceedings of Epac 88, Rome, Italy.

Johnstone, Koscielniak, "Tune-Stabilized Linear-Field FFAG for Carbon Therapy", Journal, Jun. 26, 2006,Jun. 30, 2006, XP002551807, Proceedings of Epac 2006, Edinburgh, Scotland, UK.

Kalnins, "The use of electric multipole lenses for bending and focusing polar molecules, with application to the design of a rotational-state separator", Journal, May 17, 2003,May 21, 2003, pp. 2951-2953, XP002554356, Proceeding of Pac 2003, Portland, Oregon, USA.

Kim, "50 MeV Proton Beam Test Facility for Low Flux Beam Utilization Studies of PEFP", Journal, Oct. 31, 2005, pp. 441-443, XP002568008, Proceedings of Apac 2004, Pohang, Korea.

Lapostolle, "Introduction a la theorie des accelerateurs lineaires", Book, Jul. 10, 1987, pp. 4-5, XP002554354, Cern Yellow Book Cern, Geneva, Switzerland.

Li, "A thin Beryllium Injection Window for CESR-C", Book, May 12, 2003, pp. 2264-2266, XP002568010, vol. 4, PAC03, Portland, Oregon, USA.

Noda, "Slow beam extraction by a transverse RF field with AM and FM", Journal, May 21, 1996, pp. 269-277, vol. A374, XP002552289, Nuclear Instruments and Methods in Physics Research A, Eslevier, Amsterdam, NL.

Noda, "Performance of a respiration-gated beam control system for patient treatment", Journal, Jun. 10, 1996,Jun. 14, 1996, pp. 2656-2658, XP002552290, Proceedings Epac 96, Barcelona, Spain.

Peters, "Negative ion sources for high energy accelerators", Journal, Feb. 1, 2000, pp. 1069-1074, XP012037926, vol. 71—No. 2,Review of Scientific Instruments, Melville, NY, USA.

Pohlit, "Optimization of Cancer Treatment with Accelerator Produced Radiations", Journal, Jun. 22, 1998, pp. 192-194, XP002552855, Proceedings Epac 98, Stockholm, Sweden.

Saito, "RF Accelerating System for Compact Ion Synchrotron", Journal, Jun. 18, 2001, pp. 966-968, XP002568009, Proceeding of 2001 Pac, Chicago, USA.

Suda, "Medical Application of the Positron Emitter Beam at HIMAC", Journal, Jun. 26, 2000, Jun. 30, 2000, pp. 2554-2556, XP002553046, Proceedings of EPAC 2000, Vienna, Austria.

Tanigaki, "Construction of FFAG Accelerators in KURRI for ADS Study", May 16, 2005,May 20, 2005, pp. 350-352, XP002551809, Proceedings of 2005 Particle Accelerator Conference, Knoxville, Tennessee, USA.

Trbojevic, "Design of a Non-Scaling FFAG Accelerator for Proton Therapy", Journal, Oct. 18, 2004,Oct. 22, 2004, pp. 246-248, XP002551805, Proceedings of 2004 Cyclotron Conference, Tokyo, Japan.

Winkler, "Charge Exchange Extraction at the Experimental Storage Ring ESR at GSI", Journal, Jun. 22, 1998, p. 559-561, XP002552287, Proceedings of Epac 98, Stockholm, Sweden.

* cited by examiner

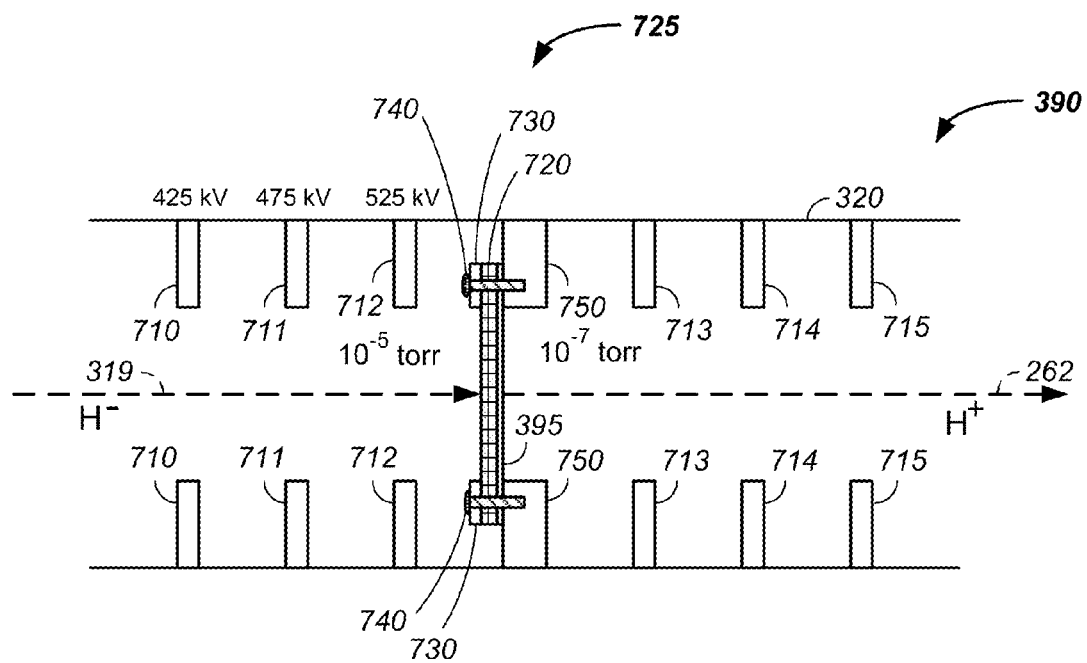
FIG. 7A
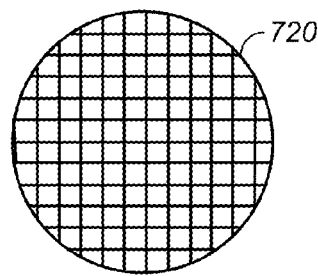
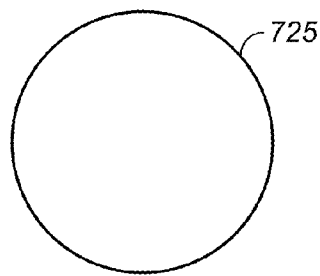
FIG. 7B         FIG. 7C

TANDEM ACCELERATOR METHOD AND APPARATUS USED IN CONJUNCTION WITH A CHARGED PARTICLE CANCER THERAPY SYSTEM

CROSS REFERENCES TO RELATED APPLICATIONS

This application:
is a continuation-in-part of U.S. patent application Ser. No. 12/425,683 filed Apr. 17, 2009 now U.S. Pat. No. 7,939,809, which claims the benefit of:
U.S. provisional patent application No. 61/055,395 filed May 22, 2008;
U.S. provisional patent application No. 61/137,574 filed Aug. 1, 2008;
U.S. provisional patent application No. 61/192,245 filed Sep. 17, 2008;
U.S. provisional patent application No. 61/055,409 filed May 22, 2008;
U.S. provisional patent application No. 61/203,308 filed Dec. 22, 2008;
U.S. provisional patent application No. 61/188,407 filed Aug. 11, 2008;
U.S. provisional patent application No. 61/188,406 filed Aug. 11, 2008;
U.S. provisional patent application No. 61/189,815 filed Aug. 25, 2008;
U.S. provisional patent application No. 61/201,731 filed Dec. 15, 2008;
U.S. provisional patent application No. 61/205,362 filed Jan. 12, 2009;
U.S. provisional patent application No. 61/134,717 filed Jul. 14, 2008;
U.S. provisional patent application No. 61/134,707 filed Jul. 14, 2008;
U.S. provisional patent application No. 61/201,732 filed Dec. 15, 2008;
U.S. provisional patent application No. 61/198,509 filed Nov. 7, 2008;
U.S. provisional patent application No. 61/134,718 filed Jul. 14, 2008;
U.S. provisional patent application No. 61/190,613 filed Sep. 2, 2008;
U.S. provisional patent application No. 61/191,043 filed Sep. 8, 2008;
U.S. provisional patent application No. 61/192,237 filed Sep. 17, 2008;
U.S. provisional patent application No. 61/201,728 filed Dec. 15, 2008;
U.S. provisional patent application No. 61/190,546 filed Sep. 2, 2008;
U.S. provisional patent application No. 61/189,017 filed Aug. 15, 2008;
U.S. provisional patent application No. 61/198,248 filed Nov. 5, 2008;
U.S. provisional patent application No. 61/198,508 filed Nov. 7, 2008;
U.S. provisional patent application No. 61/197,971 filed Nov. 3, 2008;
U.S. provisional patent application No. 61/199,405 filed Nov. 17, 2008;
U.S. provisional patent application No. 61/199,403 filed Nov. 17, 2008; and
U.S. provisional patent application No. 61/199,404 filed Nov. 17, 2008;
claims the benefit of U.S. provisional patent application No. 61/209,529 filed Mar. 9, 2009;
claims the benefit of U.S. provisional patent application No. 61/208,182 filed Feb. 23, 2009;
claims the benefit of U.S. provisional patent application No. 61/208,971 filed Mar. 3, 2009;
claims the benefit of U.S. provisional patent application No. 61/270,298, filed Jul. 7, 2009; and
claims priority to PCT patent application serial No.: PCT/RU2009/00015, filed Mar. 4, 2009,
all of which are incorporated herein in their entirety by this reference thereto.

BACKGROUND OF THE INVENTION

1. Field of the Invention

This invention relates generally to treatment of solid cancers. More particularly, the invention relates to a tandem accelerator system used as part of a ion beam injection system, which is used in conjunction with charged particle cancer therapy beam acceleration, extraction, and/or targeting methods and apparatus.

2. Discussion of the Prior Art

Cancer Treatment

Proton therapy systems typically include: a beam generator, an accelerator, and a beam transport system to move the resulting accelerated protons to a plurality of treatment rooms where the protons are delivered to a tumor in a patient's body.

Proton therapy works by aiming energetic ionizing particles, such as protons accelerated with a particle accelerator, onto a target tumor. These particles damage the DNA of cells, ultimately causing their death. Cancerous cells, because of their high rate of division and their reduced ability to repair damaged DNA, are particularly vulnerable to attack on their DNA.

Due to their relatively enormous size, protons scatter less easily in the tissue and there is very little lateral dispersion. Hence, the proton beam stays focused on the tumor shape without much lateral damage to surrounding tissue. All protons of a given energy have a certain range, defined by the Bragg peak, and the dosage delivery to tissue ratio is maximum over just the last few millimeters of the particle's range. The penetration depth depends on the energy of the particles, which is directly related to the speed to which the particles were accelerated by the proton accelerator. The speed of the proton is adjustable to the maximum rating of the accelerator. It is therefore possible to focus the cell damage due to the proton beam at the very depth in the tissues where the tumor is situated. Tissues situated before the Bragg peak receive some reduced dose and tissues situated after the peak receive none.

Patents related to the current invention are summarized here.

Accelerator/Synchrotron

H. Tanaka, et. al. "Charged Particle Accelerator", U.S. Pat. No. 7,259,529 (Aug. 21, 2007) describe a charged particle accelerator having a two period acceleration process with a fixed magnetic field applied in the first period and a timed second acceleration period to provide compact and high power acceleration of the charged particles.

V. Kulish, et. al. "Inductional Undulative EH-Accelerator", U.S. Pat. No. 6,433,494 (Aug. 13, 2002) describe an inductive undulative EH-accelerator for acceleration of beams of charged particles. The device consists of an electromagnet undulation system, whose driving system for electromagnets is made in the form of a radio-frequency (RF) oscillator operating in the frequency range from about 100 KHz to 10 GHz.

K. Saito, et. al. "Radio-Frequency Accelerating System and Ring Type Accelerator Provided with the Same", U.S. Pat. No. 5,917,293 (Jun. 29, 1999) describe a radio-frequency accelerating system having a loop antenna coupled to a magnetic core group and impedance adjusting means connected to the loop antenna. A relatively low voltage is applied to the impedance adjusting means allowing small construction of the adjusting means.

J. Hirota, et. al. "Ion Beam Accelerating Device Having Separately Excited Magnetic Cores", U.S. Pat. No. 5,661,366 (Aug. 26, 1997) describe an ion beam accelerating device having a plurality of high frequency magnetic field inducing units and magnetic cores.

J. Hirota, et. al. "Acceleration Device for Charged Particles", U.S. Pat. No. 5,168,241 (Dec. 1, 1992) describe an acceleration cavity having a high frequency power source and a looped conductor operating under a control that combine to control a coupling constant and/or de-tuning allowing transmission of power more efficiently to the particles.

Vacuum Chamber

T. Kobari, et. al. "Apparatus For Treating the Inner Surface of Vacuum Chamber", U.S. Pat. No. 5,820,320 (Oct. 13, 1998) and T. Kobari, et. al. "Process and Apparatus for Treating Inner Surface Treatment of Chamber and Vacuum Chamber", U.S. Pat. No. 5,626,682 (May 6, 1997) both describe an apparatus for treating an inner surface of a vacuum chamber including means for supplying an inert gas or nitrogen to a surface of the vacuum chamber with a broach. Alternatively, the broach is used for supplying a lower alcohol to the vacuum chamber for dissolving contaminants on the surface of the vacuum chamber.

Problem

There exists in the art of particle beam therapy of cancerous tumors a need for a tandem accelerator operating efficiently with a partial vacuum system of a negative ion beam source vacuum. There further exists in the art a need for extracting the negative ion, focusing the negative ion, converting the negative ion into a positive ion, and injecting the positive ion into a synchrotron. There further exists in the art of particle beam treatment of cancerous tumors in the body a need for reduced synchrotron power supply requirements, reduced synchrotron size, and control of synchrotron magnetic fields. Still further, there exists a need in the art to control the charged particle cancer therapy system in terms of specified energy, intensity, and/or timing of charged particle delivery. Yet still further, there exists a need for efficient, precise, and/or accurate noninvasive, in-vivo treatment of a solid cancerous tumor with minimization of damage to surrounding healthy tissue in a patient.

SUMMARY OF THE INVENTION

The invention comprises a tandem accelerator method and apparatus used as part of an ion beam injection system, which is part of a charged particle cancer therapy beam system.

DESCRIPTION OF THE FIGURES

FIG. 7 illustrates a negative ion beam path vacuum system.

DETAILED DESCRIPTION OF THE INVENTION

Figure 1:
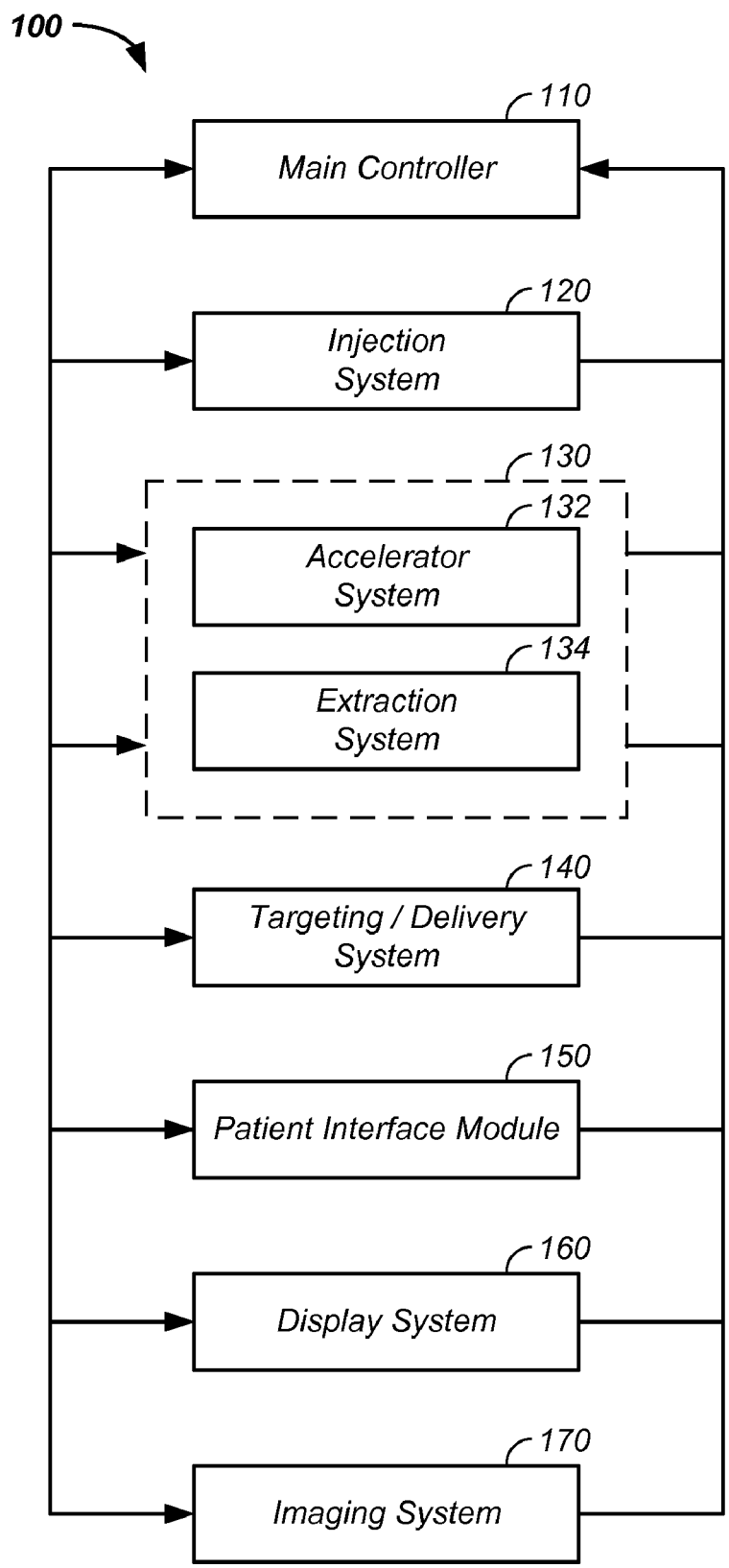
FIG. 1 illustrates component connections of a particle beam therapy system.

The invention relates generally to treatment of solid cancers. More particularly, the invention relates to a tandem accelerator operating to enhance efficiency of a negative ion source vacuum system, which is part of an ion beam injection system used in conjunction with charged particle cancer therapy beam injection, acceleration, extraction, and/or targeting methods and apparatus.

Novel design features of a synchrotron are described. Particularly, a negative ion beam source with novel features in the negative ion source, ion source vacuum system, ion beam focusing lens, and tandem accelerator are described. Additionally, turning magnets, edge focusing magnets, magnetic field concentration magnets, winding and correction coils, flat magnetic field incident surfaces, and extraction elements are described that minimize the overall size of the synchrotron, provide a tightly controlled proton beam, directly reduce the size of required magnetic fields, directly reduce required operating power, and allow continual acceleration of protons in a synchrotron even during a process of extracting protons from the synchrotron. The ion beam source system and synchrotron are preferably computer integrated with a patient imaging system and a patient interface including respiration monitoring sensors and patient positioning elements.

Used in conjunction with the injection system, an imaging system, respiration sensors, and novel features of a synchrotron are described. Particularly, intensity control of a charged particle beam acceleration, extraction, and/or targeting method and apparatus used in conjunction with charged particle beam radiation therapy of cancerous tumors are described. More particularly, intensity and energy control of a charged particle stream of a synchrotron is described where the synchrotron includes any of: turning magnets, edge focusing magnets, concentrating magnetic field magnets, winding and control coils, and extraction elements. The synchrotron control elements allow tight control of the charged particle beam, which compliments the tight control of patient positioning to yield efficient treatment of a solid tumor with reduced tissue damage to surrounding healthy tissue. In addition, the system reduces the overall size of the synchrotron, provides a tightly controlled proton beam, directly reduces the size of required magnetic fields, directly reduces required operating power, and allows continual acceleration of protons in a synchrotron even during a process of extracting protons from the synchrotron.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system. Any of the charged particle techniques described herein are equally applicable to any charged particle beam system.

Referring now to FIG. 1, a charged particle beam system 100 is illustrated. The charged particle beam preferably comprises a number of subsystems including any of: a main controller 110; an injection system 120; a synchrotron 130 that typically includes: (1) an accelerator system 132 and (2) an extraction system 134; a scanning/targeting/delivery system 140; a patient interface module 150; a display system 160; and/or an imaging system 170.

An exemplary method of use of the charged particle beam system 100 is provided. The main controller 110 controls one or more of the subsystems to accurately and precisely deliver protons to a tumor of a patient. For example, the main controller 110 obtains an image, such as a portion of a body and/or of a tumor, from the imaging system 170. The main controller 110 also obtains position and/or timing information from the patient interface module 150. The main controller 110 then optionally controls the injection system 120 to inject a proton into a synchrotron 130. The synchrotron typically contains at least an accelerator system 132 and an extraction system 134. The main controller preferably controls the proton beam within the accelerator system, such as by controlling speed, trajectory, and timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the scanning/targeting/delivery system 140 to the patient interface module 150. One or more components of the patient interface module 150 are preferably controlled by the main controller 110. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

Synchrotron

Herein, the term synchrotron is used to refer to a system maintaining the charged particle beam in a circulating path. Further, the charged particle beam is referred to herein as circulating along a circulating path about a central point of the synchrotron. The circulating path is alternatively referred to as an orbiting path; however, the orbiting path does not refer to a perfect circle or ellipse, rather it refers to cycling of the protons around a central point or region.

Figure 2:
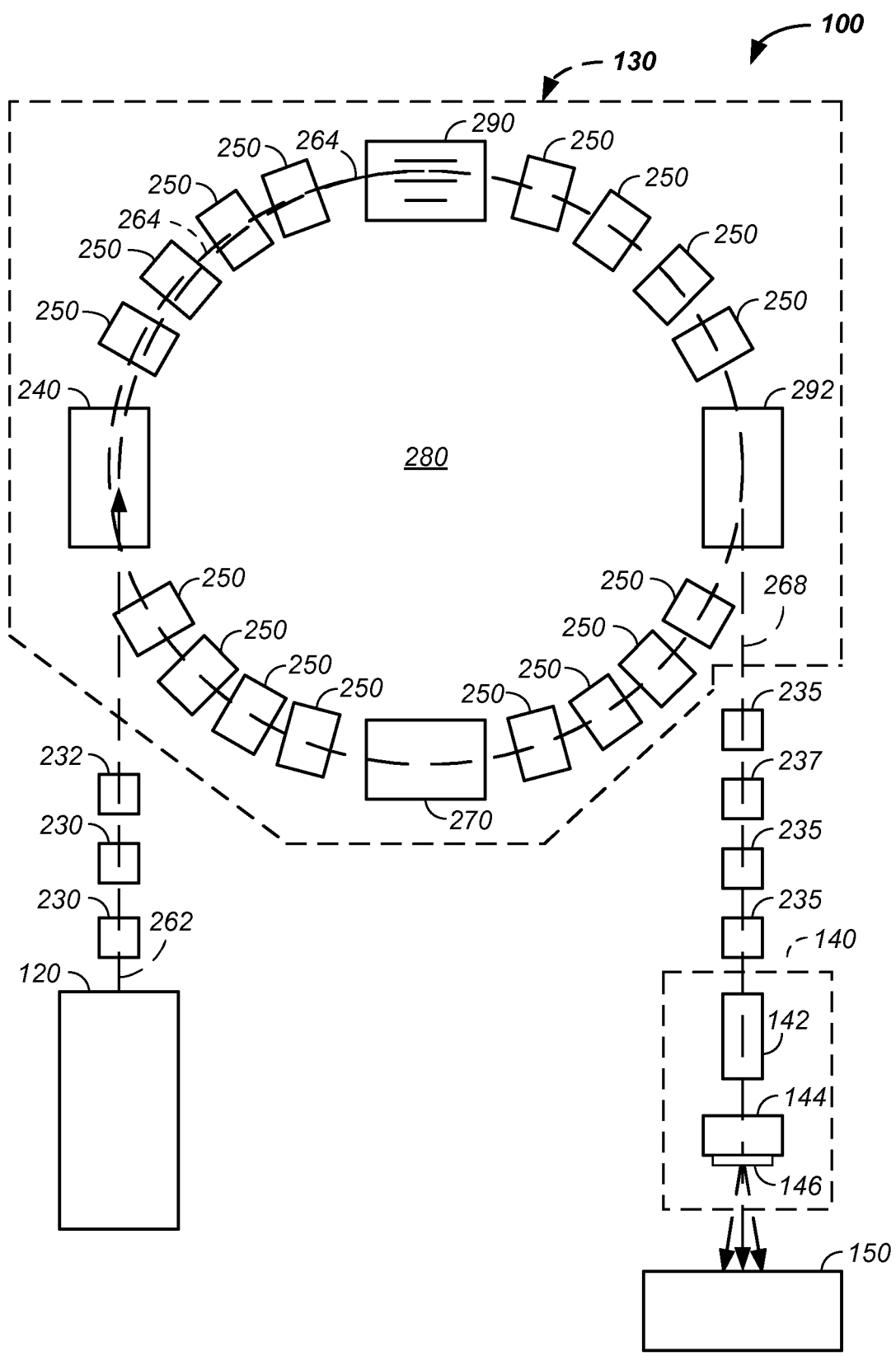
FIG. 2 illustrates a charged particle therapy system.

Referring now to FIG. 2, an illustrative exemplary embodiment of one version of the charged particle beam system 100 is provided. The number, position, and described type of components is illustrative and non-limiting in nature. In the illustrated embodiment, an injector system 120 or ion source or charged particle beam source generates protons. The protons are delivered into a vacuum tube that runs into, through, and out of the synchrotron. The generated protons are delivered along an initial path 262. Focusing magnets 230, such as quadrupole magnets or injection quadrupole magnets, are used to focus the proton beam path. A quadrupole magnet is a focusing magnet. An injector bending magnet 232 bends the proton beam toward the plane of the synchrotron 130. The focused protons having an initial energy are introduced into an injector magnet 240, which is preferably an injection Lamberson magnet. Typically, the initial beam path 262 is along an axis off of, such as above, a circulating plane of the synchrotron 130. The injector bending magnet 232 and injector magnet 240 combine to move the protons into the synchrotron 130. Main bending magnets, turning magnets 250, or dipole magnets or circulating magnets are used to turn the protons along a circulating beam path 264. A dipole magnet is a bending magnet. The main bending magnets 250 bend the initial beam path 262 into a circulating beam path 264. In this example, the main bending magnets 250 or circulating magnets are represented as four sets of four magnets to maintain the circulating beam path 264 into a stable circulating beam path. However, any number of magnets or sets of magnets are optionally used to move the protons around a single orbit in the circulation process. The protons pass through an accelerator 270. The accelerator accelerates the protons in the circulating beam path 264. As the protons are accelerated, the fields applied by the magnets are increased. Particularly, the speed of the protons achieved by the accelerator 270 are synchronized with magnetic fields of the main bending magnets 250 or circulating magnets to maintain stable circulation of the protons about a central point or region 280 of the synchrotron. At separate points in time the accelerator 270/main bending magnet 250 combination is used to accelerate and/or decelerate the circulating protons while maintaining the protons in the circulating path or orbit. An extraction element of the inflector/deflector system 290 is used in combination with a Lamberson extraction magnet 292 to remove protons from their circulating beam path 264 within the synchrotron 130. One example of a deflector component is a Lamberson magnet. Typically the deflector moves the protons from the circulating plane to an axis off of the circulating plane, such as above the circulating plane. Extracted protons are preferably directed and/or focused using an extraction bending magnet 237 and extraction focusing magnets 235, such as quadrupole magnets along a transport path 268 into the scanning/targeting/delivery system 140. Two components of a scanning system 140 or targeting system typically include a first axis control 142, such as a vertical control, and a second axis control 144, such as a horizontal control. A nozzle system 146 is used for imaging the proton beam and/or as a vacuum barrier between the low pressure beam path of the synchrotron and the atmosphere. Protons are delivered with control to the patient interface module 150 and to a tumor of a patient. All of the above listed elements are optional and may be used in various permutations and combinations.

Ion Beam Generation System

An ion beam generation system generates a negative ion beam, such as a hydrogen anion or H⁻ beam; preferably focuses the negative ion beam; converts the negative ion beam to a positive ion beam, such as a proton or H⁺ beam; and injects the positive ion beam into the synchrotron 130. Portions of the ion beam path are preferably under partial vacuum. Each of these systems are further described, infra.

Figure 3:
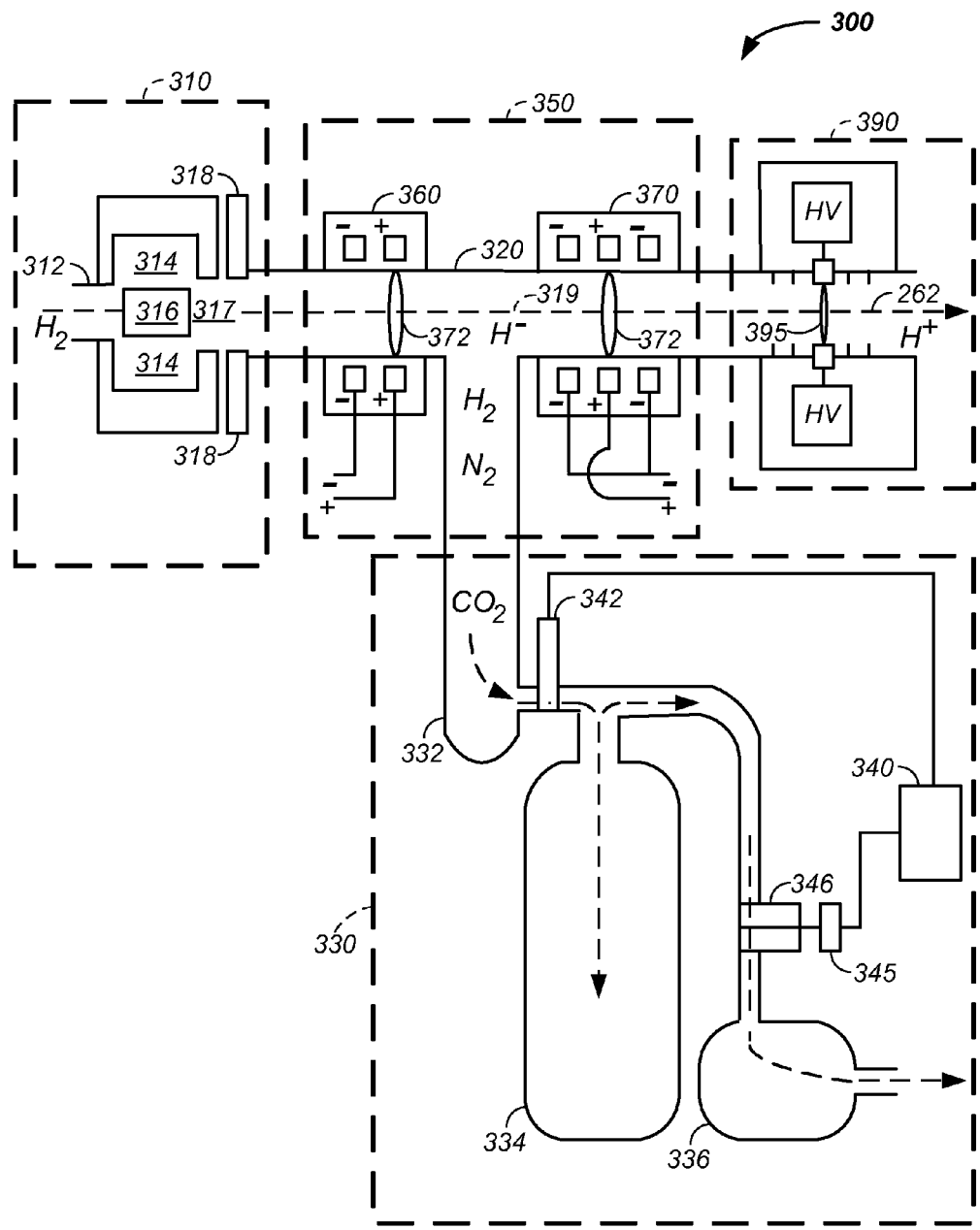
FIG. 3 illustrates an ion beam generation system.

Referring now to FIG. 3, an exemplary ion beam generation system 300 is illustrated. As illustrated, the ion beam generation system 300 has four major elements: a negative ion source 310, a first partial vacuum system 330, an optional ion beam focusing system 350, and a tandem accelerator 390.

Still referring to FIG. 3, the negative ion source 310 preferably includes an inlet port 312 for injection of hydrogen gas into a high temperature plasma chamber 314. In one embodiment, the plasma chamber includes a magnetic material 316, which provides a magnetic field barrier 317 between the high temperature plasma chamber 314 and a low temperature plasma region on the opposite side of the magnetic field barrier. An extraction pulse is applied to a negative ion extraction electrode 318 to pull the negative ion beam into a negative ion beam path 319, which proceeds through the first partial vacuum system 330, through the ion beam focusing system 350, and into the tandem accelerator 390.

Still referring to FIG. 3, the first partial vacuum system 330 is an enclosed system running from the hydrogen gas inlet port 312 to the tandem accelerator 390 foil 395. The foil 395 is sealed directly or indirectly to the edges of the vacuum tube 320 providing for a higher pressure, such as about $10^{-5}$ torr, to be maintained on the first partial vacuum system 330 side of the foil 395 and a lower pressure, such as about $10^{-7}$ torr, to be maintained on the synchrotron side of the foil 390. By only pumping first partial vacuum system 330 and by only semi-continuously operating the ion beam source vacuum based on sensor readings, the lifetime of the semi-continuously operating pump is extended. The sensor readings are further described, infra.

Still referring to FIG. 3, the first partial vacuum system 330 preferably includes: a first pump 332, such as a continuously operating pump and/or a turbo molecular pump; a large holding volume 334; and a semi-continuously operating pump 336. Preferably, a pump controller 340 receives a signal from a pressure sensor 342 monitoring pressure in the large holding volume 334. Upon a signal representative of a sufficient pressure in the large holding volume 334, the pump controller 340 instructs an actuator 345 to open a valve 346 between the large holding volume and the semi-continuously operating pump 336 and instructs the semi-continuously operating pump to turn on and pump to atmosphere residual gases out of the vacuum line 320 about the charged particle stream. In this fashion, the lifetime of the semi-continuously operating pump is extended by only operating semi-continuously and as needed. In one example, the semi-continuously operating pump 336 operates for a few minutes every few hours, such as 5 minutes every 4 hours, thereby extending a pump with a lifetime of about 2,000 hours to about 96,000 hours.

Further, by isolating the inlet gas from the synchrotron vacuum system, the synchrotron vacuum pumps, such as turbo molecular pumps can operate over a longer lifetime as the synchrotron vacuum pumps have fewer gas molecules to deal with. For example, the inlet gas is primarily hydrogen gas but may contain impurities, such as nitrogen and carbon dioxide. By isolating the inlet gases in the negative ion source system 310, first partial vacuum system 330, ion beam focusing system 350 and negative ion beam side of the tandem accelerator 390, the synchrotron vacuum pumps can operate at lower pressures with longer lifetimes, which increases the efficiency of the synchrotron 130.

Still referring to FIG. 3, the ion beam focusing system 350 includes two or more electrodes where one electrode of each electrode pair partially obstructs the ion beam path with conductive paths 372, such as a conductive mesh. In the illustrated example, two ion beam focusing system sections are illustrated, a two electrode ion focusing section 360 and a three electrode ion focusing section 370. In a given electrode pair, electric field lines, running between the conductive mesh of a first electrode and a second electrode, provide inward forces focusing the negative ion beam. Multiple such electrode pairs provide multiple negative ion beam focusing regions. Preferably the two electrode ion focusing section 360, a first three electrode ion focusing section 370, and a second three electrode ion focusing section are placed after the negative ion source and before the tandem accelerator and/or cover a space of about 0.5, 1, or 2 meters along the ion beam path 319. Ion beam focusing systems are further described, infra.

Still referring to FIG. 3, the tandem accelerator 390 preferably includes a foil 395, such as a carbon foil. The negative ions in the negative ion beam path 319 are converted to positive ions, such as protons, and the initial ion beam path 262 results. The foil 395 is preferably sealed directly or indirectly to the edges of the vacuum tube 320 providing for a higher pressure, such as about $10^{-5}$ torr, to be maintained on the side of the foil 395 having the negative ion beam path 319 and a lower pressure, such as about $10^{-7}$ torr, to be maintained on the side of the foil 390 having the proton ion beam path 262. Having the foil 395 physically separating the vacuum chamber 320 into two pressure regions allows for a system having fewer and/or smaller pumps to maintain the lower pressure system in the synchrotron 130 as the inlet hydrogen and its residuals are extracted in a separate contained and isolated space by the first partial vacuum system 330.

Negative Ion Source

Figure 4:
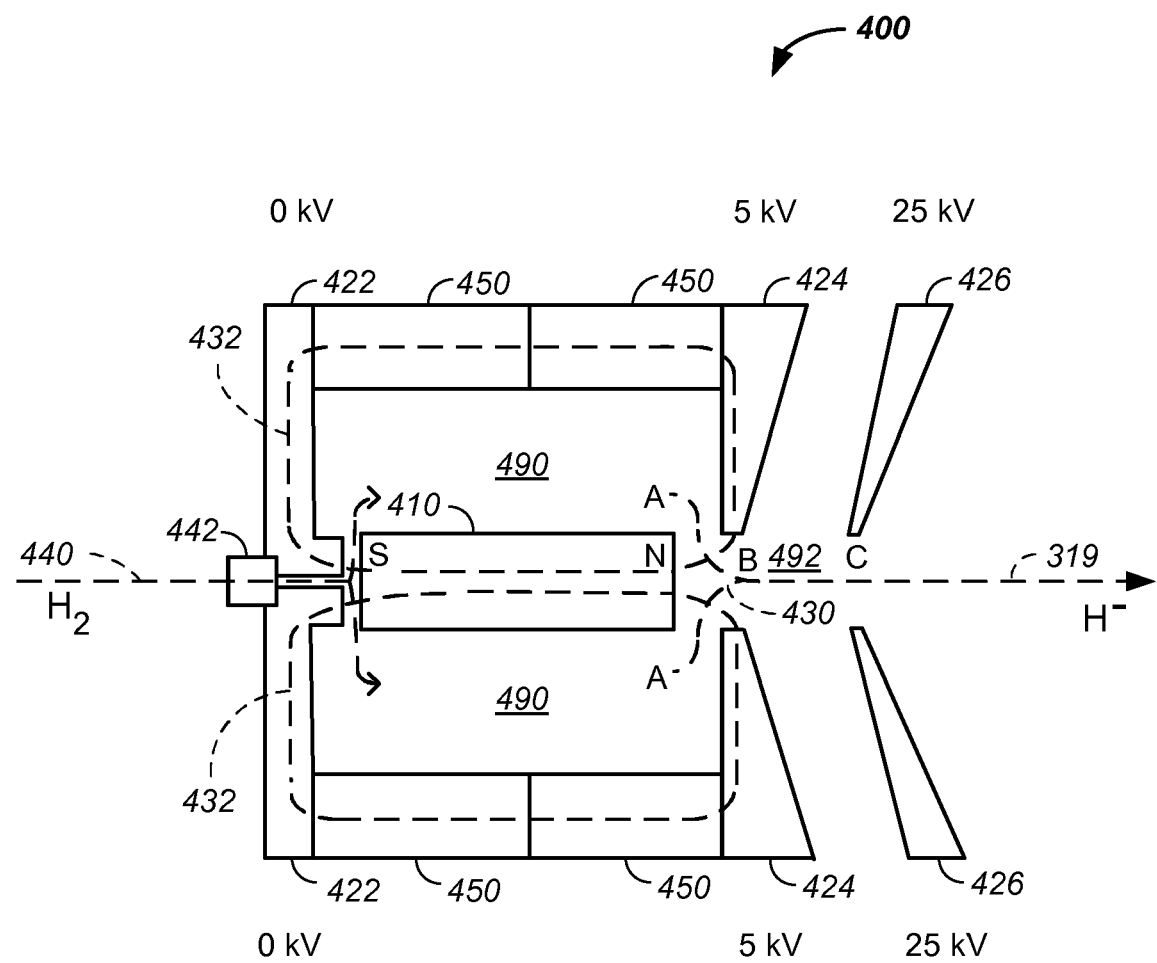
FIG. 4 illustrates a negative ion beam source.

An example of the negative ion source 310 is further described herein. Referring now to FIG. 4, a cross-section of an exemplary negative ion source system 400 is provided. The negative ion beam 319 is created in multiple stages. During a first stage, hydrogen gas is injected into a chamber. During a second stage, a negative ion is created by application of a first high voltage pulse, which creates a plasma about the hydrogen gas to create negative ions. During a third stage, a magnetic field filter is applied to components of the plasma. During a fourth stage, the negative ions are extracted from a low temperature plasma region, on the opposite side of the magnetic field barrier, by application of a second high voltage pulse. Each of the four stages are further described, infra. While the chamber is illustrated as a cross-section of a cylinder, the cylinder is exemplary only and any geometry applies to the magnetic loop containment walls, described infra.

In the first stage, hydrogen gas is injected through the inlet port 312 into a high temperature plasma region 490. The injection port 442 is open for a short period of time, such as less than about 1, 5, or 10 microseconds to minimize vacuum pump requirements to maintain vacuum chamber 320 requirements. The high temperature plasma region is maintained at reduced pressure by the partial vacuum system 330. The injection of the hydrogen gas is optionally controlled by the main controller 110, which is responsive to imaging system 170 information and patient interface module 150 information, such as patient positioning and period in a respiration cycle.

In the second stage, a high temperature plasma region is created by applying a first high voltage pulse across a first electrode 422 and a second electrode 424. For example a 5 kV pulse is applied for about 20 microseconds with 5 kV at the second electrode 424 and about 0 kV applied at the first electrode 422. Hydrogen in the chamber is broken, in the high temperature plasma region 490, into component parts, such as any of: atomic hydrogen, $H^0$, a proton, $H^+$, an electron, $e^-$, a hydrogen anion, and $H^-$.

In the third stage, the high temperature plasma region 490 is at least partially separated from a low temperature plasma region 492 by a magnetic field or magnetic field barrier 430. High energy electrons are restricted from passing through the magnetic field barrier 430. In this manner, the magnetic field barrier 430 acts as a filter between, zone A and zone B, in the negative ion source. Preferably, a central magnetic material 410 is placed within the high temperature plasma region 490, such as along a central axis of the high temperature plasma region 490. Preferably, the first electrode 422 and second electrode 424 are composed of magnetic materials, such as iron. Preferably, the outer walls 450 of the high temperature plasma region, such as cylinder walls, are composed of a magnetic material, such as a permanent magnet, ferric, or iron based material, or a ferrite dielectric ring magnet. In this manner a magnetic field loop is created by: the central magnetic material 410, first electrode 422, the outer walls 450, the second electrode 424, and the magnetic field barrier 430. Again, the magnetic field barrier 430 restricts high energy electrons from passing through the magnetic field barrier 430. Low energy electrons interact with atomic hydrogen, $H^0$, to create a hydrogen anion, $H^-$, in the low temperature plasma region 492.

In the fourth stage, a second high voltage pulse or extraction pulse is applied at a third electrode 426. The second high voltage pulse is preferentially applied during the later period of application of the first high voltage pulse. For example, an extraction pulse of about 25 kV is applied for about the last 5 microseconds of the first creation pulse of about 20 microseconds. The potential difference, of about 20 kV, between the third electrode 426 and second electrode 424 extracts the negative ion, $H^-$, from the low temperature plasma region 492 and initiates the negative ion beam 390, from zone B to zone C.

The magnetic field barrier 430 is optionally created in number of ways. An example of creation of the magnetic field barrier 430 using coils is provided. In this example, the elements described, supra, in relation to FIG. 4 are maintained with several differences. First, the magnetic field is created using coils. An isolating material is preferably provided between the first electrode 422 and the cylinder walls 450 as well as between the second electrode 424 and the cylinder walls 450. The central material 410 and/or cylinder walls 450 are optionally metallic. In this manner, the coils create a magnetic field loop through the first electrode 422, isolating material, outer walls 450, second electrode 424, magnetic field barrier 430, and the central material 410. Essentially, the coils generate a magnetic field in place of production of the magnetic field by the magnetic material 410. The magnetic field barrier 430 operates as described, supra. Generally, any manner that creates the magnetic field barrier 430 between the high temperature plasma region 490 and low temperature plasma region 492 is functionally applicable to the ion beam extraction system 400.

Ion Beam Focusing System

Figure 5:
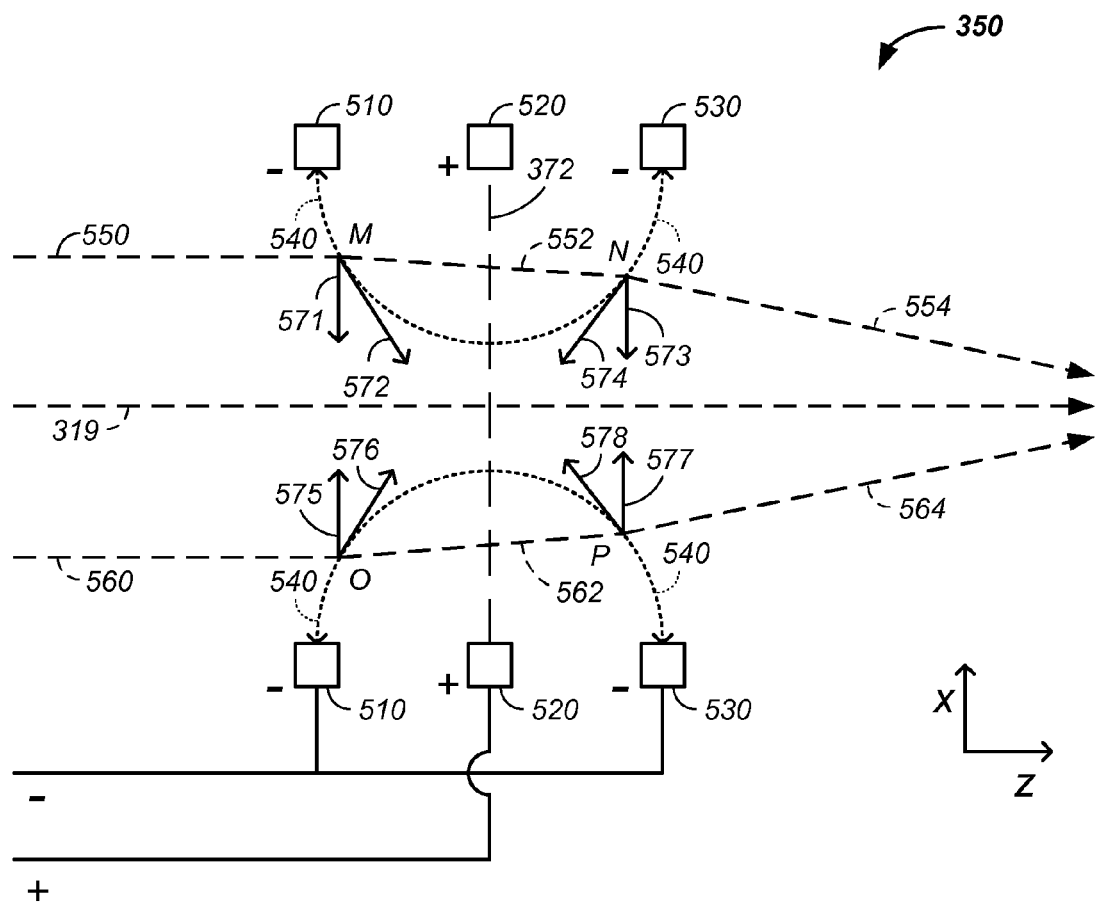
FIG. 5 illustrates an ion beam focusing system.
Figure 6A:
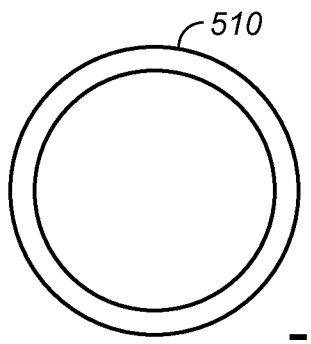
FIGS. 6 A-D illustrate electrodes about a negative ion beam path.
Figure 6B:
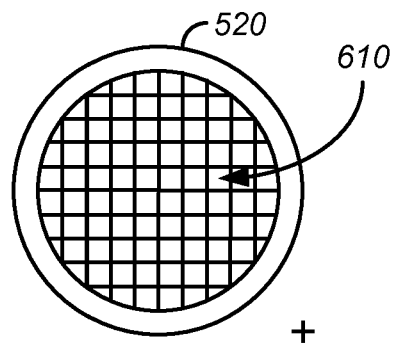
Figure 6C:
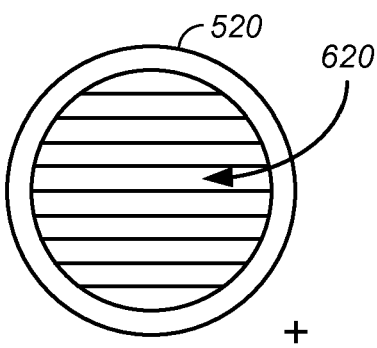
Figure 6D:
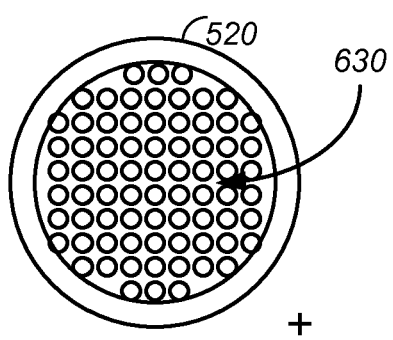

Referring now to FIG. 5, the ion beam focusing system 350 is further described. In this example, three electrodes are used. In this example, the first electrode 510 and third electrode 530 are both negatively charged and each is a ring electrode circumferentially enclosing or at least partially enclosing the negative ion beam path 319. The second electrode 520 is positively charged and is also a ring electrode circumferentially enclosing the negative ion beam path. In addition, the second electrode includes one or more conducting paths 372 running through the negative ion beam path 319. For example, the conducting paths are a wire mesh, a conducting grid, or a series of substantially parallel conducting lines running across the second electrode. In use, electric field lines run from the conducting paths of the positively charged electrode to the negatively charged electrodes. For example, in use the electric field lines 540 run from the conducting paths 372 in the negative ion beam path 319 to the negatively charged electrodes 510, 530. Two ray trace lines 550, 560 of the negative ion beam path are used to illustrate focusing forces. In the first ray trace line 550, the negative ion beam encounters a first electric field line at point M. Negatively charged ions in the negative ion beam 550 encounter forces running up the electric field line 571, illustrated with an x-axis component vector 572. The x-axis component force vectors 572 alters the trajectory of the first ray trace line to a inward focused vector 552, which encounters a second electric field line at point N. Again, the negative ion beam 552 encounters forces running up the electric field line 573, illustrated as having an inward force vector with an x-axis component 574, which alters the inward focused vector 552 to a more inward focused vector 554. Similarly, in the second ray trace line 560, the negative ion beam encounters a first electric field line at point O. Negatively charged ions in the negative ion beam encounter forces running up the electric field line 575, illustrated as having a force vector with an x-axis force 576. The inward force vectors 576 alters the trajectory of the second ray trace line 560 to an inward focused vector 562, which encounters a second electric field line at point P. Again, the negative ion beam encounters forces running up the electric field line 577, illustrated as having force vector with an x-axis component 578, which alters the inward focused vector 562 to a more inward focused vector 564. The net result is a focusing effect on the negative ion beam. Each of the force vectors 572, 574, 576, 578 optionally has x and/or y force vector components resulting in a 3-dimensional focusing of the negative ion beam path. Naturally, the force vectors are illustrative in nature, many electric field lines are encountered, and the focusing effect is observed at each encounter resulting in integral focusing. The example is used to illustrate the focusing effect.

Still referring to FIG. 5, optionally any number of electrodes are used, such as 2, 3, 4, 5, 6, 7, 8, or 9 electrodes, to focus the negative ion beam path where every other electrode, in a given focusing section, is either positively or negatively charged. For example, three focusing sections are optionally used. In the first ion focusing section 360, a pair of electrodes are used where the first electrode encountered along the negative ion beam path is negatively charged and the second electrode is positively charged, resulting in focusing of the negative ion beam path. In the second ion focusing section 370, two pairs of electrodes are used, where a common positively charged electrode with a conductive mesh running through the negatively ion beam path 319 is used. Thus, in the second ion focusing section 370, the first electrode encountered along the negative ion beam path is negatively charged and the second electrode is positively charged, resulting in focusing of the negative ion beam path. Further, in the second ion focusing section, moving along the negative ion beam path, a second focusing effect is observed between the second positively charged electrode and a third negatively charged electrode. In this example, a third ion focusing section is optionally used that again has three electrodes, which acts in the fashion of the second ion focusing section, describe supra.

Referring now to FIG. 6, the central regions of the electrodes in the ion beam focusing system 350 are further described. Referring now to FIG. 6A, the central region of the negatively charged ring electrode 510 is preferably void of conductive material. Referring now to FIGS. 6B-D, the central region of positively charged electrode ring 520 preferably contains conductive paths 372. Preferably, the conductive paths 372 or conductive material within the positively charged electrode ring 520 blocks about 1, 2, 5, or 10 percent of the area and more preferably blocks about 5 percent of the cross-sectional area of the negative ion beam path 319. Referring now to FIG. 6B, one option is a conductive mesh 610. Referring now to FIG. 6C, a second option is a series of conductive lines 620 running substantially in parallel across the positively charged electrode ring 520 that surrounds a portion of the negative ion beam path 319. Referring now to FIG. 6D, a third option is to have a foil 630 or metallic layer cover all of the cross-sectional area of the negative ion beam path with holes punched through the material, where the holes take up about 90-99 percent and more preferably about 95 percent of the area of the foil. More generally, the pair of electrodes are configure to provide electric field lines that provide focusing force vectors to the negative ion beam when the ions in the negative ion beam translate through the electric field lines, as described supra.

In an example of a two electrode negative beam ion focusing system having a first cross-sectional diameter, $d_1$, the negative ions are focused using the two electrode system to a second cross-sectional diameter, $d_2$, where $d_1 > d_2$. Similarly, in an example of a three electrode negative beam ion focusing system having a first cross-sectional diameter, $d_1$, the negative ions are focused using the three electrode system to a third cross-sectional diameter, $d_3$, where $d_1 > d_3$. For like potentials on the electrodes, the three electrode system provides tighter or stronger focusing compared to the two-electrode system, $d_3 < d_2$.

In the examples provided, supra, of a multi-electrode ion beam focusing system, the electrodes are rings. More generally, the electrodes are of any geometry sufficient to provide electric field lines that provide focusing force vectors to the negative ion beam when the ions in the negative ion beam translate through the electric field lines, as described supra. For example, one negative ring electrode is optionally replaced by a number of negatively charged electrodes, such as about 2, 3, 4, 6, 8, 10, or more electrodes placed about the outer region of a cross-sectional area of the negative ion beam probe. Generally, more electrodes are required to converge or diverge a faster or higher energy beam.

In another embodiment, by reversing the polarity of electrodes in the above example, the negative ion beam is made to diverge. Thus, the negative ion beam path is optionally focused and expanded using combinations of electrode pairs. For example, if the electrode having the mesh across the negative ion beam path is made negative, then the negative ion beam path is made to defocus. Hence, combinations of electrode pairs are used for focusing and defocusing a negative ion beam path, such as where a first pair includes a positively charged mesh for focusing and a where a second pair includes a negatively charged mesh for defocusing.

Tandem Accelerator

Referring now to FIG. 7A, the tandem accelerator 390 is further described. The tandem accelerator accelerates ions using a series of electrodes 710, 711, 712, 713, 714, 715. For example, negative ions, such as H⁻, in the negative ion beam path are accelerated using a series of electrodes having progressively higher voltages relative to the voltage of the extraction electrode 426, or third electrode 426, of the negative ion beam source 310. For instance, the tandem accelerator 390 optionally has electrodes ranging from the 25 kV of the extraction electrode 426 to about 525 kV near the foil 395 in the tandem accelerator 390. Upon passing through the foil, the negative ion, H⁻, loses two electrons to yield a proton, H⁺, according to equation 1.

$$H^- \rightarrow H^+ + 2e^- \qquad \text{(eq. 1)}$$

The proton is further accelerated in the tandem accelerator using appropriate voltages at a multitude of further electrodes 713, 714, 715. The protons are then injected into the synchrotron 130 as described, supra.

Still referring to FIG. 7, the foil 395 in the tandem accelerator 390 is further described. The foil 395 is preferably a very thin carbon film of about 30 to 200 angstroms in thickness. The foil thickness is designed to both: (1) not block the ion beam and (2) allow the transfer of electrons yielding protons to form the proton beam path 262. The foil 395 is preferably substantially in contact with a support layer 720, such as a support grid. The support layer 720 provides mechanical strength to the foil 395 to combine to form a vacuum blocking element 725. The foil 395 blocks nitrogen, carbon dioxide, hydrogen, and other gases from passing and thus acts as a vacuum barrier. In one embodiment, the foil 395 is preferably sealed directly or indirectly to the edges of the vacuum tube 320 providing for a higher pressure, such as about $10^{-5}$ torr, to be maintained on the side of the foil 395 having the negative ion beam path 319 and a lower pressure, such as about $10^{-7}$ torr, to be maintained on the side of the foil 395 having the proton ion beam path 262. Having the foil 395 physically separating the vacuum chamber 320 into two pressure regions allows for a vacuum system having fewer and/or smaller pumps to maintain the lower pressure system in the synchrotron 130 as the inlet hydrogen and its residuals are extracted in a separate contained and isolated space by the first partial vacuum system 330. The foil 395 and support layer 720 are preferably attached to the structure 750 of the tandem accelerator 390 or vacuum tube 320 to form a pressure barrier using any mechanical means, such as a metal, plastic, or ceramic ring 730 compressed to the walls with an attachment screw 740. Any mechanical means for separating and sealing the two vacuum chamber sides with the foil 395 are equally applicable to this system. Referring now to FIG. 7B, the support structure 720 and foil 395 are individually viewed in the x-, y-plane.

Figure 8:
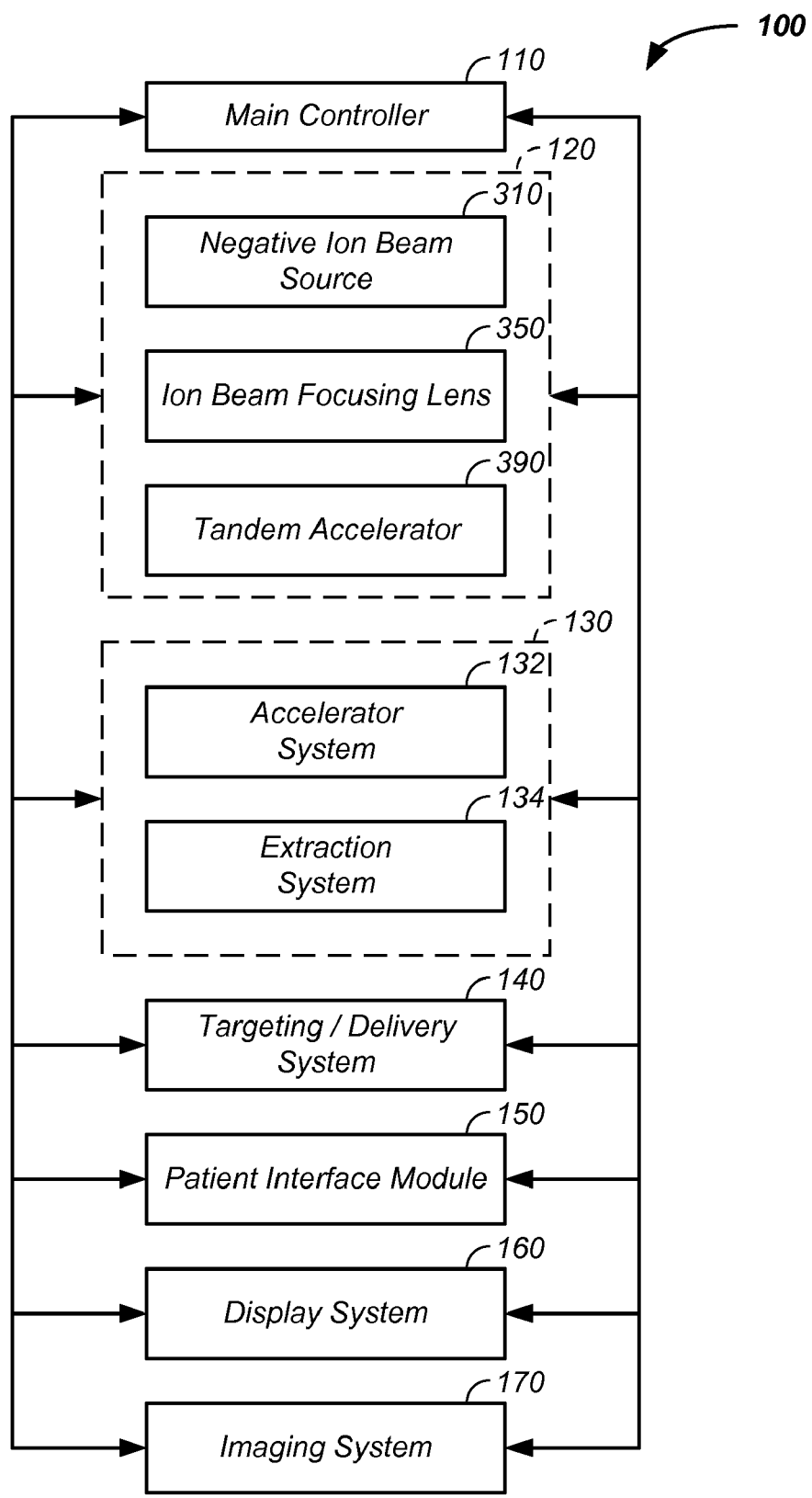
FIG. 8 is a synchrotron control flowchart.

Referring now to FIG. 8, another exemplary method of use of the charged particle beam system 100 is provided. The main controller 110, or one or more sub-controllers, controls one or more of the subsystems to accurately and precisely deliver protons to a tumor of a patient. For example, the main controller sends a message to the patient indicating when or how to breathe. The main controller 110 obtains a sensor reading from the patient interface module, such as a temperature respiration sensor or a force reading indicative of where in a respiration cycle the subject is. The main controller collects an image, such as a portion of a body and/or of a tumor, from the imaging system 170. The main controller 110 also obtains position and/or timing information from the patient interface module 150. The main controller 110 then optionally controls the injection system 120 to inject hydrogen gas into a negative ion beam source 310 and controls timing of extraction of the negative ion from the negative ion beam source 310. Optionally, the main controller controls ion beam focusing the ion beam focusing lens system 350; acceleration of the proton beam with the tandem accelerator 390; and/or injection of the proton into the synchrotron 130. The synchrotron typically contains at least an accelerator system 132 and an extraction system 134. The synchrotron preferably contains one or more of: turning magnets, edge focusing magnets, magnetic field concentration magnets, winding and correction coils, and flat magnetic field incident surfaces, some of which contain elements under control by the main controller 110. The main controller preferably controls the proton beam within the accelerator system, such as by controlling speed, trajectory, and/or timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the targeting/delivery system 140 to the patient interface module 150. One or more components of the patient interface module 150 are preferably controlled by the main controller 110, such as vertical position of the patient, rotational position of the patient, and patient chair positioning/stabilization/control elements. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the patient.

Circulating System

A synchrotron 130 preferably comprises a combination of straight sections 910 and ion beam turning sections 920. Hence, the circulating path of the protons is not circular in a synchrotron, but is rather a polygon with rounded corners.

In one illustrative embodiment, the synchrotron 130, which as also referred to as an accelerator system, has four straight sections and four turning sections. Examples of straight sections 910 include the: inflector 240, accelerator 270, extraction system 290, and deflector 292. Along with the four straight sections are four ion beam turning sections 920, which are also referred to as magnet sections or turning sections. Turning sections are further described, infra.

Figure 9:
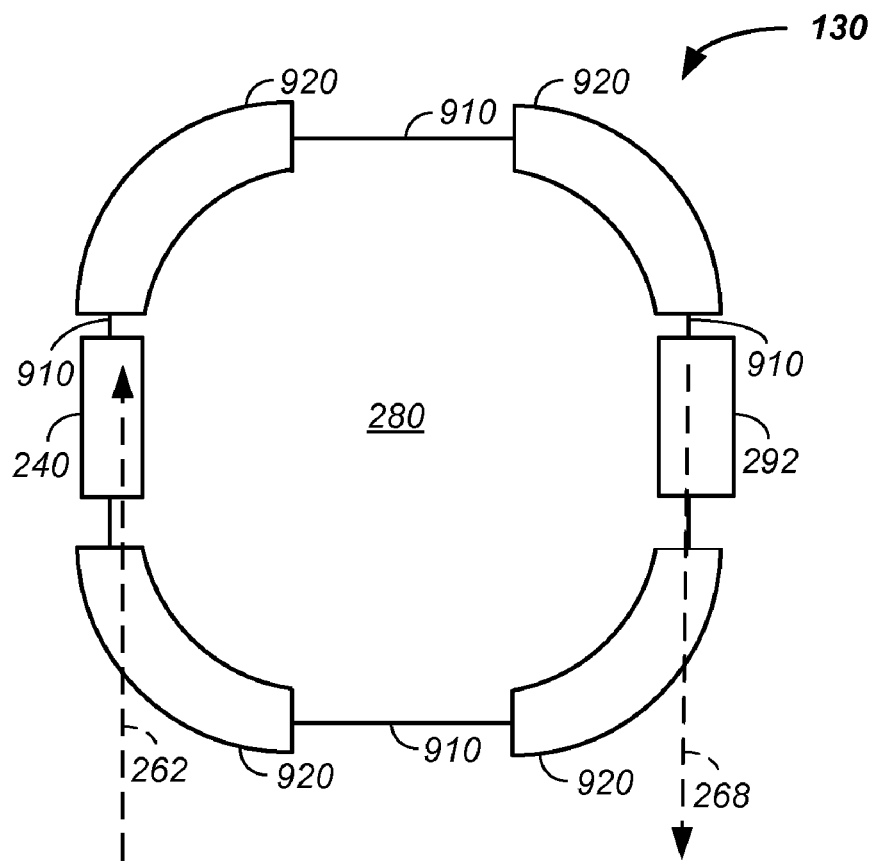
FIG. 9 illustrates straight and turning sections of a synchrotron

Referring now to FIG. 9, an exemplary synchrotron is illustrated. In this example, protons delivered along the initial proton beam path 262 are inflected into the circulating beam path with the inflector 240 and after acceleration are extracted via a deflector 292 to a beam transport path 268. In this example, the synchrotron 130 comprises four straight sections 910 and four bending or turning sections 920 where each of the four turning sections use one or more magnets to turn the proton beam about ninety degrees. As is further described, infra, the ability to closely space the turning sections and efficiently turn the proton beam results in shorter straight sections. Shorter straight sections allows for a synchrotron design without the use of focusing quadrupoles in the circulating beam path of the synchrotron. The removal of the focusing quadrupoles from the circulating proton beam path results in a more compact design. In this example, the illustrated synchrotron has about a five meter diameter versus eight meter and larger cross-sectional diameters for systems using a quadrupole focusing magnet in the circulating proton beam path.

Figure 10:
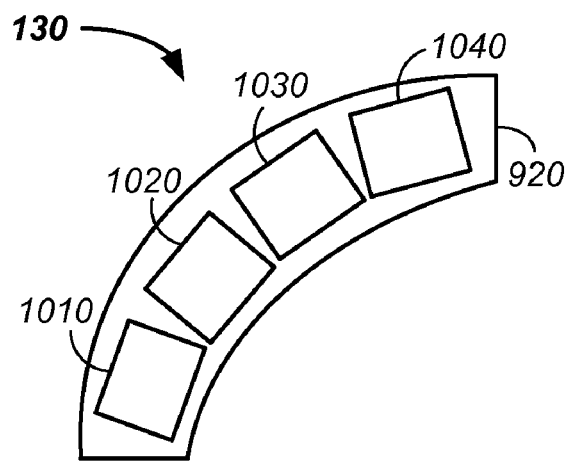
FIG. 10 illustrates bending magnets of a synchrotron.

Referring now to FIG. 10, additional description of the first bending or turning section 920 is provided. Each of the turning sections preferably comprises multiple magnets, such as about 2, 4, 6, 8, 10, or 12 magnets. In this example, four turning magnets 1010, 1020, 1030, 1040 in the first turning section 20 are used to illustrate key principles, which are the same regardless of the number of magnets in a turning section 920. A turning magnet 1010 is a particular type of main bending or circulating magnet 250.

In physics, the Lorentz force is the force on a point charge due to electromagnetic fields. The Lorentz force is given by equation 2 in terms of magnetic fields with the election field terms not included.

$$F = q(v \times B) \qquad \text{eq. 2}$$

In equation 2, F is the force in newtons; B is the magnetic field in Teslas; and v is the instantaneous velocity of the particles in meters per second.

Figure 11:
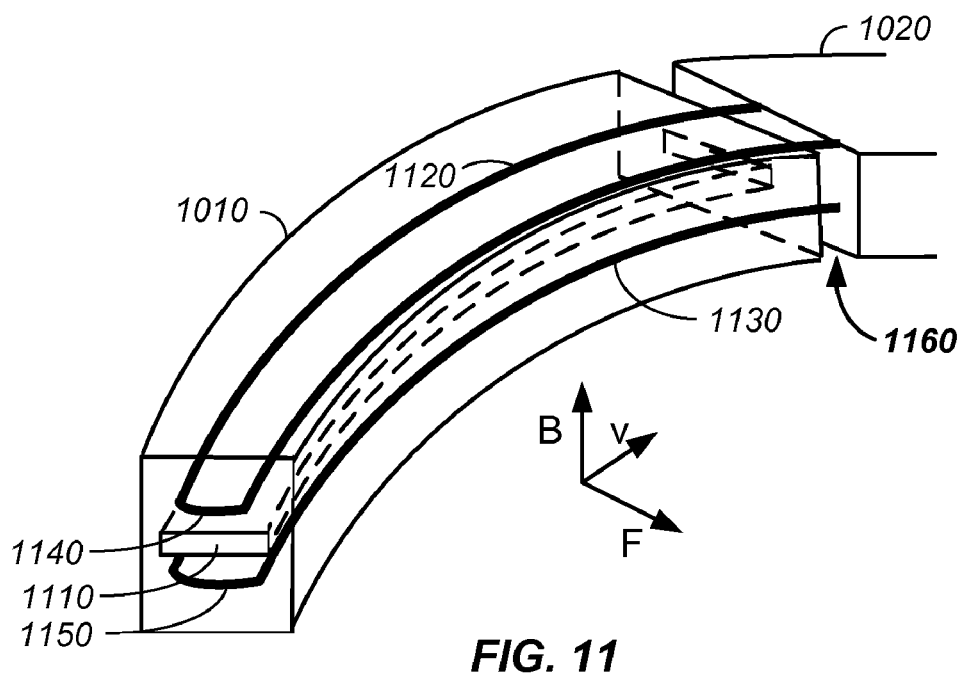
FIG. 11 provides a perspective view of a bending magnet.

Referring now to FIG. 11, an example of a single magnet bending or turning section 1010 is expanded. The turning section includes a gap 1110 through which protons circulate. The gap 1110 is preferably a flat gap, allowing for a magnetic field across the gap 1110 that is more uniform, even, and intense. A magnetic field enters the gap 1110 through a magnetic field incident surface and exits the gap 1110 through a magnetic field exiting surface. The gap 1110 runs in a vacuum tube between two magnet halves. The gap 1110 is controlled by at least two parameters: (1) the gap 1110 is kept as large as possible to minimize loss of protons and (2) the gap 1110 is kept as small as possible to minimize magnet sizes and the associated size and power requirements of the magnet power supplies. The flat nature of the gap 1110 allows for a compressed and more uniform magnetic field across the gap 1110. One example of a gap dimension is to accommodate a vertical proton beam size of about two centimeters with a horizontal beam size of about five to six centimeters.

As described, supra, a larger gap size requires a larger power supply. For instance, if the gap 1110 size doubles in vertical size, then the power supply requirements increase by about a factor of four. The flatness of the gap 1110 is also important. For example, the flat nature of the gap 1110 allows for an increase in energy of the extracted protons from about 250 to about 330 MeV. More particularly, if the gap 1110 has an extremely flat surface, then the limits of a magnetic field of an iron magnet are reachable. An exemplary precision of the flat surface of the gap 1110 is a polish of less than about 5 microns and preferably with a polish of about 1 to 3 microns. Unevenness in the surface results in imperfections in the applied magnetic field. The polished flat surface spreads unevenness of the applied magnetic field.

Still referring to FIG. 11, the charged particle beam moves through the gap 1110 with an instantaneous velocity, v. A first magnetic coil 1120 and a second magnetic coil 1130 run above and below the gap 1110, respectively. Current running through the coils 1120, 1130 results in a magnetic field, B, running through the single magnet turning section 1010. In this example, the magnetic field, B, runs upward, which results in a force, F, pushing the charged particle beam inward toward a central point of the synchrotron, which turns the charged particle beam in an arc.

Still referring to FIG. 11, a portion of an optional second magnet bending or turning section 1020 is illustrated. The coils 1120, 1130 typically have return elements 1140, 1150 or turns at the end of one magnet, such as at the end of the first magnet turning section 1010. The turns 1140, 1150 take space. The space reduces the percentage of the path about one orbit of the synchrotron that is covered by the turning magnets. This leads to portions of the circulating path where the protons are not turned and/or focused and allows for portions of the circulating path where the proton path defocuses. Thus, the space results in a larger synchrotron. Therefore, the space between magnet turning sections 1160 is preferably minimized. The second turning magnet is used to illustrate that the coils 1120, 1130 optionally run along a plurality of magnets, such as 2, 3, 4, 5, 6, or more magnets. Coils 1120, 1130 running across multiple turning section magnets allows for two turning section magnets to be spatially positioned closer to each other due to the removal of the steric constraint of the turns, which reduces and/or minimizes the space 1160 between two turning section magnets.

Figure 13:
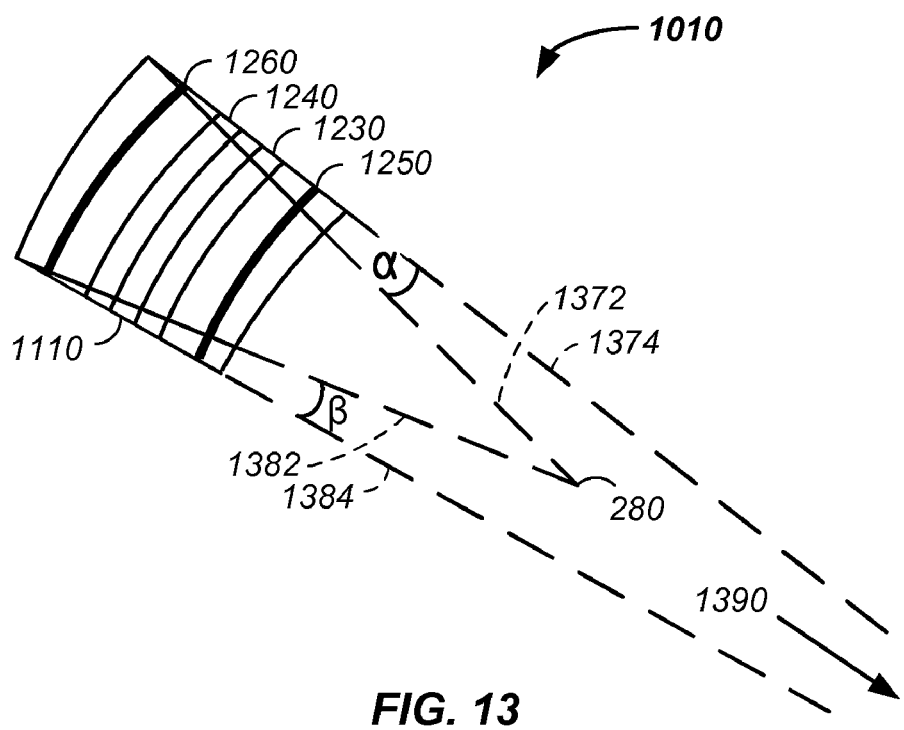
FIG. 13 illustrates a cross-sectional view of a bending magnet.
Figure 12:
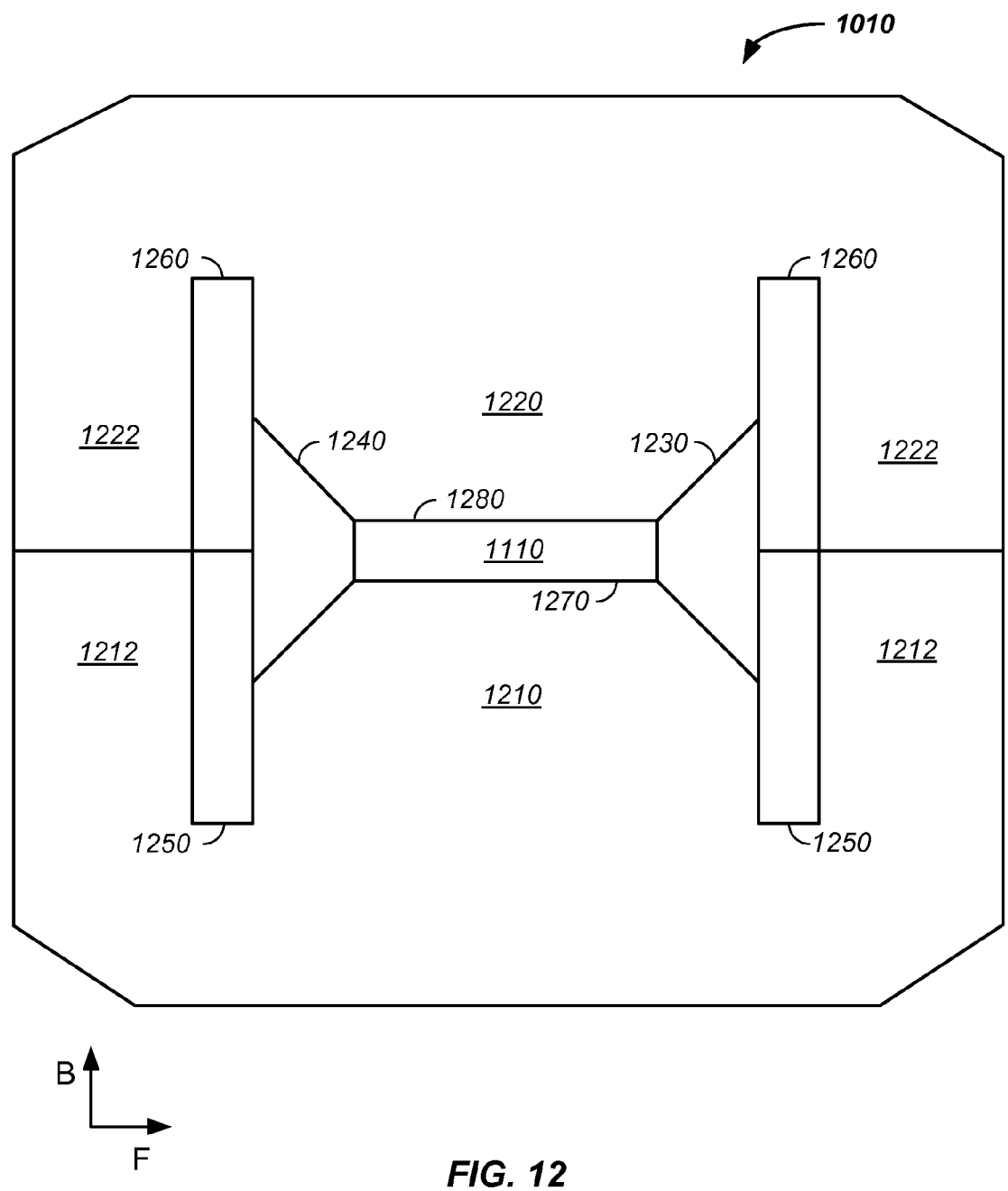
FIG. 12 illustrates a cross-sectional view of a bending magnet.

Referring now to FIGS. 12 and 13, two illustrative 90 degree rotated cross-sections of single magnet bending or turning sections 1010 are presented. The magnet assembly has a first magnet 1210 and a second magnet 1220. A magnetic field induced by coils, described infra, runs between the first magnet 1210 to the second magnet 1220 across the gap 1110. Return magnetic fields run through a first yoke 1212 and second yoke 1222. The combined cross-section area of the return yokes roughly approximates the cross-sectional area of the first magnet 1210 or second magnet 1220. The charged particles run through the vacuum tube in the gap 1110. As illustrated, protons run into FIG. 12 through the gap 1110 and the magnetic field, illustrated as vector B, applies a force F to the protons pushing the protons towards the center of the synchrotron, which is off page to the right in FIG. 12. The magnetic field is created using windings. A first coil makes up a first winding coil 1250 and a second coil of wire makes up a second winding coil 1260. Isolating or concentrating gaps 1230, 1240, such as air gaps, isolate the iron based yokes from the gap 1110. The gap 1110 is approximately flat to yield a uniform magnetic field across the gap 1110, as described supra.

Still referring to FIG. 13, the ends of a single bending or turning magnet are preferably beveled. Nearly perpendicular or right angle edges of a turning magnet 1010 are represented by dashed lines 1374, 1384. The dashed lines 1374, 1384 intersect at a point 1390 beyond the center of the synchrotron 280. Preferably, the edge of the turning magnet is beveled at angles alpha, α, and beta, β, which are angles formed by a first line 1372, 1382 going from an edge of the turning magnet 1010 and the center 280 and a second line 1374, 1384 going from the same edge of the turning magnet and the intersecting point 1390. The angle alpha is used to describe the effect and the description of angle alpha applies to angle beta, but angle alpha is optionally different from angle beta. The angle alpha provides an edge focusing effect. Beveling the edge of the turning magnet 1010 at angle alpha focuses the proton beam.

Multiple turning magnets provide multiple magnet edges that each have edge focusing effects in the synchrotron 130. If only one turning magnet is used, then the beam is only focused once for angle alpha or twice for angle alpha and angle beta. However, by using smaller turning magnets, more turning magnets fit into the turning sections 920 of the synchrotron 130. For example, if four magnets are used in a turning section 920 of the synchrotron, then for a single turning section there are eight possible edge focusing effect surfaces, two edges per magnet. The eight focusing surfaces yield a smaller cross-sectional beam size. This allows the use of a smaller gap 1110.

The use of multiple edge focusing effects in the turning magnets results in not only a smaller gap 1110, but also the use of smaller magnets and smaller power supplies. For a synchrotron 130 having four turning sections 920 where each turning sections has four turning magnets and each turning magnet has two focusing edges, a total of thirty-two focusing edges exist for each orbit of the protons in the circulating path of the synchrotron 130. Similarly, if 2, 6, or 8 magnets are used in a given turning section, or if 2, 3, 5, or 6 turning sections are used, then the number of edge focusing surfaces expands or contracts according to equation 3.

$$TFE = NTS * \frac{M}{NTS} * \frac{FE}{M} \qquad \text{eq. 3}$$

where TFE is the number of total focusing edges, NTS is the number of turning sections, M is the number of magnets, and FE is the number of focusing edges. Naturally, not all magnets are necessarily beveled and some magnets are optionally beveled on only one edge.

The inventors have determined that multiple smaller magnets have benefits over fewer larger magnets. For example, the use of 16 small magnets yields 32 focusing edges whereas the use of 4 larger magnets yields only 8 focusing edges. The use of a synchrotron having more focusing edges results in a circulating path of the synchrotron built without the use of focusing quadrupoles magnets. All prior art synchrotrons use quadrupoles in the circulating path of the synchrotron. Further, the use of quadrupoles in the circulating path necessitates additional straight sections in the circulating path of the synchrotron. Thus, the use of quadrupoles in the circulating path of a synchrotron results in synchrotrons having larger diameters, circulating beam pathlengths, and/or larger circumferences.

In various embodiments of the system described herein, the synchrotron has any combination of:
- at least 4 and preferably 6, 8, 10, or more edge focusing edges per 90 degrees of turn of the charged particle beam in a synchrotron having four turning sections;
- at least about 16 and preferably about 24, 32, or more edge focusing edges per orbit of the charged particle beam in the synchrotron;
- only 4 turning sections where each of the turning sections includes at least 4 and preferably 8 edge focusing edges;
- an equal number of straight sections and turning sections;
- exactly 4 turning sections;
- at least 4 edge focusing edges per turning section;
- no quadrupoles in the circulating path of the synchrotron;
- a rounded corner rectangular polygon configuration;
- a circumference of less than 60 meters;
- a circumference of less than 60 meters and 32 edge focusing surfaces; and/or
- any of about 8, 16, 24, or 32 non-quadrupole magnets per circulating path of the synchrotron, where the non-quadrupole magnets include edge focusing edges.

Referring now to FIG. 12, the incident magnetic field surface 1270 of the first magnet 1210 is further described. FIG. 12 is not to scale and is illustrative in nature. Local imperfections or unevenness in quality of the finish of the incident surface 1270 results in inhomogeneities or imperfections in the magnetic field applied to the gap 1110. Preferably, the incident surface 1270 is flat, such as to within about a zero to three micron finish polish, or less preferably to about a ten micron finish polish.

Figure 14:
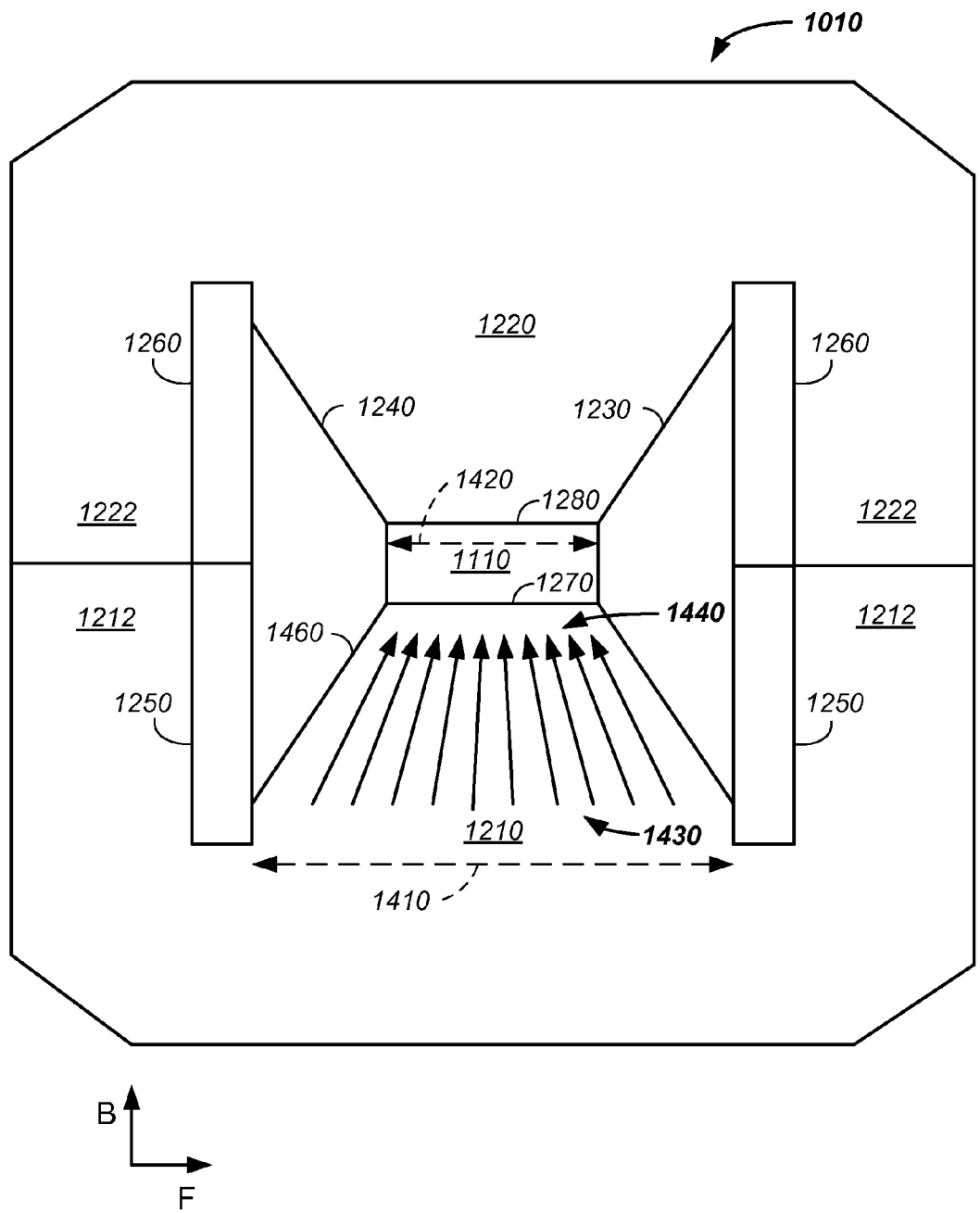
FIG. 14 illustrates magnetic field concentration in a bending magnet.

Referring now to FIG. 14, additional optional magnet elements, of the magnet cross-section illustratively represented in FIG. 12, are described. The first magnet 1210 preferably contains an initial cross-sectional distance 1410 of the iron based core. The contours of the magnetic field are shaped by the magnets 1210, 1220 and the yokes 1212, 1222. The iron based core tapers to a second cross-sectional distance 1420. The magnetic field in the magnet preferentially stays in the iron based core as opposed to the gaps 1230, 1240. As the cross-sectional distance decreases from the initial cross-sectional distance 1410 to the final cross-sectional distance 1420, the magnetic field concentrates. The change in shape of the magnet from the longer distance 1410 to the smaller distance 1420 acts as an amplifier. The concentration of the magnetic field is illustrated by representing an initial density of magnetic field vectors 1430 in the initial cross-section 1410 to a concentrated density of magnetic field vectors 1440 in the final cross-section 1420. The concentration of the magnetic field due to the geometry of the turning magnets results in fewer winding coils 1250, 1260 being required and also a smaller power supply to the coils being required.

Example I

In one example, the initial cross-section distance 1410 is about fifteen centimeters and the final cross-section distance 1420 is about ten centimeters. Using the provided numbers, the concentration of the magnetic field is about 15/10 or 1.5 times at the incident surface 1270 of the gap 1110, though the relationship is not linear. The taper 1460 has a slope, such as about 20, 40, or 60 degrees. The concentration of the magnetic field, such as by 1.5 times, leads to a corresponding decrease in power consumption requirements to the magnets.

Figure 15:
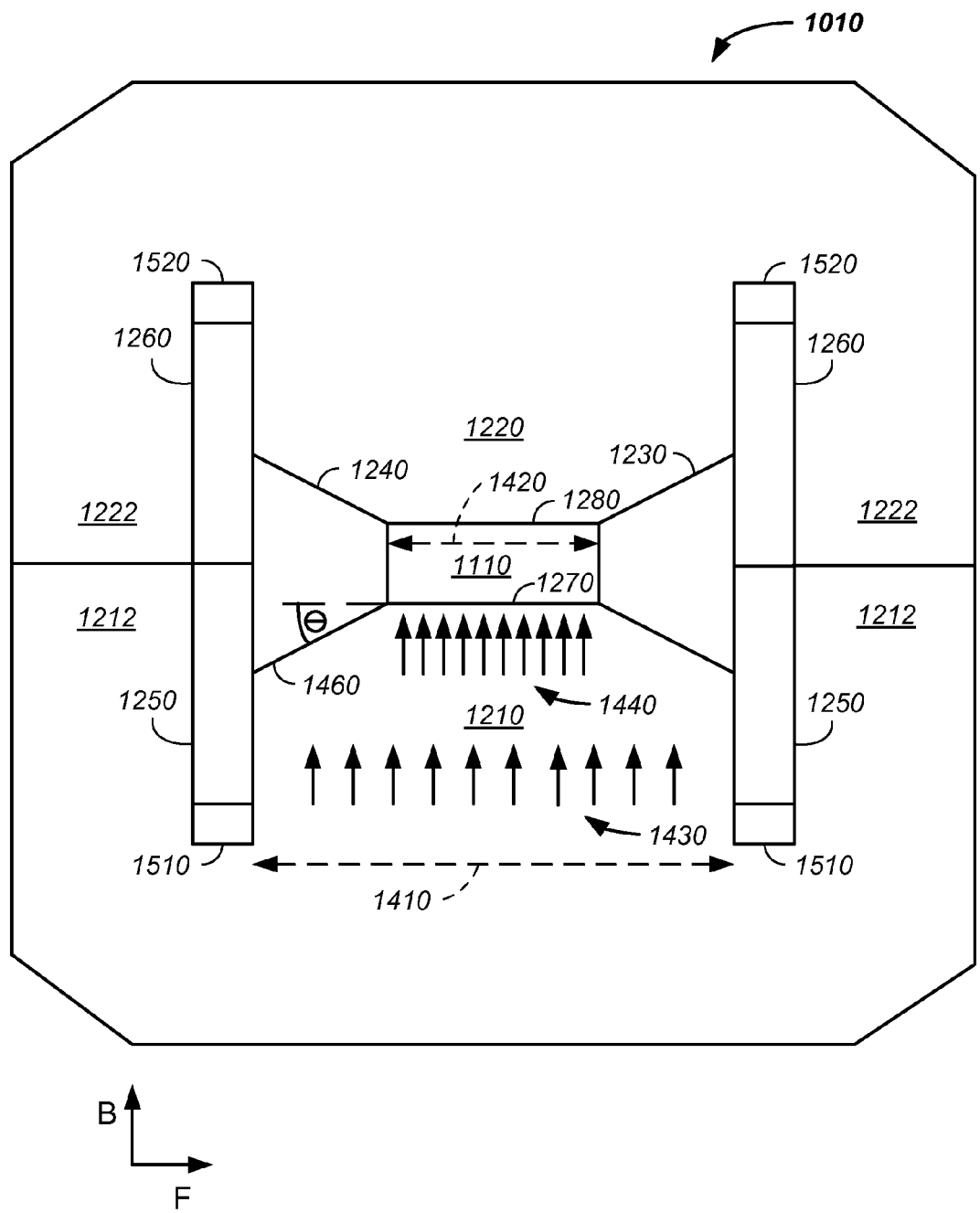
FIG. 15 illustrates correction coils in a bending magnet.

Referring now to FIG. 15, an additional example of geometry of the magnet used to concentrate the magnetic field is illustrated. As illustrated in FIG. 14, the first magnet 1210 preferably contains an initial cross-sectional distance 1410 of the iron based core. The contours of the magnetic field are shaped by the magnets 1210, 1220 and the yokes 1212, 1222. In this example, the core tapers to a second cross-sectional distance 1420 with a smaller angle theta, θ. As described, supra, the magnetic field in the magnet preferentially stays in the iron based core as opposed to the gaps 1230, 1240. As the cross-sectional distance decreases from the initial cross-sectional distance 1410 to the final cross-sectional distance 1420, the magnetic field concentrates. The smaller angle, theta, results in a greater amplification of the magnetic field in going from the longer distance 1410 to the smaller distance 1420. The concentration of the magnetic field is illustrated by representing an initial density of magnetic field vectors 1430 in the initial cross-section 1410 to a concentrated density of magnetic field vectors 1440 in the final cross-section 1420. The concentration of the magnetic field due to the geometry of the turning magnets results in fewer winding coils 1250, 1260 being required and also a smaller power supply to the winding coils 1250, 1260 being required.

Still referring to FIG. 15, optional correction coils 1510, 1520 are illustrated that are used to correct the strength of one or more turning magnets. The correction coils 1520, 1530 supplement the winding coils 1250, 1260. The correction coils 1510, 1520 have correction coil power supplies that are separate from winding coil power supplies used with the winding coils 1250, 1260. The correction coil power supplies typically operate at a fraction of the power required compared to the winding coil power supplies, such as about 1, 2, 3, 5, 7, or 10 percent of the power and more preferably about 1 or 2 percent of the power used with the winding coils 1250, 1260. The smaller operating power applied to the correction coils 1510, 1520 allows for more accurate and/or precise control of the correction coils. The correction coils 1610, 1620 are used to adjust for imperfection in the turning magnets 1010, 1020. Optionally, separate correction coils are used for each turning magnet allowing individual tuning of the magnetic field for each turning magnet, which eases quality requirements in the manufacture of each turning magnet.

Figure 16:
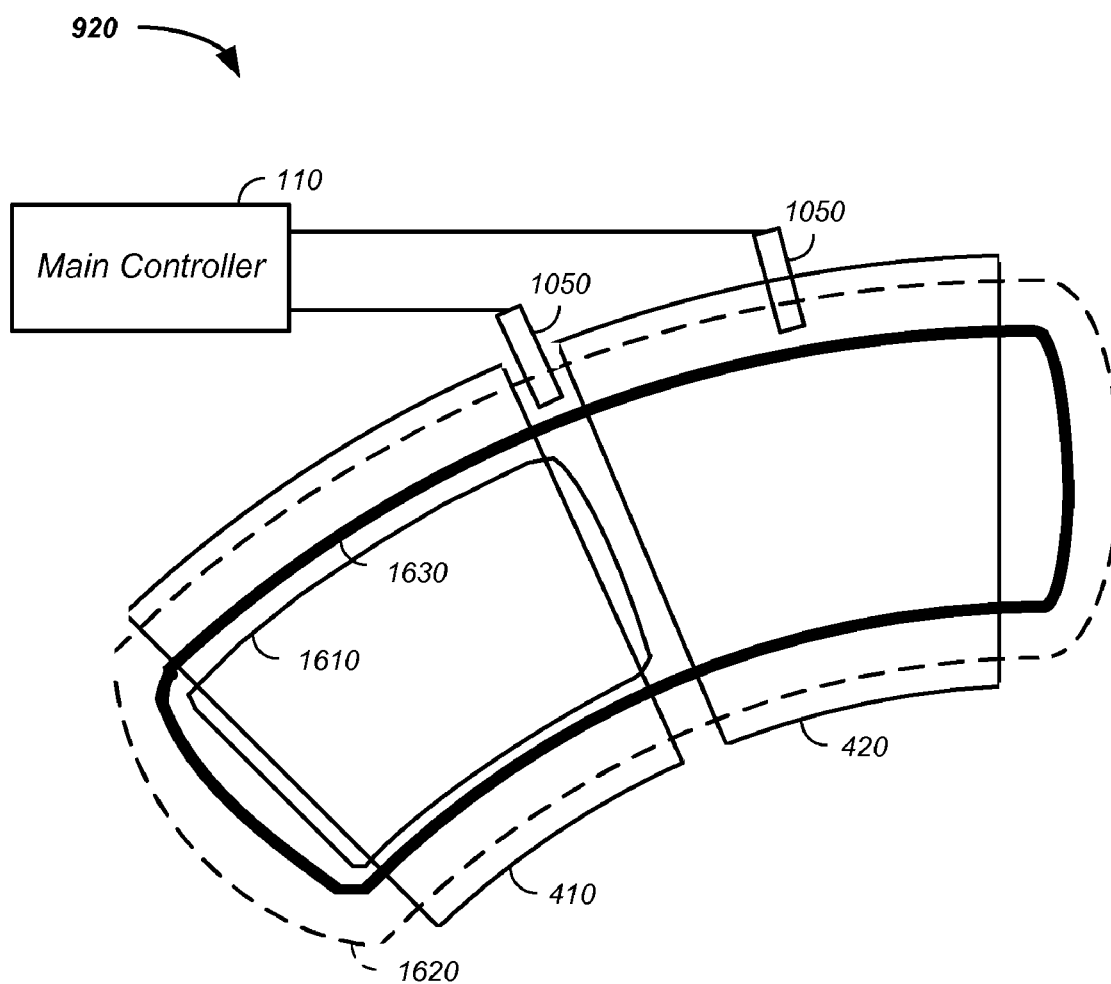
FIG. 16 illustrates a magnetic turning section of a synchrotron.

Referring now to FIG. 16, an example of winding coils and correction coils about a plurality of turning magnets 1610, 1620 in an ion beam turning section 920 is illustrated. One or more high precision magnetic field sensors are placed into the synchrotron and are used to measure the magnetic field at or near the proton beam path. For example, the magnetic sensors are optionally placed between turning magnets and/or within a turning magnet, such as at or near the gap 1110 or at or near the magnet core or yoke. The sensors are part of a feedback system to the correction coils. Thus, the system preferably stabilizes the magnetic field in the synchrotron rather than stabilizing the current applied to the magnets. Stabilization of the magnetic field allows the synchrotron to come to a new energy level quickly. This allows the system to be controlled to an operator or algorithm selected energy level with each pulse of the synchrotron and/or with each breath of the patient.

The winding and/or correction coils correct 1, 2, 3, or 4 turning magnets, and preferably correct a magnetic field generated by two turning magnets. A winding or correction coil covering multiple magnets reduces space between magnets as fewer winding or correction coil ends are required, which occupy space. In the illustrated example, a correction coil 1610 winds around a single turning magnet 410. In another example, a correction coil 1620 wraps around two turning magnets 410, 420.

Example II

Figure 17:
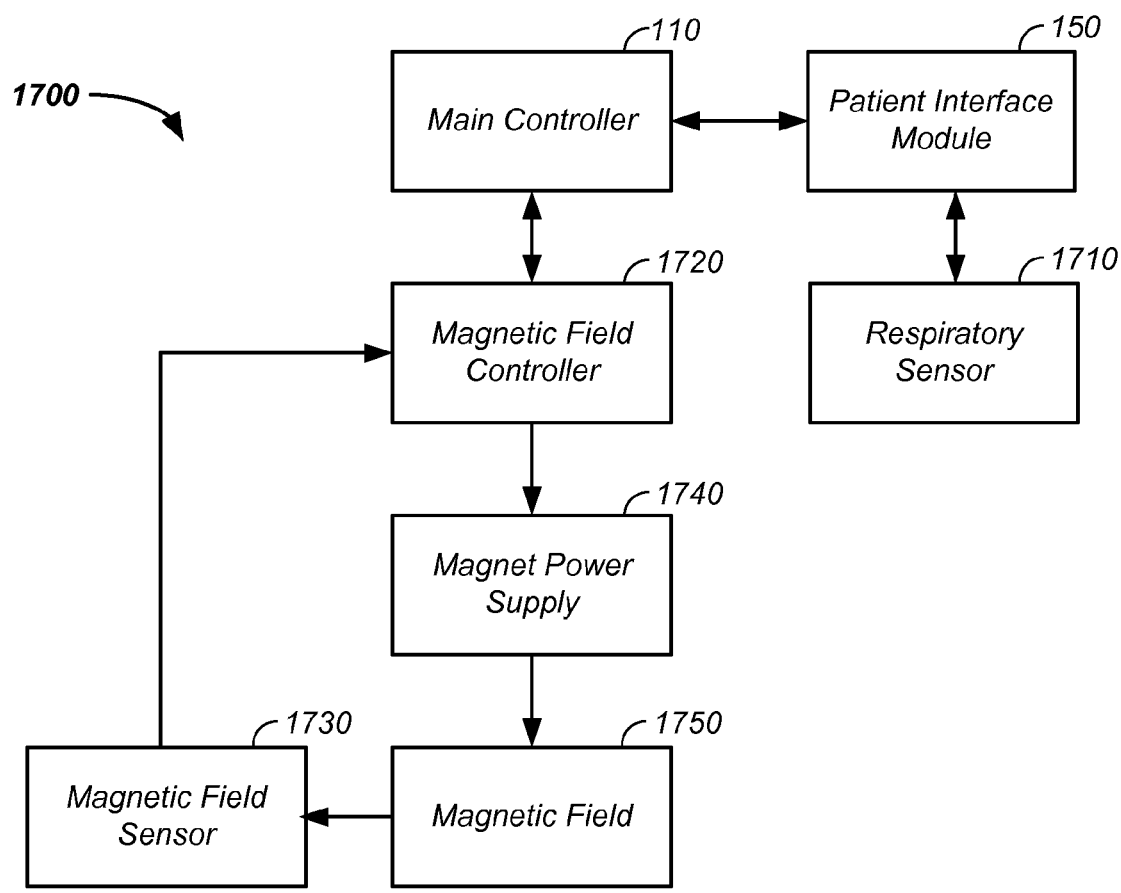
FIG. 17 illustrates a magnetic field control system.

Referring now to FIG. 17, an example is used to clarify the magnetic field control using a feedback loop 1700 to change delivery times and/or periods of proton pulse delivery. In one case, a respiratory sensor 1710 senses the respiration cycle of the subject. The respiratory sensor sends the information to an algorithm in a magnetic field controller 1720, typically via the patient interface module 150 and/or via the main controller 110 or a subcomponent thereof. The algorithm predicts and/or measures when the subject is at a particular point in the respiration or breathing cycle, such as at the bottom of a breath. Magnetic field sensors 1730 are used as input to the magnetic field controller, which controls a magnet power supply 1740 for a given magnetic field 1750, such as within a first turning magnet 1010 of a synchrotron 130. The control feedback loop is thus used to dial the synchrotron to a selected energy level and deliver protons with the desired energy at a selected point in time, such as at the bottom of the breath. More particularly, the main controller injects protons into the synchrotron and accelerates the protons in a manner that combined with extraction delivers the protons to the tumor at a selected point in the respiration cycle. Intensity of the proton beam is also selectable and controllable by the main controller at this stage. The feedback control to the correction coils allows rapid selection of energy levels of the synchrotron that are tied to the patient's respiration cycle. This system is in stark contrast to a system where the current is stabilized and the synchrotron deliver pulses with a period, such as 10 or 20 cycles per second with a fixed period.

The feedback or the magnetic field design coupled with the correction coils allows for the extraction cycle to match the varying respiratory rate of the patient. Traditional extraction systems do not allow this control as magnets have memories in terms of both magnitude and amplitude of a sine wave. Hence, in a traditional system, in order to change frequency, slow changes in current must be used. However, with the use of the feedback loop using the magnetic field sensors, the frequency and energy level of the synchrotron are rapidly adjustable. Further aiding this process is the use of a novel extraction system that allows for acceleration of the protons during the extraction process, described infra.

Example III

Referring again to FIG. 16, an example of a winding coil 1630 that covers four turning magnets 1010, 1020 is provided. Optionally, a first winding coil 1640 covers two magnets and a second winding coil covers another two magnets. As described, supra, this system reduces space between turning section allowing more magnetic field to be applied per radian of turn. A first correction coil 1610 is illustrated that is used to correct the magnetic field for the first turning magnet 1010. A second correction coil 1620 is illustrated that is used to correct the magnetic field for a winding coil 1630 about two turning magnets. Individual correction coils for each turning magnet are preferred and individual correction coils yield the most precise and/or accurate magnetic field in each turning section. Particularly, the individual correction coil 1610 is used to compensate for imperfections in the individual magnet of a given turning section. Hence, with a series of magnetic field sensors, corresponding magnetic fields are individually adjustable in a series of feedback loops, via a magnetic field monitoring system, as an independent coil is used for each turning section. Alternatively, a multiple magnet correction coil is used to correct the magnetic field for a plurality of turning section magnets.

Flat Gap Surface

While the gap surface is described in terms of the first turning magnet 1010, the discussion applies to each of the turning magnets in the synchrotron. Similarly, while the gap 1110 surface is described in terms of the magnetic field incident surface 1270, the discussion additionally optionally applies to the magnetic field exiting surface 1280.

The magnetic field incident surface 1270 of the first magnet 1210 is preferably about flat, such as to within about a zero to three micron finish polish or less preferably to about a ten micron finish polish. By being very flat, the polished surface spreads the unevenness of the applied magnetic field across the gap 1110. The very flat surface, such as about 0, 1, 2, 4, 6, 8, 10, 15, or 20 micron finish, allows for a smaller gap size, a smaller applied magnetic field, smaller power supplies, and tighter control of the proton beam cross-sectional area.

Proton Beam Extraction

Figure 18:
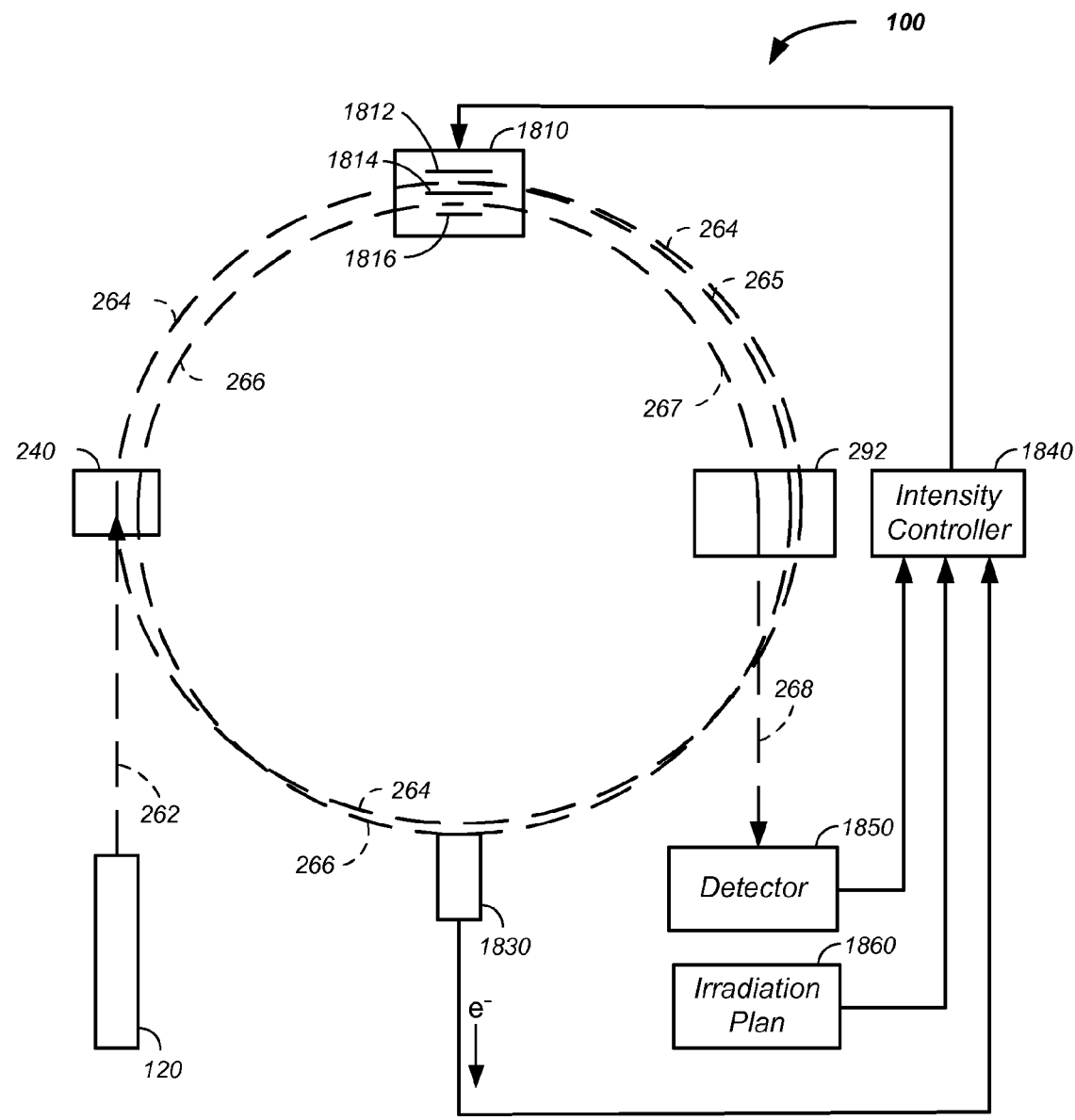
FIG. 18 illustrates a charged particle extraction and intensity control system.

Referring now to FIG. 18, an exemplary proton extraction process from the synchrotron 130 is illustrated. For clarity, FIG. 18 removes elements represented in FIG. 2, such as the turning magnets, which allows for greater clarity of presentation of the proton beam path as a function of time. Generally, protons are extracted from the synchrotron 130 by slowing the protons. As described, supra, the protons were initially accelerated in a circulating path 264, which is maintained with a plurality of main bending magnets 250. The circulating path is referred to herein as an original central beamline 264. The protons repeatedly cycle around a central point in the synchrotron 280. The proton path traverses through a radio frequency (RF) cavity system 1810. To initiate extraction, an RF field is applied across a first blade 1812 and a second blade 1814, in the RF cavity system 1810. The first blade 1812 and second blade 1814 are referred to herein as a first pair of blades.

In the proton extraction process, an RF voltage is applied across the first pair of blades, where the first blade 1812 of the first pair of blades is on one side of the circulating proton beam path 264 and the second blade 1814 of the first pair of blades is on an opposite side of the circulating proton beam path 264. The applied RF field applies energy to the circulating charged-particle beam. The applied RF field alters the orbiting or circulating beam path slightly of the protons from the original central beamline 264 to an altered circulating beam path 265. Upon a second pass of the protons through the RF cavity system, the RF field further moves the protons off of the original proton beamline 264. For example, if the original beamline is considered as a circular path, then the altered beamline is slightly elliptical. The applied RF field is timed to apply outward or inward movement to a given band of protons circulating in the synchrotron accelerator. Each orbit of the protons is slightly more off axis compared to the original circulating beam path 264. Successive passes of the protons through the RF cavity system are forced further and further from the original central beamline 264 by altering the direction and/or intensity of the RF field with each successive pass of the proton beam through the RF field.

The RF voltage is frequency modulated at a frequency about equal to the period of one proton cycling around the synchrotron for one revolution or at a frequency than is an integral multiplier of the period of one proton cycling about the synchrotron. The applied RF frequency modulated voltage excites a betatron oscillation. For example, the oscillation is a sine wave motion of the protons. The process of timing the RF field to a given proton beam within the RF cavity system is repeated thousands of times with each successive pass of the protons being moved approximately one micrometer further off of the original central beamline 264. For clarity, the approximately 1000 changing beam paths with each successive path of a given band of protons through the RF field are illustrated as the altered beam path 265.

With a sufficient sine wave betatron amplitude, the altered circulating beam path 265 touches or traverses a material 1830, such as a foil or a sheet of foil. The foil is preferably a lightweight material, such as beryllium, a lithium hydride, a carbon sheet, or a material of low nuclear charge. A material of low nuclear charge is a material composed of atoms consisting essentially of atoms having six or fewer protons. The foil is preferably about 10 to 150 microns thick, is more preferably 30 to 100 microns thick, and is still more preferably about 40 to 60 microns thick. In one example, the foil is beryllium with a thickness of about 50 microns. When the protons traverse through the foil, energy of the protons is lost and the speed of the protons is reduced. Typically, a current is also generated, described infra. Protons moving at a slower speed travel in the synchrotron with a reduced radius of curvature 266 compared to either the original central beamline 264 or the altered circulating path 265. The reduced radius of curvature 266 path is also referred to herein as a path having a smaller diameter of trajectory or a path having protons with reduced energy. The reduced radius of curvature 266 is typically about two millimeters less than a radius of curvature of the last pass of the protons along the altered proton beam path 265.

The thickness of the material 1830 is optionally adjusted to created a change in the radius of curvature, such as about ½, 1, 2, 3, or 4 mm less than the last pass of the protons 265 or original radius of curvature 264. Protons moving with the smaller radius of curvature travel between a second pair of blades. In one case, the second pair of blades is physically distinct and/or are separated from the first pair of blades. In a second case, one of the first pair of blades is also a member of the second pair of blades. For example, the second pair of blades is the second blade 1814 and a third blade 1816 in the RF cavity system 1810. A high voltage DC signal, such as about 1 to 5 kV, is then applied across the second pair of blades, which directs the protons out of the synchrotron through an extraction magnet 292, such as a Lamberson extraction magnet, into a transport path 268.

Control of acceleration of the charged particle beam path in the synchrotron with the accelerator and/or applied fields of the turning magnets in combination with the above described extraction system allows for control of the intensity of the extracted proton beam, where intensity is a proton flux per unit time or the number of protons extracted as a function of time. For example, when a current is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

Because the extraction system does not depend on any change in magnetic field properties, it allows the synchrotron to continue to operate in acceleration or deceleration mode during the extraction process. Stated differently, the extraction process does not interfere with synchrotron acceleration. In stark contrast, traditional extraction systems introduce a new magnetic field, such as via a hexapole, during the extraction process. More particularly, traditional synchrotrons have a magnet, such as a hexapole magnet, that is off during an acceleration stage. During the extraction phase, the hexapole magnetic field is introduced to the circulating path of the synchrotron. The introduction of the magnetic field necessitates two distinct modes, an acceleration mode and an extraction mode, which are mutually exclusive in time.

Charged Particle Beam Intensity Control

Control of applied field, such as a radio-frequency (RF) field, frequency and magnitude in the RF cavity system 1810 allows for intensity control of the extracted proton beam, where intensity is extracted proton flux per unit time or the number of protons extracted as a function of time.

Referring still to FIG. 18, when protons in the proton beam hit the material 1830 electrons are given off resulting in a current. The resulting current is converted to a voltage and is used as part of a ion beam intensity monitoring system or as part of an ion beam feedback loop for controlling beam intensity. The voltage is optionally measured and sent to the main controller 110 or to a controller subsystem 1840. More particularly, when protons in the charged particle beam path pass through the material 1830, some of the protons lose a small fraction of their energy, such as about one-tenth of a percent, which results in a secondary electron. That is, protons in the charged particle beam push some electrons when passing through material 1830 giving the electrons enough energy to cause secondary emission. The resulting electron flow results in a current or signal that is proportional to the number of protons going through the target material 1830. The resulting current is preferably converted to voltage and amplified. The resulting signal is referred to as a measured intensity signal.

The amplified signal or measured intensity signal resulting from the protons passing through the material 1830 is preferably used in controlling the intensity of the extracted protons. For example, the measured intensity signal is compared to a goal signal, which is predetermined in an irradiation of the tumor plan. The difference between the measured intensity signal and the planned for goal signal is calculated. The difference is used as a control to the RF generator. Hence, the measured flow of current resulting from the protons passing through the material 1830 is used as a control in the RF generator to increase or decrease the number of protons undergoing betatron oscillation and striking the material 1830. Hence, the voltage determined off of the material 1830 is used as a measure of the orbital path and is used as a feedback control to control the RF cavity system. Alternatively, the measured intensity signal is not used in the feedback control and is just used as a monitor of the intensity of the extracted protons.

As described, supra, the photons striking the material 1830 is a step in the extraction of the protons from the synchrotron 130. Hence, the measured intensity signal is used to change the number of protons per unit time being extracted, which is referred to as intensity of the proton beam. The intensity of the proton beam is thus under algorithm control. Further, the intensity of the proton beam is controlled separately from the velocity of the protons in the synchrotron 130. Hence, intensity of the protons extracted and the energy of the protons extracted are independently variable.

For example, protons initially move at an equilibrium trajectory in the synchrotron 130. An RF field is used to excite the protons into a betatron oscillation. In one case, the frequency of the protons orbit is about 10 MHz. In one example, in about one millisecond or after about 10,000 orbits, the first protons hit an outer edge of the target material 130. The specific frequency is dependent upon the period of the orbit. Upon hitting the material 130, the protons push electrons through the foil to produce a current. The current is converted to voltage and amplified to yield a measured intensity signal. The measured intensity signal is used as a feedback input to control the applied RF magnitude, RF frequency, or RF field. Preferably, the measured intensity signal is compared to a target signal and a measure of the difference between the measured intensity signal and target signal is used to adjust the applied RF field in the RF cavity system 1810 in the extraction system to control the intensity of the protons in the extraction step. Stated again, the signal resulting from the protons striking and/or passing through the material 130 is used as an input in RF field modulation. An increase in the magnitude of the RF modulation results in protons hitting the foil or material 130 sooner. By increasing the RF, more protons are pushed into the foil, which results in an increased intensity, or more protons per unit time, of protons extracted from the synchrotron 130.

In another example, a detector 1850 external to the synchrotron 130 is used to determine the flux of protons extracted from the synchrotron and a signal from the external detector is used to alter the RF field or RF modulation in the RF cavity system 1810. Here the external detector generates an external signal, which is used in a manner similar to the measured intensity signal, described in the preceding paragraphs.

In yet another example, when a current from material 130 resulting from protons passing through or hitting material is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In still yet another embodiment, intensity modulation of the extracted proton beam is controlled by the main controller 110. The main controller 110 optionally and/or additionally controls timing of extraction of the charged particle beam and energy of the extracted proton beam.

The benefits of the system include a multi-dimensional scanning system. Particularly, the system allows independence in: (1) energy of the protons extracted and (2) intensity of the protons extracted. That is, energy of the protons extracted is controlled by an energy control system and an intensity control system controls the intensity of the extracted protons. The energy control system and intensity control system are optionally independently controlled. Preferably, the main controller 110 controls the energy control system and the main controller simultaneously controls the intensity control system to yield an extracted proton beam with controlled energy and controlled intensity where the controlled energy and controlled intensity are independently variable. Thus the irradiation spot hitting the tumor is under independent control of:

time;
energy;
intensity;
x-axis position, where the x-axis represents horizontal movement of the proton beam relative to the patient, and
y-axis position, where the y-axis represents vertical movement of the proton beam relative to the patient.

In addition, the patient is optionally independently rotated relative to a translational axis of the proton beam at the same time.

Patient Positioning

Referring now to FIG. 19, the patient is preferably positioned on or within a patient positioning system 1910 of the patient interface module 150. The patient positioning system 1910 is used to translate the patient and/or rotate the patient into a zone where the proton beam can scan the tumor using a scanning system 140 or proton targeting system, described infra. Essentially, the patient positioning system 1910 performs large movements of the patient to place the tumor near the center of a proton beam path 268 and the proton scanning or targeting system 140 performs fine movements of the momentary beam position 269 in targeting the tumor 1920. To illustrate, FIG. 19 shows the momentary proton beam position 269 and a range of scannable positions 1940 using the proton scanning or targeting system 140, where the scannable positions 1940 are about the tumor 1920 of the patient 1930. This illustratively shows that the y-axis movement of the patient occurs on a scale of the body, such as adjustment of about 1, 2, 3, or 4 feet, while the scannable region of the proton beam 268 covers a portion of the body, such as a region of about 1, 2, 4, 6, 8, 10, or 12 inches. The patient positioning system and its rotation and/or translation of the patient combines with the proton targeting system to yield precise and/or accurate delivery of the protons to the tumor.

Figure 19A:
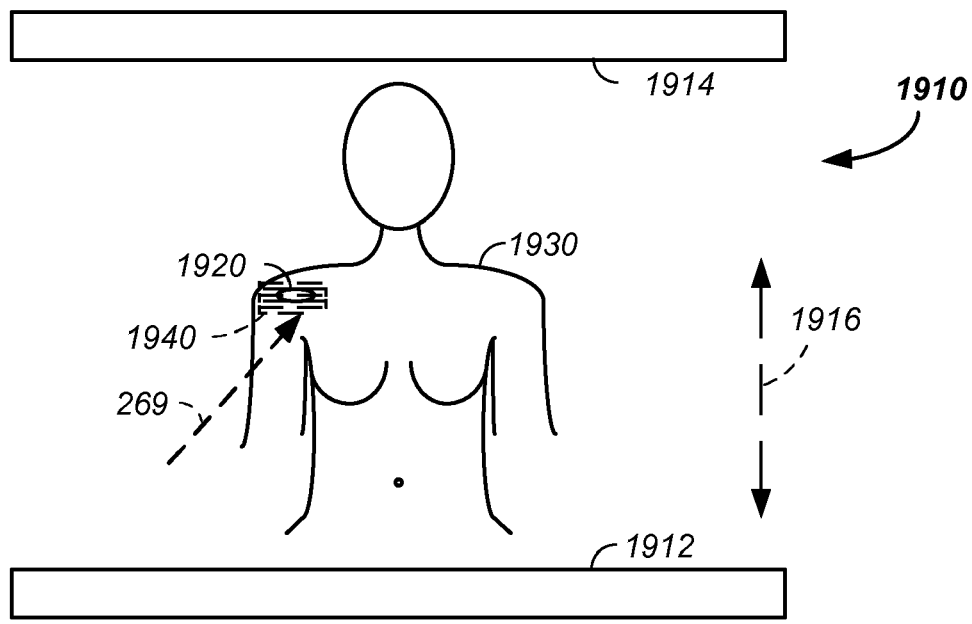
FIG. 19 illustrates a patient positioning system from: (A) a front view and (B) a top view.
Figure 19B:
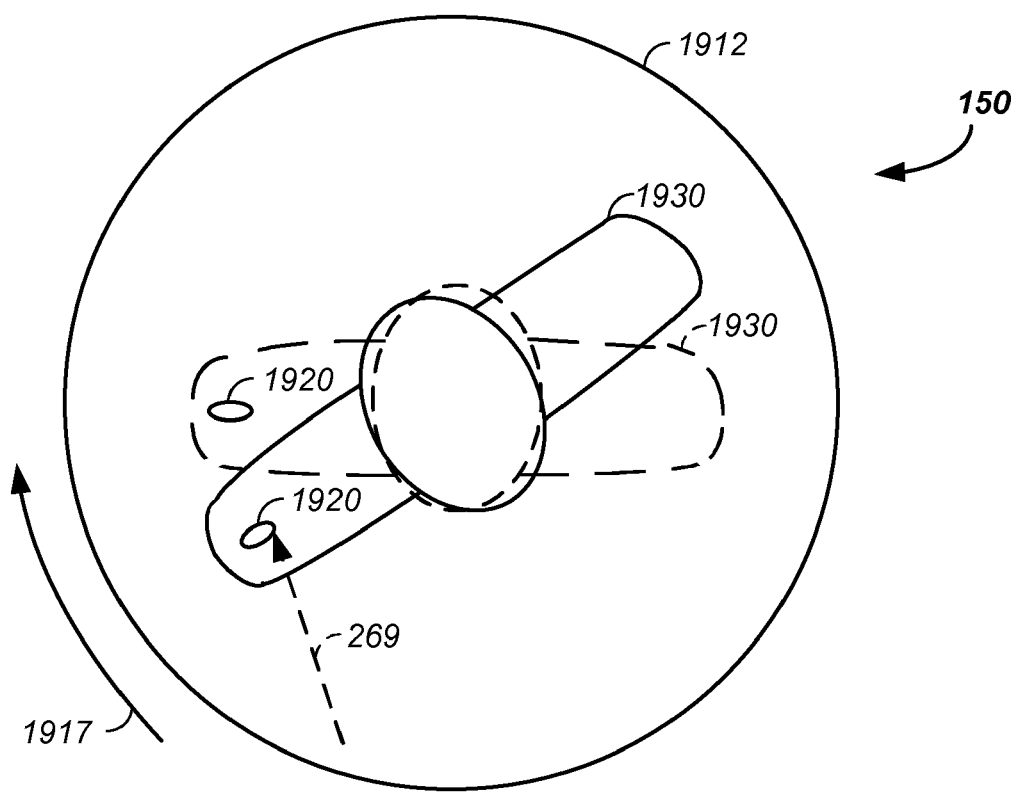

Referring still to FIG. 19, the patient positioning system 1910 optionally includes a bottom unit 1912 and a top unit 1914, such as discs or a platform. Referring now to FIG. 19A, the patient positioning unit 1910 is preferably y-axis adjustable 1916 to allow vertical shifting of the patient relative to the proton therapy beam 268. Preferably, the vertical motion of the patient positioning unit 1910 is about 10, 20, 30, or 50 centimeters per minute. Referring now to FIG. 19B, the patient positioning unit 1910 is also preferably rotatable 1917 about a rotation axis, such as about the y-axis, to allow rotational control and positioning of the patient relative to the proton beam path 268. Preferably the rotational motion of the patient positioning unit 1910 is about 360 degrees per minute. Optionally, the patient positioning unit rotates about 45, 90, or 180 degrees. Optionally, the patient positioning unit 1910 rotates at a rate of about 45, 90, 180, 360, 720, or 1080 degrees per minute. The rotation of the positioning unit 1917 is illustrated about the rotation axis at two distinct times, $t_1$ and $t_2$. Protons are optionally delivered to the tumor 1920 at n times where each of the n times represent different directions of the incident proton beam 269 hitting the patient 1930 due to rotation of the patient 1917 about the rotation axis.

Any of the semi-vertical, sitting, or laying patient positioning embodiments described, infra, are optionally vertically translatable along the y-axis or rotatable about the rotation or y-axis.

Preferably, the top and bottom units 1912, 1914 move together, such that they rotate at the same rates and translate in position at the same rates. Optionally, the top and bottom units 1912, 1914 are independently adjustable along the y-axis to allow a difference in distance between the top and bottom units 1912, 1914. Motors, power supplies, and mechanical assemblies for moving the top and bottom units 1912, 1914 are preferably located out of the proton beam path 269, such as below the bottom unit 1912 and/or above the top unit 1914. This is preferable as the patient positioning unit 1910 is preferably rotatable about 360 degrees and the motors, power supplies, and mechanical assemblies interfere with the protons if positioned in the proton beam path 269

Proton Beam Position Control

Referring now to FIG. 20, a beam delivery and tissue volume scanning system is illustrated. Presently, the worldwide radiotherapy community uses a method of dose field forming using a pencil beam scanning system. In stark contrast, FIG. 20 illustrates a spot scanning system or tissue volume scanning system. In the tissue volume scanning system, the proton beam is controlled, in terms of transportation and distribution, using an inexpensive and precise scanning system. The scanning system is an active system, where the beam is focused into a spot focal point of about one-half, one, two, or three millimeters in diameter. The focal point is translated along two axes while simultaneously altering the applied energy of the proton beam, which effectively changes the third dimension of the focal point. The system is applicable in combination with the above described rotation of the body, which preferably occurs in-between individual moments or cycles of proton delivery to the tumor. Optionally, the rotation of the body by the above described system occurs continuously and simultaneously with proton delivery to the tumor.

Figure 20A:
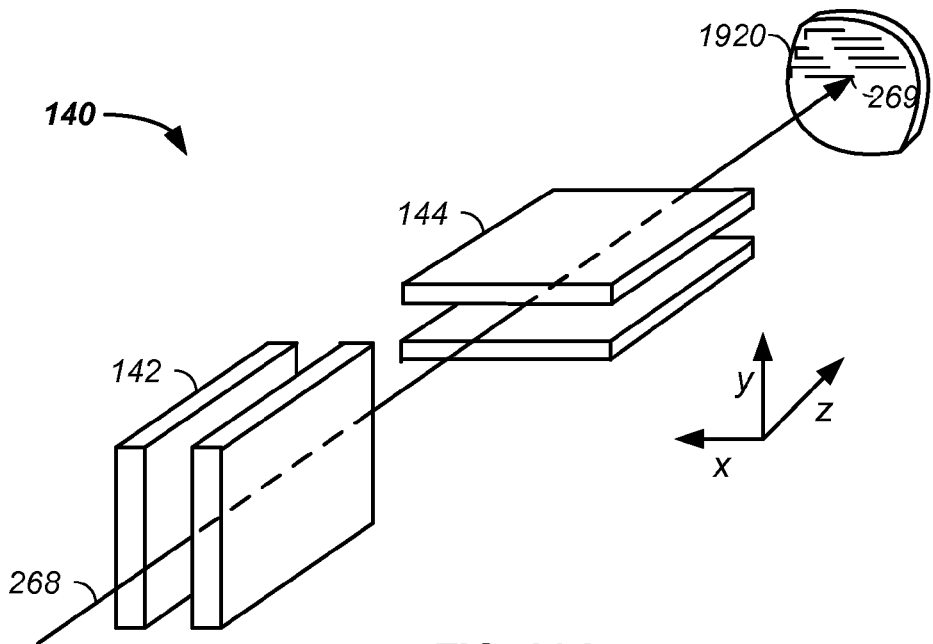
FIG. 20 illustrates multi-dimensional scanning of a charged particle beam spot scanning system operating on: (A) a 2-D slice or (B) a 3-D volume of a tumor.

For example, in the illustrated system in FIG. 20A, the spot is translated horizontally, is moved down a vertical, and is then back along the horizontal axis. In this example, current is used to control a vertical scanning system having at least one magnet. The applied current alters the magnetic field of the vertical scanning system to control the vertical deflection of the proton beam. Similarly, a horizontal scanning magnet system controls the horizontal deflection of the proton beam. The degree of transport along each axes is controlled to conform to the tumor cross-section at the given depth. The depth is controlled by changing the energy of the proton beam. For example, the proton beam energy is decreased, so as to define a new penetration depth, and the scanning process is repeated along the horizontal and vertical axes covering a new cross-sectional area of the tumor. Combined, the three axes of control allow scanning or movement of the proton beam focal point over the entire volume of the cancerous tumor. The time at each spot and the direction into the body for each spot is controlled to yield the desired radiation does at each sub-volume of the cancerous volume while distributing energy hitting outside of the tumor.

The focused beam spot volume dimension is preferably tightly controlled to a diameter of about 0.5, 1, or 2 millimeters, but is alternatively several centimeters in diameter. Preferred design controls allow scanning in two directions with: (1) a vertical amplitude of about 100 mm amplitude and frequency up to 200 Hz; and (2) a horizontal amplitude of about 700 mm amplitude and frequency up to 1 Hz. More or less amplitude in each axis is possible by altering the scanning magnet systems.

In FIG. 20A, the proton beam is illustrated along a z-axis controlled by the beam energy, the horizontal movement is along an x-axis, and the vertical direction is along a y-axis.

The distance the protons move along the z-axis into the tissue, in this example, is controlled by the kinetic energy of the proton. This coordinate system is arbitrary and exemplary. The actual control of the proton beam is controlled in 3-dimensional space using two scanning magnet systems and by controlling the kinetic energy of the proton beam. The use of the extraction system, described supra, allows for different scanning patterns. Particularly, the system allows simultaneous adjustment of the x-, y-, and z-axes in the irradiation of the solid tumor. Stated again, instead of scanning along an x,y-plane and then adjusting energy of the protons, such as with a range modulation wheel, the system allows for moving along the z-axes while simultaneously adjusting the x- and or y-axes. Hence, rather than irradiating slices of the tumor, the tumor is optionally irradiated in three simultaneous dimensions. For example, the tumor is irradiated around an outer edge of the tumor in three dimensions. Then the tumor is irradiated around an outer edge of an internal section of the tumor. This process is repeated until the entire tumor is irradiated. The outer edge irradiation is preferably coupled with simultaneous rotation of the subject, such as about a vertical y-axis. This system allows for maximum efficiency of deposition of protons to the tumor, as defined using the Bragg peak, to the tumor itself with minimal delivery of proton energy to surrounding healthy tissue.

Combined, the system allows for multi-axes control of the charged particle beam system in a small space with small power supply. For example, the system uses multiple magnets where each magnet has at least one edge focusing effect in each turning section of the synchrotron and/or multiple magnets having concentrating magnetic field geometry, as described supra. The multiple edge focusing effects in the circulating beam path of the synchrotron combined with the concentration geometry of the magnets and described extraction system yields a synchrotron having:
- a small circumference system, such as less than about 50 meters;
- a vertical proton beam size gap of about 2 cm;
- corresponding reduced power supply requirements associated with the reduced gap size;
- an extraction system not requiring a newly introduced magnetic field;
- acceleration or deceleration of the protons during extraction; and
- control of z-axis energy during extraction.

The result is a 3-dimensional scanning system, x-, y-, and z-axes control, where the z-axes control resides in the synchrotron and where the z-axes energy is variably controlled during the extraction process inside the synchrotron.

Figure 20B:
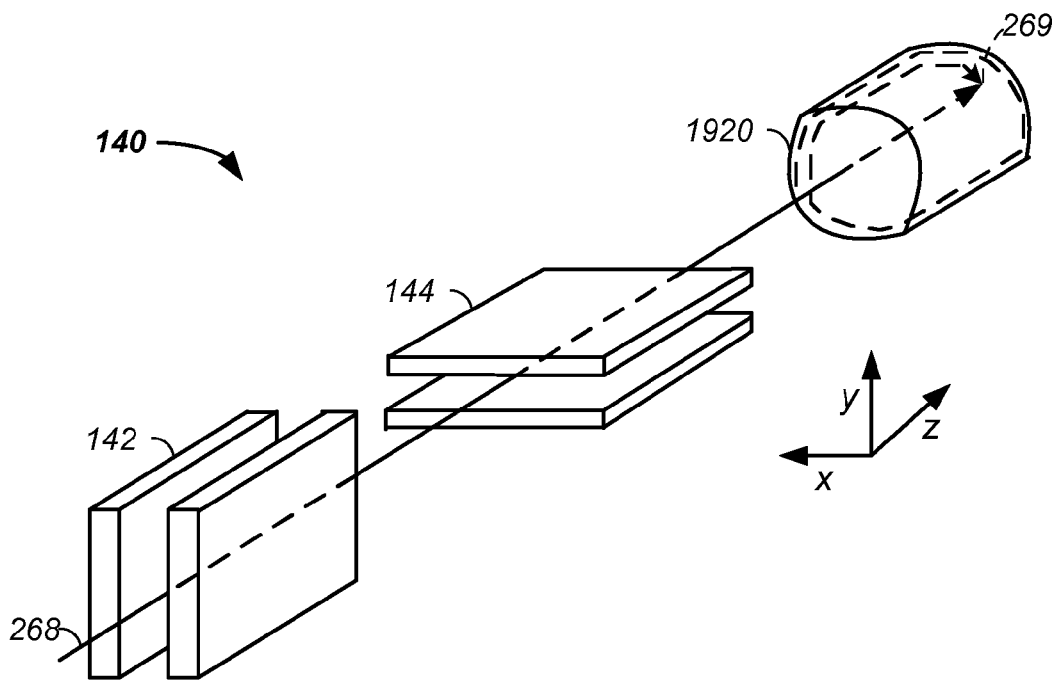

Referring now to FIG. 20B, an example of a proton scanning or targeting system 140 used to direct the protons to the tumor with 4-dimensional scanning control is provided, where the 4-dimensional scanning control is along the x-, y-, and z-axes along with intensity control, as described supra. A fifth axis is time. Typically, charged particles traveling along the transport path 268 are directed through a first axis control element 142, such as a vertical control, and a second axis control element 144, such as a horizontal control and into a tumor 1920. As described, supra, the extraction system also allows for simultaneous variation in the z-axis. Further, as describe, supra, the intensity or dose of the extracted beam is optionally simultaneously and independently controlled and varied. Thus instead of irradiating a slice of the tumor, as in FIG. 20A, all four dimensions defining the targeting spot of the proton delivery in the tumor are simultaneously variable. The simultaneous variation of the proton delivery spot is illustrated in FIG. 20B by the spot delivery path 269. In the illustrated case, the protons are initially directed around an outer edge of the tumor and are then directed around an inner radius of the tumor. Combined with rotation of the subject about a vertical axis, a multi-field illumination process is used where a not yet irradiated portion of the tumor is preferably irradiated at the further distance of the tumor from the proton entry point into the body. This yields the greatest percentage of the proton delivery, as defined by the Bragg peak, into the tumor and minimizes damage to peripheral healthy tissue.

Imaging/X-Ray System

Herein, an X-ray system is used to illustrate an imaging system.

Timing

An X-ray is preferably collected either (1) just before or (2) concurrently with treating a subject with proton therapy for a couple of reasons.

First, movement of the body, described supra, changes the local position of the tumor in the body relative to other body constituents. If the subject has an X-ray taken and is then bodily moved to a proton treatment room, accurate alignment of the proton beam to the tumor is problematic. Alignment of the proton beam to the tumor using one or more X-rays is best performed at the time of proton delivery or in the seconds or minutes immediately prior to proton delivery and after the patient is placed into a therapeutic body position, which is typically a fixed position or partially immobilized position.

Second, the X-ray taken after positioning the patient is used for verification of proton beam alignment to a targeted position, such as a tumor and/or internal organ position.

Positioning

An X-ray is preferably taken just before treating the subject to aid in patient positioning. For positioning purposes, an X-ray of a large body area is not needed. In one embodiment, an X-ray of only a local area is collected. When collecting an X-ray, the X-ray has an X-ray path. The proton beam has a proton beam path. Overlaying the X-ray path with the proton beam path is one method of aligning the proton beam to the tumor. However, this method involves putting the X-ray equipment into the proton beam path, taking the X-ray, and then moving the X-ray equipment out of the beam path. This process takes time. The elapsed time while the X-ray equipment moves has a couple of detrimental effects. First, during the time required to move the X-ray equipment, the body moves. The resulting movement decreases precision and/or accuracy of subsequent proton beam alignment to the tumor. Second, the time required to move the X-ray equipment is time that the proton beam therapy system is not in use, which decreases the total efficiency of the proton beam therapy system.

X-Ray Source Lifetime

It is desirable to have components in the particle beam therapy system that require minimal or no maintenance over the lifetime of the particle beam therapy system. For example, it is desirable to equip the proton beam therapy system with an X-ray system having a long lifetime source, such as a lifetime of about 20 years.

In one system, described infra, electrons are used to create X-rays. The electrons are generated at a cathode where the lifetime of the cathode is temperature dependent. Analogous to a light bulb, where the filament is kept in equilibrium, the cathode temperature is held in equilibrium at temperatures at about 200, 500, or 1000 degrees Celsius. Reduction of the cathode temperature results in increased lifetime of the cathode. Hence, the cathode used in generating the electrons is preferably held at as low of a temperature as possible. However, if the temperature of the cathode is reduced, then electron emissions also decrease. To overcome the need for more electrons at lower temperatures, a large cathode is used and the generated electrons are concentrated. The process is analogous to compressing electrons in an electron gun; however, here the compression techniques are adapted to apply to enhancing an X-ray tube lifetime.

Figure 21:
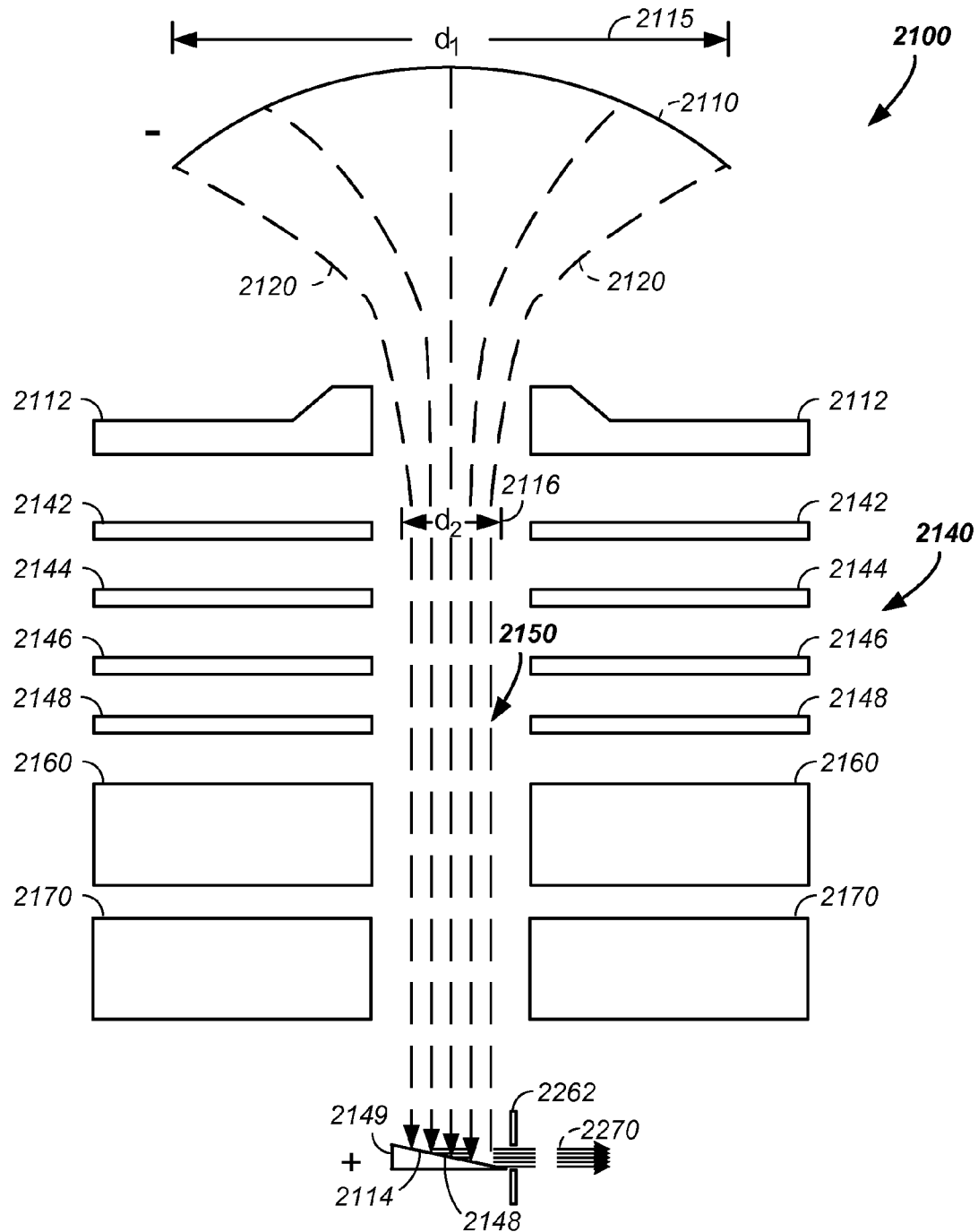
FIG. 21 illustrates an electron gun source used in generating X-rays coupled with a particle beam therapy system.

Referring now to FIG. 21, an example of an X-ray generation device 2100 having an enhanced lifetime is provided. Electrons 2120 are generated at a cathode 2110, focused with a control electrode 2112, and accelerated with a series of accelerating electrodes 2140. The accelerated electrons 2150 impact an X-ray generation source 2148 resulting in generated X-rays that are then directed along an X-ray path 2270 to the subject 1930. The concentrating of the electrons from a first diameter 2115 to a second diameter 2116 allows the cathode to operate at a reduced temperature and still yield the necessary amplified level of electrons at the X-ray generation source 2148. In one example, the X-ray generation source is the anode coupled with the cathode 2110 and/or the X-ray generation source is substantially composed of tungsten.

Still referring to FIG. 21, a more detailed description of an exemplary X-ray generation device 2100 is described. An anode 2114/cathode 2110 pair is used to generated electrons. The electrons 2120 are generated at the cathode 2110 having a first diameter 2115, which is denoted $d_1$. The control electrodes 2112 attract the generated electrons 2120. For example, if the cathode is held at about −150 kV and the control electrode is held at about −149 kV, then the generated electrons 2120 are attracted toward the control electrodes 2112 and focused. A series of accelerating electrodes 2140 are then used to accelerate the electrons into a substantially parallel path 2150 with a smaller diameter 2116, which is denoted $d_2$. For example, with the cathode held at −150 kV, a first, second, third, and fourth accelerating electrodes 2142, 2144, 2146, 2148 are held at about −120, −90, −60, and −30 kV, respectively. If a thinner body part is to be analyzed, then the cathode 2110 is held at a smaller level, such as about −90 kV and the control electrode, first, second, third, and fourth electrode are each adjusted to lower levels. Generally, the voltage difference from the cathode to fourth electrode is less for a smaller negative voltage at the cathode and vise-versa. The accelerated electrons 2150 are optionally passed through a magnetic lens 2160 for adjustment of beam size, such as a cylindrical magnetic lens. The electrons are also optionally focused using quadrupole magnets 2170, which focus in one direction and defocus in another direction. The accelerated electrons 2150, which are now adjusted in beam size and focused strike an X-ray generation source 2148, such as tungsten, resulting in generated X-rays that pass through an optional blocker 2262 and proceed along an X-ray path 2170 to the subject. The X-ray generation source 2148 is optionally cooled with a cooling element 2149, such as water touching or thermally connected to a backside of the X-ray generation source 2148. The concentrating of the electrons from a first diameter 2115 to a second diameter 2116 allows the cathode to operate at a reduced temperature and still yield the necessary amplified level of electrons at the X-ray generation source 2148.

More generally, the X-ray generation device 2100 produces electrons having initial vectors. One or more of the control electrode 2112, accelerating electrodes 2140, magnetic lens 2160, and quadrupole magnets 2170 combine to alter the initial electron vectors into parallel vectors with a decreased cross-sectional area having a substantially parallel path, referred to as the accelerated electrons 2150. The process allows the X-ray generation device 2100 to operate at a lower temperature. Particularly, instead of using a cathode that is the size of the electron beam needed, a larger electrode is used and the resulting electrons 2120 are focused and/or concentrated into the required electron beam needed. As lifetime is roughly an inverse of current density, the concentration of the current density results in a larger lifetime of the X-ray generation device. A specific example is provided for clarity. If the cathode has a 15 mm radius or $d_1$ is about 30 mm, then the area ($\pi r^2$) is about 225 mm$^2$ times pi. If the concentration of the electrons achieves a radius of 5 mm or $d_2$ is about 10 mm, then the area ($\pi r^2$) is about 25 mm$^2$ times pi. The ratio of the two areas is about 9 (225π/25π). Thus, there is about 9 times less density of current at the larger cathode compared to the traditional cathode having an area of the desired electron beam. Hence, the lifetime of the larger cathode approximates 9 times the lifetime of the traditional cathode, though the actual current through the larger cathode and traditional cathode is about the same. Preferably, the area of the cathode 2110 is about 2, 4, 6, 8, 10, 15, 20, or 25 times that of the cross-sectional area of the substantially parallel electron beam 2150.

In another embodiment of the invention, the quadrupole magnets 2170 result in an oblong cross-sectional shape of the electron beam 2150. A projection of the oblong cross-sectional shape of the electron beam 2150 onto the X-ray generation source 2148 results in an X-ray beam that has a small spot in cross-sectional view, which is preferably substantially circular in cross-sectional shape, that is then passed through the patient 1930. The small spot is used to yield an X-ray having enhanced resolution at the patient.

Figure 22:
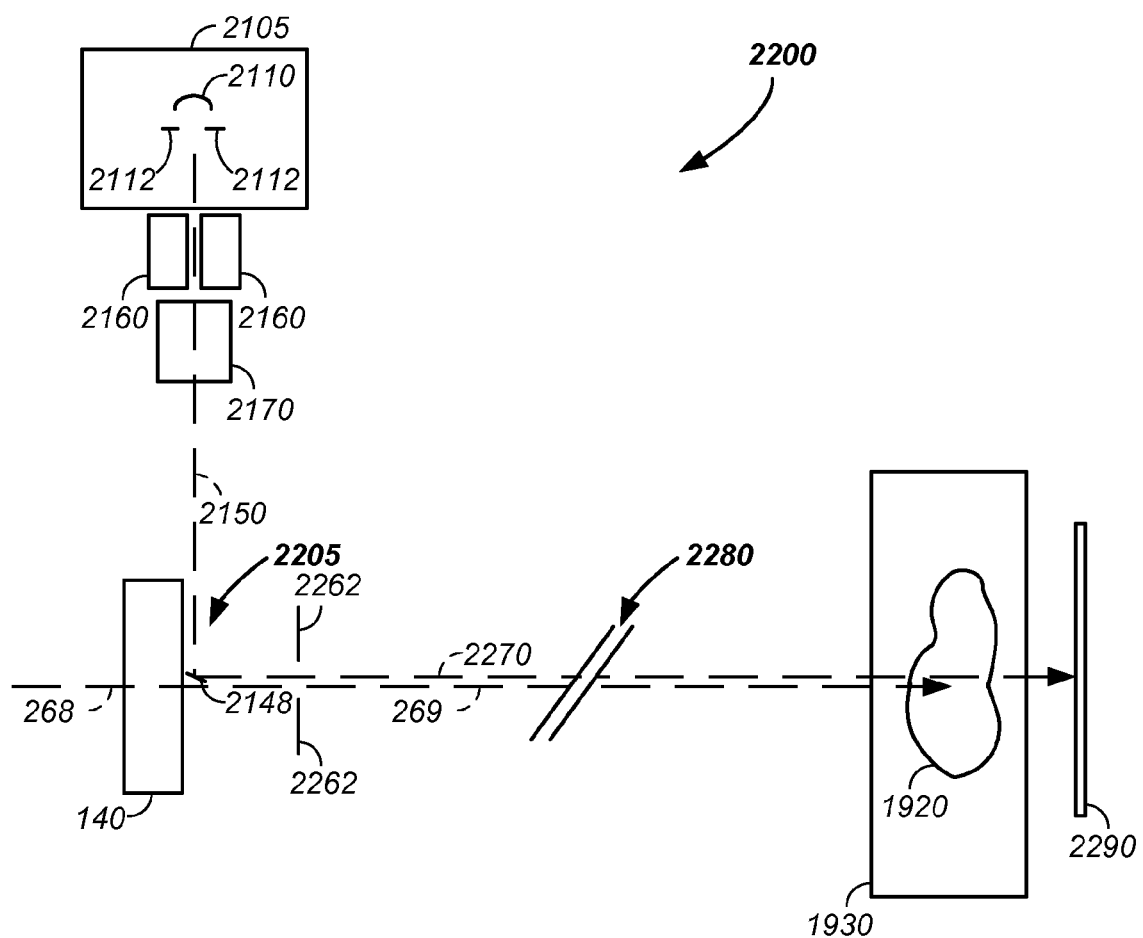
FIG. 22 illustrates an X-ray source proximate a particle beam path.

Referring now to FIG. 22, in one embodiment, an X-ray is generated close to, but not in, the proton beam path. A proton beam therapy system and an X-ray system combination 2200 is illustrated in FIG. 22. The proton beam therapy system has a proton beam 268 in a transport system after the Lamberson extraction magnet 292 of the synchrotron 130. The proton beam is directed by the scanning/targeting/delivery system 140 to a tumor 1920 of a patient 1930. The X-ray system 2205 includes an electron beam source 2105 generating an electron beam 2150. The electron beam is directed to an X-ray generation source 2148, such as a piece of tungsten. Preferably, the tungsten X-ray source is located about 1, 2, 3, 5, 10, 15, or 20 millimeters from the proton beam path 268. When the electron beam 2150 hits the tungsten, X-rays are generated in all directions. X-rays are blocked with a port 2262 and are selected for an X-ray beam path 2270. The X-ray beam path 2270 and proton beam path 268 run substantially in parallel as they progress to the tumor 1920. The distance between the X-ray beam path 2270 and proton beam path 269 preferably diminishes to near zero and/or the X-ray beam path 2270 and proton beam path 269 overlap by the time they reach the tumor 1920. Simple geometry shows this to be the case given the long distance, of at least a meter, between the tungsten and the tumor 1920. The distance is illustrated as a gap 2280 in FIG. 22. The X-rays are detected at an X-ray detector 2290, which is used to form an image of the tumor 1920 and/or position of the patient 1930.

As a whole, the system generates an X-ray beam that lies in substantially the same path as the proton therapy beam. The X-ray beam is generated by striking a tungsten or equivalent material with an electron beam. The X-ray generation source is located proximate to the proton beam path. Geometry of the incident electrons, geometry of the X-ray generation material, and/or geometry of the X-ray beam blocker 262 yield an X-ray beam that runs either in substantially in parallel with the proton beam or results in an X-ray beam path that starts proximate the proton beam path an expands to cover and transmit through a tumor cross-sectional area to strike an X-ray detector array or film allowing imaging of the tumor from a direction and alignment of the proton therapy beam. The X-ray image is then used to control the charged particle beam path to accurately and precisely target the tumor, and/or is used in system verification and validation.

Figure 23:
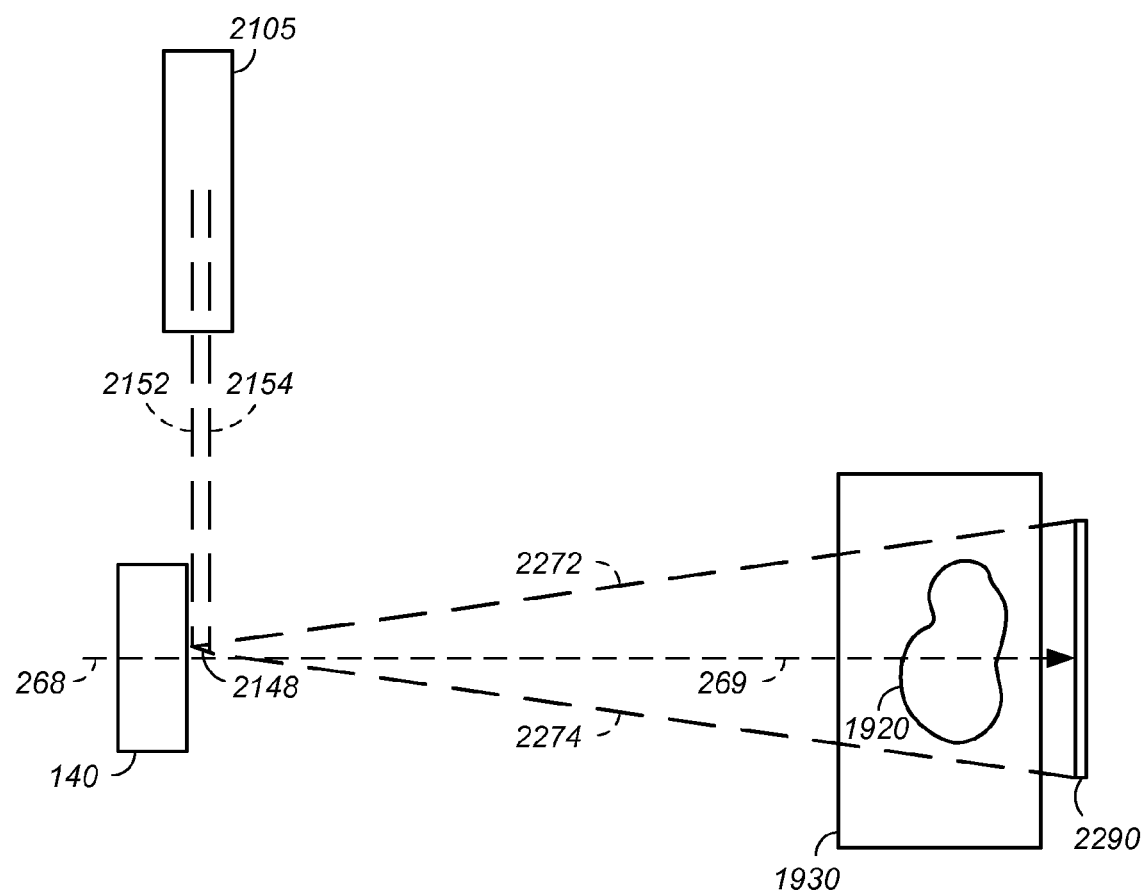
FIG. 23 illustrates an expanded X-ray beam path.

Referring now to FIG. 23, additional geometry of the electron beam path 2150 and X-ray beam path 2270 is illustrated. Particularly, the electron beam 2150 is shown as an expanded electron beam path 2152, 2154. Also, the X-ray beam path 2270 is shown as an expanded X-ray beam path 2272, 2274.

Patient Immobilization

Accurate and precise delivery of a proton beam to a tumor of a patient requires: (1) positioning control of the proton beam and (2) positioning control of the patient. As described, supra, the proton beam is controlled using algorithms and magnetic fields to a diameter of about 0.5, 1, or 2 millimeters. This section addresses partial immobilization, restraint, and/or alignment of the patient to insure the tightly controlled proton beam efficiently hits a target tumor and not surrounding healthy tissue as a result of patient movement.

In this section an x-, y-, and z-axes coordinate system and rotation axis is used to describe the orientation of the patient relative to the proton beam. The z-axis represent travel of the proton beam, such as the depth of the proton beam into the patient. When looking at the patient down the z-axis of travel of the proton beam, the x-axis refers to moving left or right across the patient and the y-axis refers to movement up or down the patient. A first rotation axis is rotation of the patient about the y-axis and is referred to herein as a rotation axis, bottom unit 1912 rotation axis, or y-axis of rotation. In addition, tilt is rotation about the x-axis, yaw is rotation about the y-axis, and roll is rotation about the z-axis. In this coordinate system, the proton beam path 269 optionally runs in any direction. As an illustrative matter, the proton beam path running through a treatment room is described as running horizontally through the treatment room.

In this section, three examples of positioning systems 2400 are provided: (1) a semi-vertical partial immobilization system; (2) a sitting partial immobilization system; and (3) a laying position. Elements described for one immobilization system apply to other immobilization systems with small changes. For example, a head rest will adjust along one axis for a reclined position, along a second axis for a seated position, and along a third axis for a laying position. However, the headrest itself is similar for each immobilization position.

Vertical Patient Positioning/Immobilization

The semi-vertical patient positioning system is preferably used in conjunction with proton therapy of tumors in the torso. The patient positioning and/or immobilization system controls and/or restricts movement of the patient during proton beam therapy. In a first partial immobilization embodiment, the patient is positioned in a semi-vertical position in a proton beam therapy system. As illustrated, the patient is reclining at an angle alpha, $\alpha$, about 45 degrees off of the y-axis as defined by an axis running from head to foot of the patient. More generally, the patient is optionally completely standing in a vertical position of zero degrees off the of y-axis or is in a semi-vertical position alpha that is reclined about 5, 10, 15, 20, 25, 30, 35, 40, 45, 50, 55, 60, or 65 degrees off of the y-axis toward the z-axis.

Patient positioning constraints are used to maintain the patient in a treatment position, including one or more of: a seat support, a back support, a head support, an arm support, a knee support, and a foot support. The constraints are optionally and independently rigid or semi-rigid. Examples of a semi-rigid material include a high or low density foam or a visco-elastic foam. For example the foot support is preferably rigid and the back support is preferably semi-rigid, such as a high density foam material. One or more of the positioning constraints are movable and/or under computer control for rapid positioning and/or immobilization of the patient. For example, the seat support is adjustable along a seat adjustment axis, which is preferably the y-axis; the back support is adjustable along a back support axis, which is preferably dominated by z-axis movement with a y-axis element; the head support is adjustable along a head support axis, which is preferably dominated by z-axis movement with a y-axis element; the arm support is adjustable along an arm support axis, which is preferably dominated by z-axis movement with a y-axis element; the knee support is adjustable along a knee support axis, which is preferably dominated by y-axis movement with a z-axis element; and the foot support is adjustable along a foot support axis, which is preferably dominated by y-axis movement with a z-axis element.

If the patient is not facing the incoming proton beam, then the description of movements of support elements along the axes change, but the immobilization elements are the same.

An optional camera is used with the patient immobilization system. The camera views the subject creating an video image. The image is provided to one or more operators of the charged particle beam system and allows the operators a safety mechanism for determining if the subject has moved or desires to terminate the proton therapy treatment procedure. Based on the video image, the operators optionally suspend or terminate the proton therapy procedure. For example, if the operator observes via the video image that the subject is moving, then the operator has the option to terminate or suspend the proton therapy procedure.

An optional video display is provided to the patient. The video display optionally presents to the patient any of: operator instructions, system instructions, status of treatment, or entertainment.

Motors for positioning the constraints, the camera, and video display are preferably mounted above or below the proton path.

Respiration control is optionally performed by using the video display. As the patient breathes, internal and external structures of the body move in both absolute terms and in relative terms. For example, the outside of the chest cavity and internal organs both have absolute moves with a breath. In addition, the relative position of an internal organ relative to another body component, such as an outer region of the body, a bone, support structure, or another organ, moves with each breath. Hence, for more accurate and precise tumor targeting, the proton beam is preferably delivered at point a in time where the position of the internal structure or tumor is well defined, such as at the bottom of each breath. The video display is used to help coordinate the proton beam delivery with the patient's respiration cycle. For example, the video display optionally displays to the patient a command, such as a hold breath statement, a breathe statement, a countdown indicating when a breath will next need to be held, or a countdown until respiration may resume.

Sitting Patient Positioning/Immobilization

In a second partial immobilization embodiment, the patient is partially restrained in a seated position. The sitting restraint system has support structures that are similar to the support structures used in the semi-vertical positioning system, described supra with the exception that the seat support is replaced by a chair and the knee support is not required. The seated restraint system generally retains the adjustable support, rotation about the y-axis, camera, video, and breath control parameters described in the semi-vertical embodiment, described supra.

Figure 24:
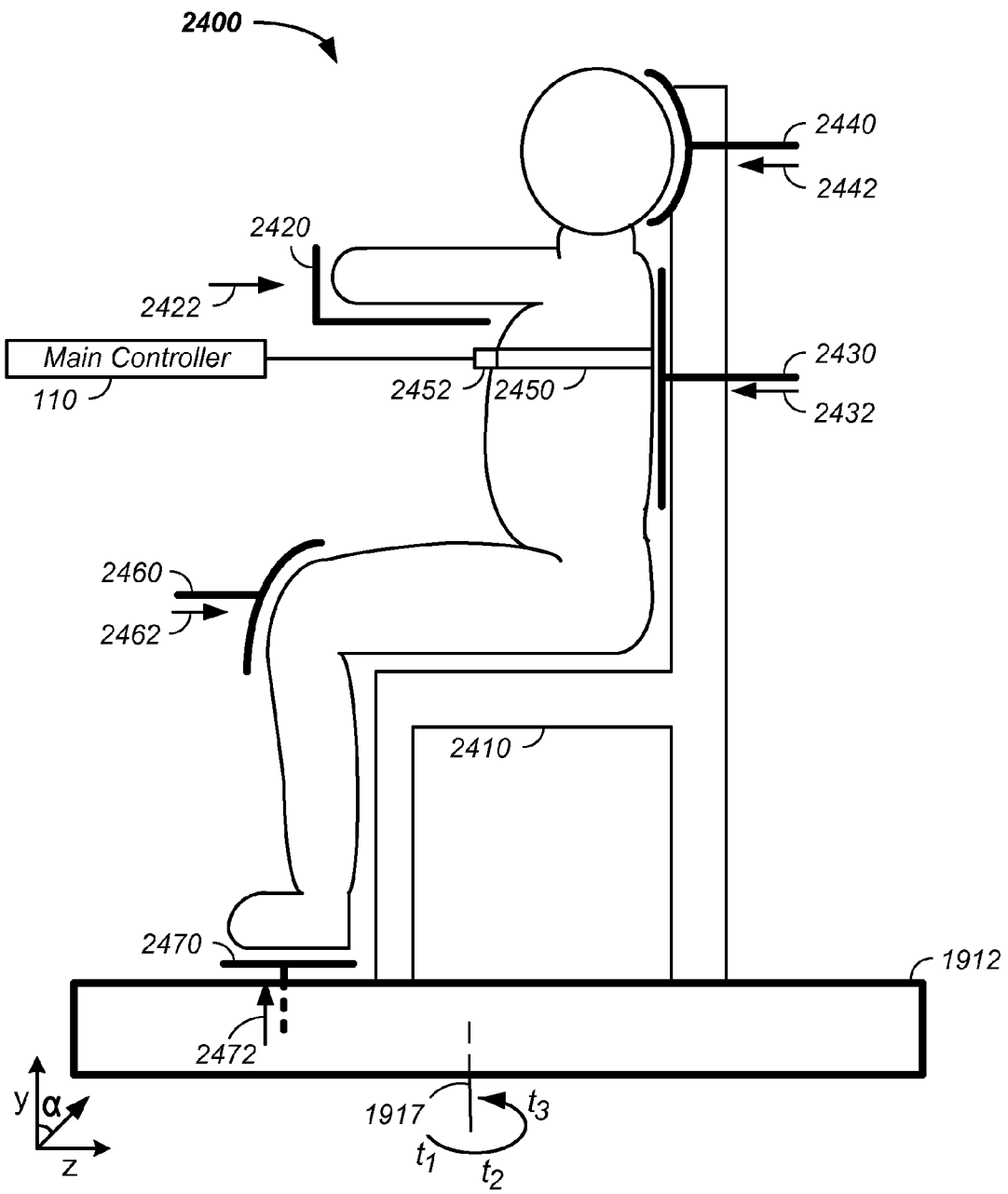
FIG. 24 provides an example of a patient positioning system.

Referring now to FIG. 24, a particular example of a sitting patient semi-immobilization system is provided. The sitting system is preferably used for treatment of head and neck tumors. As illustrated, the patient is positioned in a seated position on a chair 2410 for particle therapy. The patient is further immobilized using any of the: the head support 2440, the back support 2430, a hand support 2420, the knee support 2460, and the foot support 2470. The supports 2440, 2430, 2420, 2460, 2470 preferably have respective axes of adjustment 2442, 2432, 2422, 2462, 2472 as illustrated. The chair 2410 is either readily removed to allow for use of a different patient constraint system or adapts to a new patient position, such as the semi-vertical system.

Laying Patient Positioning/Immobilization

In a third partial immobilization embodiment, the patient is partially restrained in a laying position. The laying restraint system has support structures that are similar to the support structures used in the sitting positioning system and semi-vertical positioning system, described supra. In the laying position, optional restraint, support, or partial immobilization elements include one or more of: the head support and the back, hip, and shoulder support. The supports preferably have respective axes of adjustment that are rotated as appropriate for a laying position of the patient. The laying position restraint system generally retains the adjustable supports, rotation about the y-axis, camera, video, and breath control parameters described in the semi-vertical embodiment, described supra.

If the patient is very sick, such as the patient has trouble standing for a period of about one to three minutes required for treatment, then being in a partially supported system can result in some movement of the patient due to muscle strain. In this and similar situations, treatment of a patient in a laying position on a support table is preferentially used. The support table has a horizontal platform to support the bulk of the weight of the patient. Preferably, the horizontal platform is detachable from a treatment platform Additionally, leg support and/or arm support elements are optionally added to raise, respectively, an arm or leg out of the proton beam path 269 for treatment of a tumor in the torso or to move an arm or leg into the proton beam path 269 for treatment of a tumor in the arm or leg. This increases proton delivery efficiency, as described infra.

In a laying positioning system, the patient is positioned on a platform, which has a substantially horizontal portion for supporting the weight of the body in a horizontal position. Optional hand grips are used, described infra. One or more leg support elements are used to position the patient's leg. A leg support element is preferably adjustable along at least one leg adjustment axis or along an arc to position the leg into the proton beam path 269 or to remove the leg from the proton beam path 269, as described infra. An arm support element is preferably adjustable along at least one arm adjustment axis or along an arc to position the arm into the proton beam path 269 or to remove the arm from the proton beam path 269, as described infra. Both the leg support and arm support elements are optional.

Preferably, the patient is positioned on the platform in an area or room outside of the proton beam path 269 and is wheeled or slid into the treatment room or proton beam path area. For example, the patient is wheeled into the treatment room on a gurney where the top of the gurney, which is the platform, detaches and is positioned onto a table. The platform is preferably lifted onto the table or slid onto the table so that the gurney or bed need not be lifted onto the table.

The semi-vertical patient positioning system and sitting patient positioning system are preferentially used to treatment of tumors in the head or torso due to efficiency. The semi-vertical patient positioning system, sitting patient positioning system, and laying patient positioning system are all usable for treatment of tumors in the patient's limbs.

Support System Elements

Positioning constraints include all elements used to position the patient, such as those described in the semi-vertical positioning system, sitting positioning system, and laying positioning system. Preferably, positioning constraints or support system elements are aligned in positions that do not impede or overlap the proton beam path 269. However, in some instances the positioning constraints are in the proton beam path 269 during at least part of the time of treatment of the patient. For instance, a positioning constraint element may reside in the proton beam path 269 during part of a time period where the patient is rotated about the y-axis during treatment. In cases or time periods that the positioning constraints or support system elements are in the proton beam path, then an upward adjustment of proton beam energy is preferably applied that increases the proton beam energy to offset the positioning constraint element impedance of the proton beam. In one case, the proton beam energy is increased by a separate measure of the positioning constraint element impedance determined during a reference scan of the positioning constraint system element or set of reference scans of the positioning constraint element as a function of rotation about the y-axis.

For clarity, the positioning constraints or support system elements are herein described relative to the semi-vertical positioning system; however, the positioning elements and descriptive x-, y-, and z-axes are adjustable to fit any coordinate system, to the sitting positioning system, or the laying positioning system.

An example of a head support system is described to support, align, and/or restrict movement of a human head. The head support system preferably has several head support elements including any of: a back of head support, a right of head alignment element, and a left of head alignment element. The back of head support element is preferably curved to fit the head and is optionally adjustable along a head support axis, such as along the z-axis. Further, the head supports, like the other patient positioning constraints, is preferably made of a semi-rigid material, such as a low or high density foam, and has an optional covering, such as a plastic or leather. The right of head alignment element and left of head alignment elements or head alignment elements, are primarily used to semi-constrain movement of the head. The head alignment elements are preferably padded and flat, but optionally have a radius of curvature to fit the side of the head. The right and left head alignment elements are preferably respectively movable along translation axes to make contact with the sides of the head. Restricted movement of the head during proton therapy is important when targeting and treating tumors in the head or neck. The head alignment elements and the back of head support element combine to restrict tilt, rotation or yaw, roll and/or position of the head in the x-, y-, z-axes coordinate system.

Figure 25:
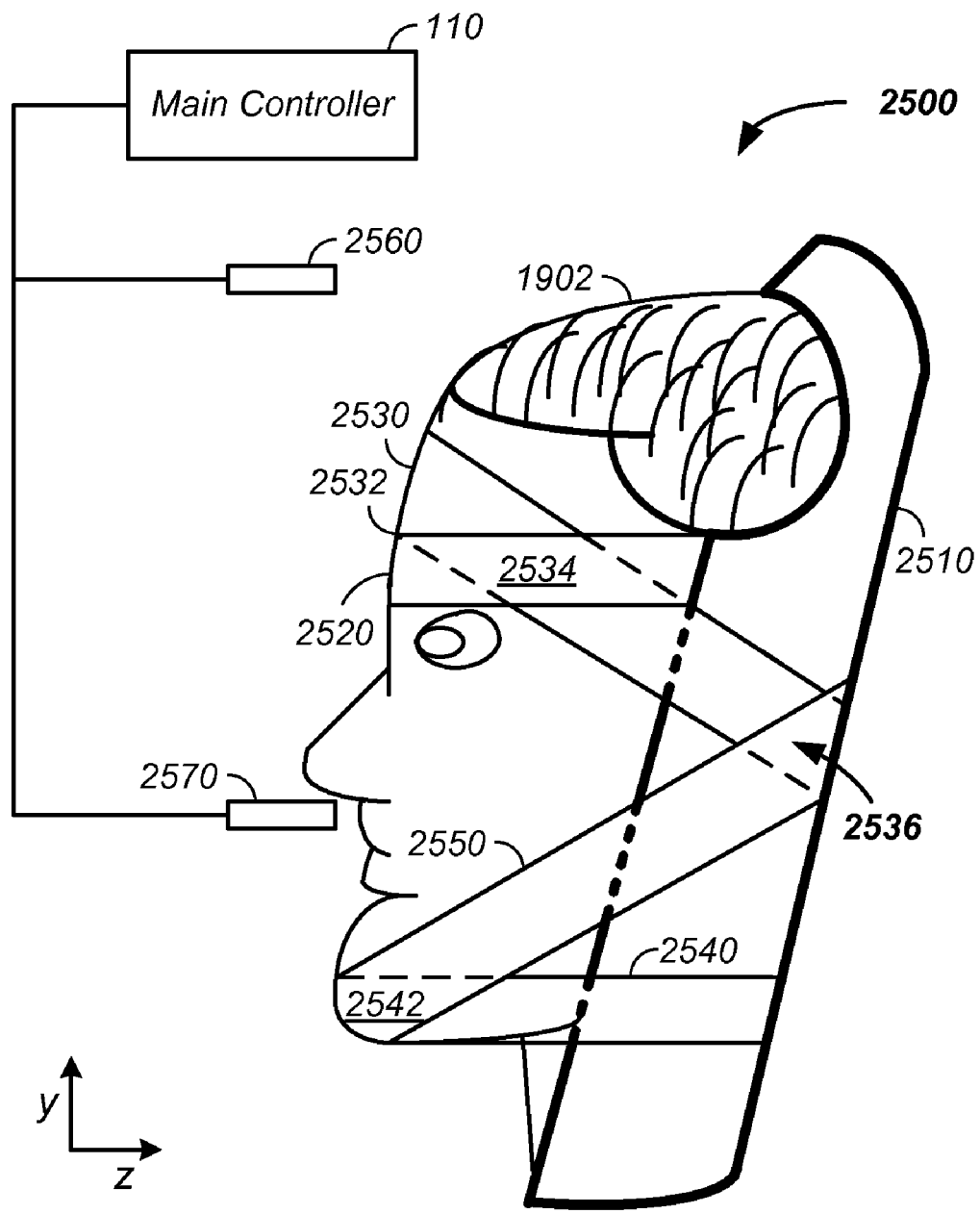
FIG. 25 illustrates a head restraint system.

Referring now to FIG. 25 another example of a head support system is described for positioning and/or restricting movement of a human head 1902 during proton therapy of a solid tumor in the head or neck. In this system, the head is restrained using 1, 2, 3, 4, or more straps or belts, which are preferably connected or replaceably connected to a back of head support element 2510. In the example illustrated, a first strap 2520 pulls or positions a forehead to the head support element 2510, such as by running predominantly along the z-axis. Preferably a second strap 2530 works in conjunction with the first strap 2520 to prevent the head from undergoing tilt, yaw, roll or moving in terms of translational movement on the x-, y-, and z-axes coordinate system. The second strap 2530 is preferably attached or replaceable attached to the first strap 2520 at or about: (1) a forehead position 2532; (2) at a point on one or both sides of the head 2534; and/or (3) at a position about the support element 2536. A third strap 2540 preferably orientates the chin of the subject relative to the support element 2510 by running dominantly along the z-axis. A fourth strap 2550 preferably runs along a predominantly y- and z-axes to hold the chin relative to the head support element 2510 and/or proton beam path. The third 2540 strap preferably is attached to or is replaceably attached to the fourth strap 2550 during use at or about the patient's chin position 2542. The second strap 2530 optionally connects to the fourth strap 2550 at or about the support element 2510. The four straps 2520, 2530, 2540, 2550 are illustrative in pathway and interconnection. Any of the straps optionally hold the head along different paths around the head and connect to each other in separate fashion. Naturally, a given strap preferably runs around the head and not just on one side of the head. Any of the straps 2520, 2530, 2540, and 2550 are optionally used independently or in combinations or permutations with the other straps. The straps are optionally indirectly connected to each other via a support element, such as the head support element 2510. The straps are optionally attached to the head support element 2510 using hook and loop technology, a buckle, or fastener. Generally, the straps combine to control position, front-to-back movement of the head, side-to-side movement of the head, tilt, yaw, roll, and/or translational position of the head.

The straps are preferably of known impedence to proton transmission allowing a calculation of peak energy release along the z-axis to be calculated, such as an adjustment to the Bragg peak is made based on the slowing tendency of the straps to proton transport.

Figure 26:
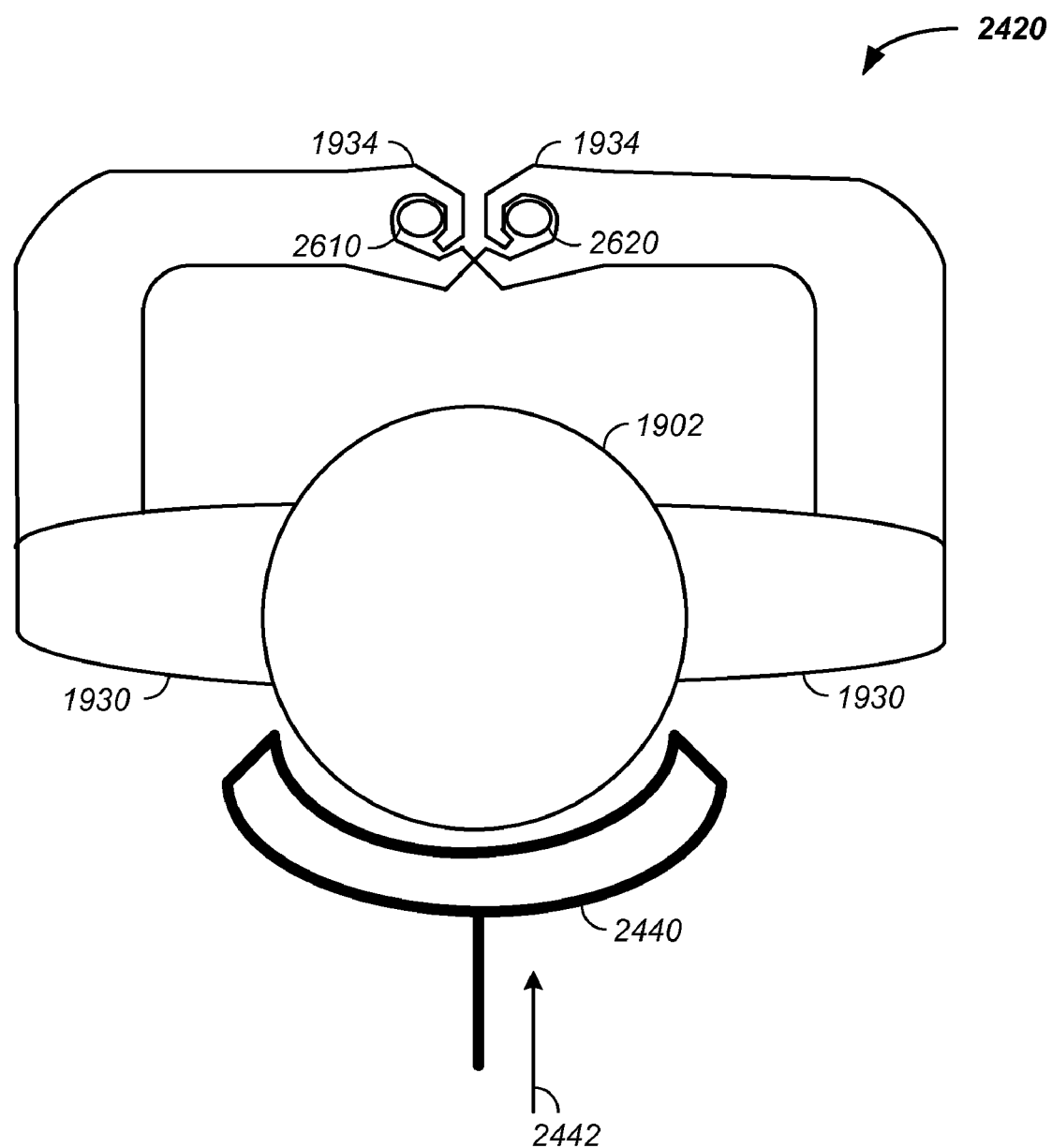
FIG. 26 illustrates hand and head supports.

Referring now to FIG. 26, still another example of a head support system 2440 is described. The head support 2440 is preferably curved to fit a standard or child sized head. The head support 2440 is optionally adjustable along a head support axis 2442. Further, the head supports, like the other patient positioning constraints, is preferably made of a semi-rigid material, such as a low or high density foam, and has an optional covering, such as a plastic or leather.

Elements of the above described head support, head positioning, and head immobilization systems are optionally used separately or in combination.

Still referring to FIG. 26, an example of the arm support 2420 is further described. The arm support preferably has a left hand grip 2610 and a right hand grip 2620 used for aligning the upper body of the patient 1930 through the action of the patient 1930 gripping the left and right hand grips 2610, 2620 with the patient's hands 1934. The left and right hand grips 2610, 2620 are preferably connected to the arm support 2420 that supports the mass of the patient's arms. The left and right hand grips 2610, 2620 are preferably constructed using a semi-rigid material. The left and right hand grips 2610, 2620 are optionally molded to the patient's hands to aid in alignment. The left and right hand grips optionally have electrodes, as described supra.

Positioning System Computer Control

One or more of the patient positioning unit components and/or one of more of the patient positioning constraints are preferably under computer control, where the computer control positioning devices, such as via a series of motors and drives, to reproducibly position the patient. For example, the patient is initially positioned and constrained by the patient positioning constraints. The position of each of the patient positioning constraints is recorded and saved by the main controller 110, by a sub-controller or the main controller 110, or by a separate computer controller. Then, medical devices are used to locate the tumor 1920 in the patient 1930 while the patient is in the orientation of final treatment. The imaging system 170 includes one or more of: MRI's, X-rays, CT's, proton beam tomography, and the like. Time optionally passes at this point where images from the imaging system 170 are analyzed and a proton therapy treatment plan is devised. The patient may exit the constraint system during this time period, which may be minutes, hours, or days. Upon return of the patient to the patient positioning unit, the computer can return the patient positioning constraints to the recorded positions. This system allows for rapid repositioning of the patient to the position used during imaging and development of the treatment plan, which minimizes setup time of patient positioning and maximizes time that the charged particle beam system 100 is used for cancer treatment.

Proton Delivery Efficiency

A Bragg peak energy profile shows that protons deliver their energy across the entire length of the body penetrated by the proton up to a maximum penetration depth. As a result, energy is being delivered to healthy tissue, bone, and other body constituents before the proton beam hits the tumor. It follows that the shorter the pathlength in the body prior to the tumor, the higher the efficiency of proton delivery efficiency, where proton delivery efficiency is a measure of how much energy is delivered to the tumor relative to healthy portions of the patient. Examples of proton delivery efficiency include: (1) a ratio proton energy delivered the tumor and proton energy delivered to non-tumor tissue; (2) pathlength of protons in the tumor versus pathlength in the non-tumor tissue; and (3) damage to a tumor compared to damage to healthy body parts. Any of these measures are optionally weighted by damage to sensitive tissue, such as a nervous system element, heart, brain, or other organ. To illustrate, for a patient in a laying position where the patient is rotated about the y-axis during treatment, a tumor near the hear would at times be treated with protons running through the head-to-heart path, leg-to-heart path, or hip-to-heart path, which are all inefficient compared to a patient in a sitting or semi-vertical position where the protons are all delivered through a shorter chest-to-heart; side-of-body-to-heart, or back-to-heart path. Particularly, compared to a laying position, using a sitting or semi-vertical position of the patient, a shorter pathlength through the body to a tumor is provided to a tumor located in the torso or head, which is a higher or better proton delivery efficiency.

Herein proton delivery efficiency is separately described from the time efficiency or synchrotron use efficiency, which is a fraction of time that the charged particle beam apparatus is in operation.

Patient Placement

Preferably, the patient 1930 is aligned in the proton beam path 269 in a precise and accurate manner. Several placement systems are described. The patient placement systems are described using the laying positioning system, but are equally applicable to the semi-vertical and sitting positioning systems.

In a first placement system, the patient is positioned in a known location relative to the platform. For example, one or more of the positioning constraints position the patient in a precise and/or accurate location on the platform. Optionally, a placement constraint element connected or replaceably connected to the platform is used to position the patient on the platform. The placement constraint element(s) is used to position any position of the patient, such as a hand, limb, head, or torso element.

In a second placement system, one or more positioning constraints or support element, such as the platform, is aligned versus an element in the patient treatment room. Essentially a lock and key system is optionally used, where a lock fits a key. The lock and key elements combine to locate the patient relative to the proton beam path 269 in terms of any of the x-, y-, and z-position, tilt, yaw, and roll. Essentially the lock is a first registration element and the key is a second registration element fitting into, adjacent to, or with the first registration element to fix the patient location and/or a support element location relative to the proton beam path 269. Examples of a registration element include any of a mechanical element, such as a mechanical stop, and an electrical connection indicating relative position or contact.

In a third placement system, the imaging system, described supra, is used to determine where the patient is relative to the proton beam path 269 or relative to an imaging marker placed in an support element or structure holding the patient, such as in the platform. When using the imaging system, such as an X-ray imaging system, then the first placement system or positioning constraints minimize patient movement once the imaging system determines location of the subject. Similarly, when using the imaging system, such as an X-ray imaging system, then the first placement system and/or second positioning system provide a crude position of the patient relative to the proton beam path 269 and the imaging system subsequently determines a fine position of the patient relative to the proton beam path 269.

Monitoring Respiration/Breathing

Preferably, the patient's respiration pattern is monitored. When a subject, also referred to herein as a patient, is breathing many portions of the body move with each breath. For example, when a subject breathes the lungs move as do relative positions of organs within the body, such as the stomach, kidneys, liver, chest muscles, skin, heart, and lungs. Generally, most or all parts of the torso move with each breath. Indeed, the inventors have recognized that in addition to motion of the torso with each breath, various motion also exists in the head and limbs with each breath. Motion is to be considered in delivery of a proton dose to the body as the protons are preferentially delivered to the tumor and not to surrounding tissue. Motion thus results in an ambiguity in where the tumor resides relative to the beam path. To partially overcome this concern, protons are preferentially delivered at the same point in each of a series of respiration cycles.

Initially, a rhythmic pattern of breathing of a subject is determined. The cycle is observed or measured. For example, a proton beam operator can observe when a subject is breathing or is between breaths and can time the delivery of the protons to a given period of each breath. Alternatively, the subject is told to inhale, exhale, and/or hold their breath and the protons are delivered during the commanded time period.

Preferably, one or more sensors are used to determine the respiration cycle of the individual. Two examples of a respiration monitoring system are provided: (1) a thermal monitoring system and (2) a force monitoring system.

Referring again to FIG. 25, an example of the thermal respiration monitoring system is provided. In the thermal respiration monitoring system, a sensor is placed by the nose and/or mouth of the patient. As the jaw of the patient is optionally constrained, as described supra, the thermal respiration monitoring system is preferably placed by the patient's nose exhalation path. To avoid steric interference of the thermal sensor system components with proton therapy, the thermal respiration monitoring system is preferably used when treating a tumor not located in the head or neck, such as a when treating a tumor in the torso or limbs. In the thermal monitoring system, a first thermal resistor 2570 is used to monitor the patient's respiration cycle and/or location in the patient's respiration cycle. Preferably, the first thermal resistor 2570 is placed by the patient's nose, such that the patient exhaling through their nose onto the first thermal resistor 2570 warms the first thermal resistor 2570 indicating an exhale. Preferably, a second thermal resistor 2560 operates as an environmental temperature sensor. The second thermal resistor 2560 is preferably placed out of the exhalation path of the patient but in the same local room environment as the first thermal resistor 2570. Generated signal, such as current from the thermal resistors 2570, 2560, is preferably converted to voltage and communicated with the main controller 110 or a sub-controller of the main controller. Preferably, the second thermal resistor 2560 is used to adjust for the environmental temperature fluctuation that is part of a signal of the first thermal resistor 2570, such as by calculating a difference between the values of the thermal resistors 2570, 2560 to yield a more accurate reading of the patient's respiration cycle.

Referring again to FIG. 24, an example of the force/pressure respiration monitoring system is provided. In the force based respiration monitoring system, a sensor is placed by the torso. To avoid steric interference of the force sensor system components with proton therapy, the forced based respiration monitoring system is preferably used when treating a tumor located in the head, neck or limbs. In the force monitoring system, a belt or strap 2450 is placed around an area of the patient's torso that expands and contracts with each respiration cycle of the patient. The belt 2450 is preferably tight about the patient's chest and is flexible. A force meter 2452 is attached to the belt and senses the patients breathing or respiration pattern. The forces applied to the force meter 2452 correlate with periods or repeating patterns of the respiration cycle. The signals from the force meter 2452 are preferably communicated with the main controller 110 or a sub-controller of the main controller.

Respiration Control

Once the rhythmic pattern of the subject's breathing is determined, a signal is optionally delivered to the subject to more precisely control the respiration frequency. For example, a display screen is placed in front of the subject directing the subject when to hold their breath and when to breathe. Typically, a respiration control module uses input from one or more of the respiration sensors. For example, the input is used to determine when the next breath exhale is to complete. At the bottom of the breath, the control module displays a hold breath signal to the subject, such as on a monitor, via an oral signal, digitized and automatically generated voice command, or via a visual control signal. Preferably, a display monitor is positioned in front of the subject and the display monitor displays at least breathing commands to the subject. Typically, the subject is directed to hold their breath for a short period of time, such as about one-half, one, two, or three seconds. The period of time the subject is asked to hold their breath is less than about ten seconds. The period of time the breath is held is preferably synchronized to the delivery time of the proton beam to the tumor, which is about one-half, one, two, or three seconds. While delivery of the protons at the bottom of the breath is preferred, protons are optionally delivered at any point in the respiration cycle, such as upon full inhalation. Delivery at the top of the breath or when the patient is directed to inhale deeply and hold their breath by the respiration control module is optionally performed as at the top of the breath the chest cavity is largest and for some tumors the distance between the tumor and surrounding tissue is maximized or the surrounding tissue is rarefied as a result of the increased volume. Hence, protons hitting surrounding tissue is minimized. Optionally, the display screen tells the subject when they are about to be asked to hold their breath, such as with a 3, 2, 1, second countdown so that the subject is aware of the task they are about to be asked to perform.

Proton Beam Therapy Synchronization with Respiration

A proton delivery control algorithm is used to synchronize delivery of the protons to the tumor within a given period of each breath, such as at the top or bottom of a breath when the subject is holding their breath. The proton delivery control algorithm is preferably integrated with the respiration control module. Thus, the proton delivery control algorithm knows when the subject is breathing, where in the respiration cycle the subject is, and/or when the subject is holding their breath. The proton delivery control algorithm controls when protons are injected and/or inflected into the synchrotron, when an RF signal is applied to induce an oscillation, as described supra, and when a DC voltage is applied to extract protons from the synchrotron, as described supra. Typically, the proton delivery control algorithm initiates proton inflection and subsequent RF induced oscillation before the subject is directed to hold their breath or before the identified period of the respiration cycle selected for a proton delivery time. In this manner, the proton delivery control algorithm can deliver protons at a selected period of the respiration cycle by simultaneously or nearly simultaneously delivering the high DC voltage to the second pair of plates, described supra, which results in extraction of the protons from the synchrotron and subsequent delivery to the subject at the selected time point. Since the period of acceleration of protons in the synchrotron is constant or known for a desired energy level of the proton beam, the proton delivery control algorithm is used to set an AC RF signal that matches the breathing cycle or directed breathing cycle or pattern of the subject.

Multi-Field Irradiation

The 3-dimensional scanning system of the proton spot focal point, described supra, is preferably combined with a rotation/raster method. The method includes layer wise tumor irradiation from many directions. During a given irradiation slice, the proton beam energy is continuously changed according to the tissue's density in front of the tumor to result in the beam stopping point, defined by the Bragg peak, to always be inside the tumor and inside the irradiated slice. The novel method allows for irradiation from many directions, referred to herein as multi-field irradiation, to achieve the maximal effective dose at the tumor level while simultaneously significantly reducing possible side-effects on the surrounding healthy tissues in comparison with existing methods. Essentially, the multi-field irradiation system distributes dose-distribution at tissue depths not yet reaching the tumor.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. An apparatus for injecting a charged particle beam into an accelerator of an irradiation device, said irradiation device irradiating a tumor during use, said apparatus comprising:
   a negative ion source, said negative ion source configured to produce negative ions in a negative ion beam; and
   a converting foil, said converting foil configured to convert the negative ion beam into the charged particle beam, wherein said converting foil provides a pressure seal between an ion beam formation side of said irradiation device and a synchrotron side of said irradiation device, wherein a first pump system operates to maintain a first vacuum in said ion beam formation side of said converting foil, wherein a second pump system operates to maintain a second vacuum in said synchrotron side of said irradiation device.

2. The apparatus of claim 1, wherein said converting foil configured to convert the negative ions into a proton beam, wherein said converting foil provides a vacuum barrier between the negative ions and the charged particle beam, wherein the charged particle beam comprises a proton beam.

3. The apparatus of claim 1, wherein said converting foil comprises:
   a beryllium carbon film, wherein said carbon film comprises a thickness of about thirty to two hundred micrometers, wherein said carbon film forms a vacuum barrier between said negative ion source and said synchrotron.

4. The apparatus of claim 1, further comprising:
   an ion beam focusing lens, said lens configured to during use comprise field lines running, in a vacuum system, through the negative ion beam, wherein the field lines focus the negative ion beam,
   said ion beam focusing lens further comprising:
      a first focusing electrode circumferentially surrounding the negative ion beam;
      a second focusing electrode comprising metal conductive paths at least partially blocking the negative ion beam;
      wherein during use first electric field lines run between said first focusing electrode and said second focusing electrode,
      wherein during use the negative ions encounter first force vectors running up the first electric field lines that focus the negative ion beam,
      wherein said first focusing electrode and said second focusing electrode comprises opposite charge.

5. The apparatus of claim 4, wherein said metal conductive paths comprise any of:
   a series of conductive lines running substantially in parallel across the negative ion beam;
   a conductive grid crossing the negative ion beam; and
   a focusing foil crossing the negative ion beam, said focusing foil having holes, said holes comprising a combined cross-sectional area of at least ninety percent of the cross-sectional area of the negative ion beam.

6. The apparatus of claim 5, further comprising:
   a third focusing electrode circumferentially surrounding the negative ion beam, wherein said second focusing electrode comprises a position between said first focusing electrode and said third focusing electrode,
   wherein during use said third focusing electrode comprises a negative charge,
   wherein during use second electric field lines run between said third focusing electrode and said second focusing electrode, wherein during use the negative ions encounter second force vectors running up the second electric field lines that focus the negative ion beam.

7. The apparatus of claim 1, wherein said negative ion source further comprises:
a magnetic material configured to produce a magnetic field loop,
wherein the magnetic field loop yields a magnetic barrier between a high temperature plasma chamber and a low temperature plasma region,
wherein said magnetic barrier selectively passes elements of plasma in said high temperature plasma chamber to said low temperature plasma region,
wherein low energy electrons interact with atomic hydrogen to create hydrogen anions in said low temperature plasma region;
wherein application of a high voltage pulse extracts negative ions from said negative ion source to form the negative ion beam.

8. The apparatus of claim 1, wherein said negative ion source further comprises:
a magnetic field barrier separating a high energy plasma region from a low temperature plasma zone.

9. The apparatus of claim 8, wherein a magnetic material within said high energy plasma region generates the magnetic field barrier.

10. The apparatus of claim 9, further comprising:
a first ion generation electrode at a first end of said high temperature plasma chamber; and
a second ion generation electrode at a second end of said high temperature plasma chamber,
wherein application of a first high voltage pulse across said first ion generation electrode and said second ion generation electrode breaks hydrogen in said high temperature plasma chamber into component parts.

11. The apparatus of claim 10, further comprising a third ion generation electrode, wherein application of a second high voltage pulse across said second ion generation electrode and said third ion generation electrode extracts negative ions from the low temperature plasma zone to form the negative ion beam.

12. The apparatus of claim 11, further comprising a magnetic field carrying outer wall about said high energy plasma region,
wherein said magnetic material yields a magnetic field loop running through said first ion generation electrode, through said magnetic field carrying outer wall, through said second ion generation electrode, across a gap, and through said magnetic material.

13. The apparatus of claim 1, wherein said accelerator comprises a synchrotron, said synchrotron comprising:
an extraction material;
at least a one kilovolt direct current field applied across a pair of extraction blades; and
a deflector,
wherein during use the charged particle beam passes through said extraction material resulting in a reduced energy charged particle beam,
wherein the reduced energy charged particle beam passes between said pair of extraction blades, and
wherein the direct current field redirects the reduced energy charged particle beam out of said synchrotron through said deflector,
wherein said deflector yields an extracted charged particle beam.

14. The apparatus of claim 13, further comprising an intensity controller controlling intensity of the extracted charged particle beam via a feedback control.

15. The apparatus of claim 14, wherein during use an induced current results from the charged particle beam passing through said extraction material, wherein the induced current comprises a feedback input to said intensity controller.

16. The apparatus of claim 13, further comprising an X-ray source located within less than about fifty millimeters of the extracted charged particle beam, wherein said X-ray source maintains position during use of said X-ray source, wherein said X-ray source maintains position during tumor treatment with the extracted charged particle beam.

17. The apparatus of claim 1, wherein said irradiation device further comprises:
a rotatable platform rotating during an irradiation period;
an immobilization system mounted on said first rotatable platform, wherein said immobilization system restricts tumor motion during delivery of the extracted charged particle beam,
wherein said rotatable platform rotates to at least ten irradiation positions during tumor irradiation with the extracted charged particle beam.

18. A method for injecting a charged particle beam into an accelerator of an irradiation device, said irradiation device irradiating a tumor during use, said method comprising the steps of:
producing negative ions in a negative ion beam with a negative ion source;
converting the negative ion beam into the charged particle beam with a converting foil, said converting foil providing a vacuum barrier between the negative ion source and said accelerator, wherein said accelerator comprises a synchrotron; and
injecting the charged particle beam into said accelerator.

19. The method of claim 18, wherein said converting foil comprises:
a beryllium carbon film, wherein said carbon film comprises a thickness of about thirty to two hundred micrometers.

20. The method of claim 18, further comprising the steps of:
circumferentially surrounding the negative ion beam with a first focusing electrode;
providing a second focusing electrode, said second focusing electrode comprising metal conductive paths at least partially blocking the negative ion beam;
wherein first electric field lines run between said first focusing electrode and said second focusing electrode,
wherein the negative ions encounter first force vectors running up said first electric field lines that focus the negative ion beam,
wherein said first focusing electrode and said second focusing electrode comprises opposite charges; and
focusing the negative ion beam using the first electric field lines, wherein the first electric field lines run in a vacuum system, through the negative ion beam.

21. The method of claim 20, wherein said metal conductive paths comprise any of:
a series of wires running substantially in parallel across the negative ion beam;
a conductive grid crossing the negative ion beam; and
a focusing foil crossing the negative ion beam, said focusing foil having holes, said holes comprising a combined cross-sectional area of at least ninety percent of the cross-sectional area of the negative ion beam.

22. The method of claim 20, further comprising the step of:
circumferentially surrounding the negative ion beam with a third focusing electrode, wherein said second focusing electrode comprises a position between said first focusing electrode and said third focusing electrode,
wherein second electric field lines run between said third focusing electrode and said second focusing electrode,
wherein the negative ions encounter second force vectors running up said second electric field lines that focus the negative ion beam.

23. The method of claim 20, further comprising the step of:
producing a magnetic field loop with a magnetic material at least partially located inside said negative ion source, wherein said magnetic field loop yields a magnetic barrier between a high temperature plasma chamber and a low temperature plasma region, wherein said magnetic barrier selectively passes elements of plasma in said high temperature plasma chamber to said low temperature plasma region, wherein low energy electrons interact with atomic hydrogen to create hydrogen anions in said low temperature plasma region; and
applying a high voltage pulse across said low temperature plasma region to extract negative ions from said negative ion source to form the negative ion beam.

24. The method of claim 23, further comprising the step of:
applying a first high voltage pulse across a first ion generation electrode at a first end of said high temperature plasma chamber and a second ion generation electrode at a second end of said high temperature plasma chamber,
wherein application of said first high voltage pulse across said first ion generation electrode and said second ion generation electrode breaks hydrogen in said high temperature plasma chamber into component parts,
wherein said first high voltage pulse comprises a pulse of at least four kilovolts for a period of at least fifteen microseconds.

25. The method of claim 24, further comprising the steps of:
applying a second high voltage pulse across the low temperature plasma zone with an extraction electrode,
wherein said second high voltage pulse comprises a pulse of at least twenty kilovolts during a period overlapping the last five microseconds of said first high voltage pulse,
wherein said second high voltage pulse comprises a pulse of at least twenty kilovolts during a period overlapping at least three microseconds of said first high voltage pulse, and
providing a second high voltage pulse across said second ion generation electrode and a third ion generation electrode, wherein application of the second high voltage pulse extracts negative ions from the low temperature plasma zone to form the negative ion beam.

26. The method of claim 18, further comprising the step of:
extracting the charged particle beam from said accelerator, said step of extracting comprising the steps of:
transmitting the charged particle beam through an extraction material, said extraction material yielding a reduced energy charged particle beam;
applying an extraction field of at least five hundred volts across a pair of extraction blades;
passing the reduced energy charged particle beam between said pair of extraction blades,
wherein said extraction field redirects the reduced energy charged particle as an energy controlled extracted charged particle beam.

27. The method of claim 26, further comprising the step of:
controlling intensity of the extracted charged beam with an intensity controller.

28. The method of claim 27, wherein said step of controlling comprises the steps of:
inputting a feedback signal to said intensity controller, said step of transmitting yielding emitted electrons in the process of the charged particle beam striking said extraction material, wherein the emitted electrons are converted to said feedback signal;
comparing said feedback signal to an irradiation plan intensity;
adjusting betatron oscillation with said intensity controller until said feedback signal proximately equals said irradiation plan intensity,
wherein said energy controlled extracted charged particle beam comprises an independent intensity control.

29. The method of claim 26, further comprising the step of:
generating a tumor X-ray image using an X-ray source located within less than about fifty millimeters of the extracted charged particle beam, wherein said X-ray source maintains position during use of said X-ray source and said X-ray source maintaining a static position during tumor treatment with the extracted charged particle beam.

30. The method of claim 29, further comprising the steps of:
rotating a rotatable platform of said irradiation device during an irradiation period;
providing an immobilization system mounted on said first rotatable platform, wherein said immobilization system restricts tumor motion during delivery of the charged particle beam; and
irradiating the tumor with said irradiation device, wherein said rotatable platform rotates to at least ten irradiation positions during said step of irradiating.

\* \* \* \* \*